(12) United States Patent
Moseley et al.

(10) Patent No.: US 11,992,410 B1
(45) Date of Patent: May 28, 2024

(54) SACROILIAC JOINT FUSION IMPLANTS, INSERTION INSTRUMENTS, AND METHODS

(71) Applicant: Spinal Simplicity, LLC, Overland Park, KS (US)

(72) Inventors: Todd Moseley, Olathe, KS (US); Melissa Frock, Lenexa, KS (US); Colton McQuinn, Grandview, MO (US); Jeffrey David Lee, Prairie Village, KS (US); Nick Furman, Raymore, MO (US); Adam Frock, Lenexa, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 18/504,856

(22) Filed: Nov. 8, 2023

Related U.S. Application Data

(60) Provisional application No. 63/498,649, filed on Apr. 27, 2023, provisional application No. 63/576,430, filed on Dec. 13, 2022.

(51) Int. Cl.
  *A61F 2/30* (2006.01)
  *A61B 17/16* (2006.01)
  *A61F 2/44* (2006.01)

(52) U.S. Cl.
  CPC ...... *A61F 2/30988* (2013.01); *A61B 17/1671* (2013.01); *A61F 2/30771* (2013.01); *A61F 2002/3085* (2013.01); *A61F 2002/30995* (2013.01)

(58) Field of Classification Search
  CPC .................. A61F 2/30988; A61F 2/30771
  See application file for complete search history.

(56) References Cited

U.S. PATENT DOCUMENTS

| | | | | | |
|---|---|---|---|---|---|
| 4,175,555 | A | * | 11/1979 | Herbert | A61B 17/863 606/304 |
| 5,545,226 | A | * | 8/1996 | Wingo | A61L 27/16 623/17.19 |
| 6,039,761 | A | * | 3/2000 | Li | A61F 2/4455 623/17.16 |
| 6,053,916 | A | * | 4/2000 | Moore | A61F 2/30988 606/86 R |

(Continued)

OTHER PUBLICATIONS

PCT Patent Application PCT/US2023/082673 International Search Report and the Written Opinion, issued Mar. 21, 2024.

*Primary Examiner* — Christian A Sevilla
(74) *Attorney, Agent, or Firm* — Erise IP, P.A.

(57) ABSTRACT

Systems, methods, and devices for sacroiliac joint fusion described include an implant comprising a first body having a distal anchor and a second body having proximal anchor. The first body includes a threaded body integrally formed with the first body or threadably coupled to the first body. The distal anchor may be formed by a pair of deployable wings. The pair of deployable wings may be deployed within the cancellous bone of the sacrum and anchored against the cortical bone of the sacrum. The proximal anchor may engage with an outer surface of the ilium. The second body may be threaded along the threaded body to provide compression across the sacroiliac joint. Compressing the sacroiliac joint can reduce motion thereof to promote fusion and stabilization.

20 Claims, 48 Drawing Sheets

(56) References Cited

U.S. PATENT DOCUMENTS

| | | | |
|---|---|---|---|
| 7,491,236 B2 * | 2/2009 | Cragg | A61F 2/441 606/301 |
| 9,757,164 B2 | 9/2017 | Hess et al. | |
| 9,861,399 B2 | 1/2018 | Rogers et al. | |
| 9,907,581 B2 | 3/2018 | Hess et al. | |
| 10,285,739 B2 | 5/2019 | Frock et al. | |
| 11,534,310 B2 | 12/2022 | Frock et al. | |
| 2003/0028196 A1 * | 2/2003 | Bonutti | A61G 13/0054 606/87 |
| 2011/0184518 A1 * | 7/2011 | Trieu | A61B 17/562 623/17.11 |
| 2016/0310188 A1 * | 10/2016 | Marino | A61F 2/28 |
| 2017/0258498 A1 | 9/2017 | Redmond et al. | |
| 2020/0085474 A1 | 3/2020 | Harshman et al. | |
| 2022/0175548 A1 | 6/2022 | Frock et al. | |
| 2022/0226027 A1 | 7/2022 | Rogers et al. | |
| 2023/0088125 A1 | 3/2023 | Frock et al. | |
| 2023/0240725 A1 | 8/2023 | Frock et al. | |
| 2023/0320764 A1 | 10/2023 | Slover et al. | |
| 2023/0329761 A1 | 10/2023 | Rogers et al. | |
| 2023/0329871 A1 | 10/2023 | Greenhalgh et al. | |

* cited by examiner

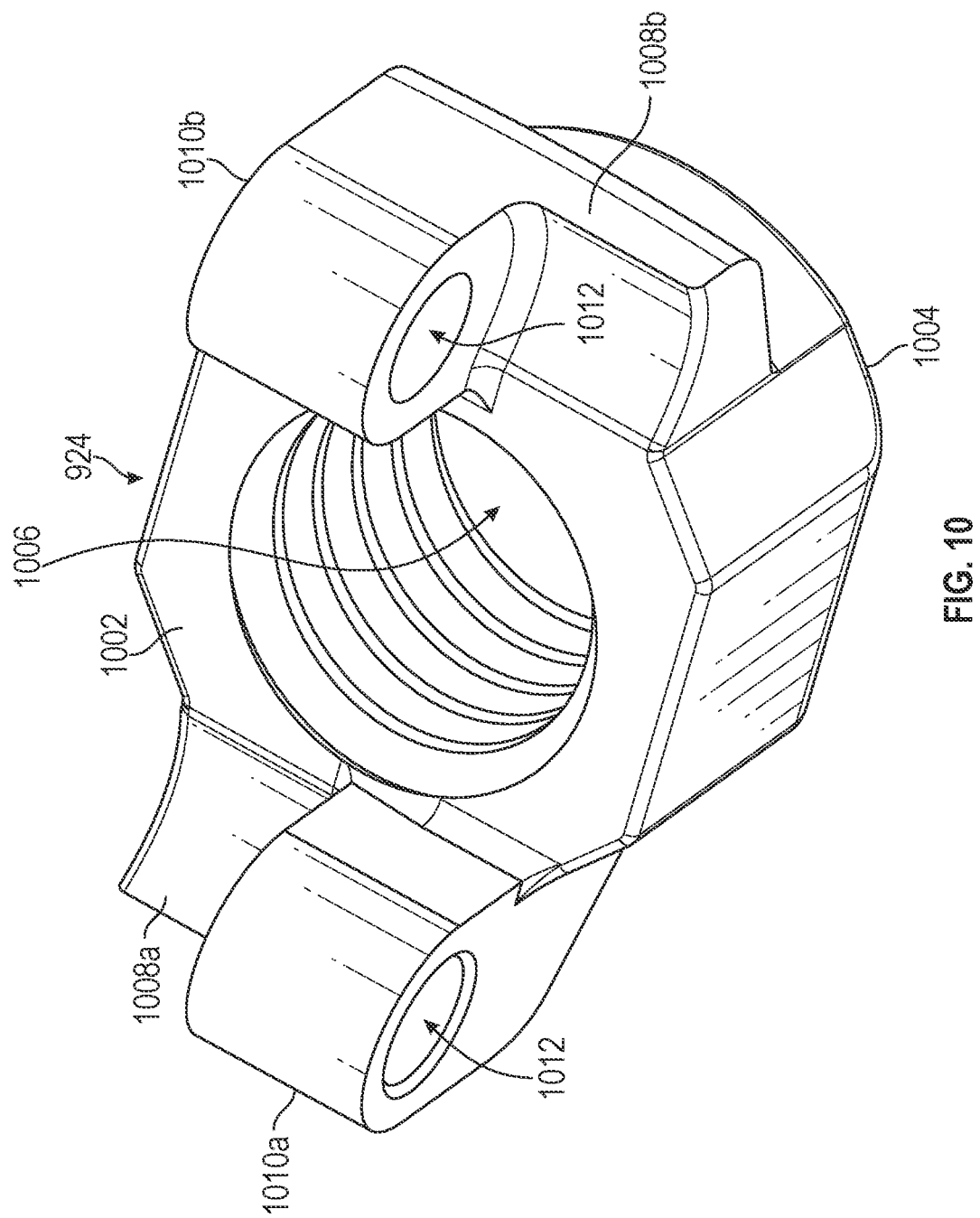

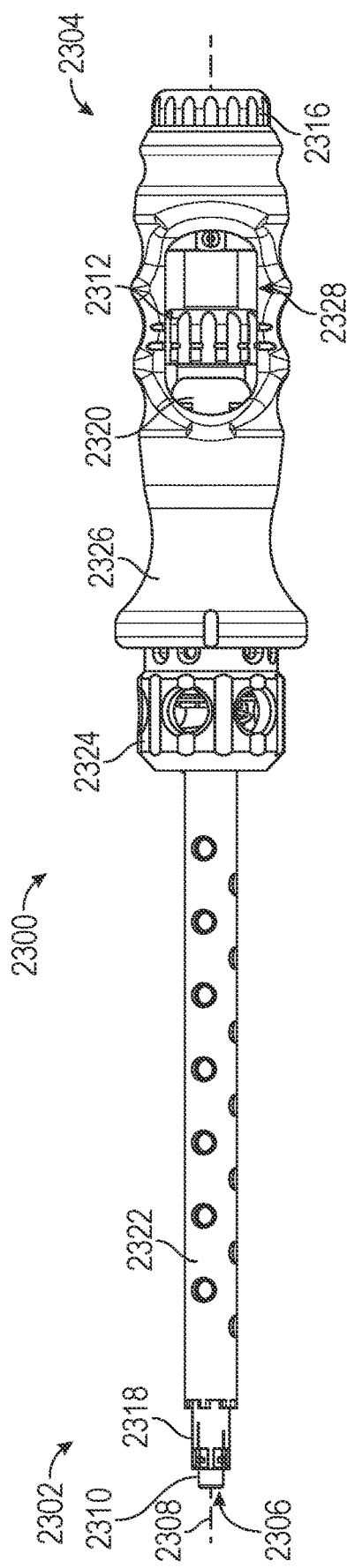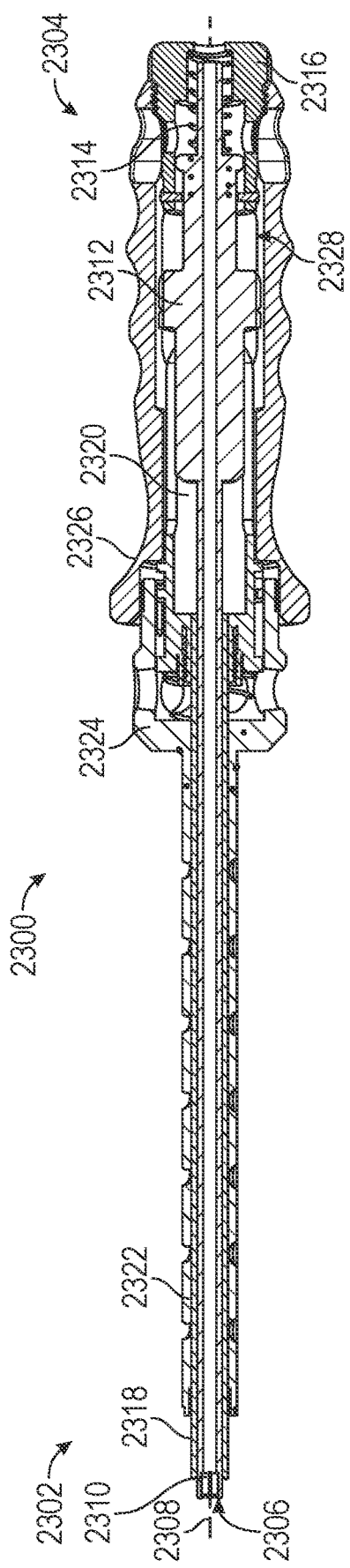
FIG. 23A
FIG. 23B

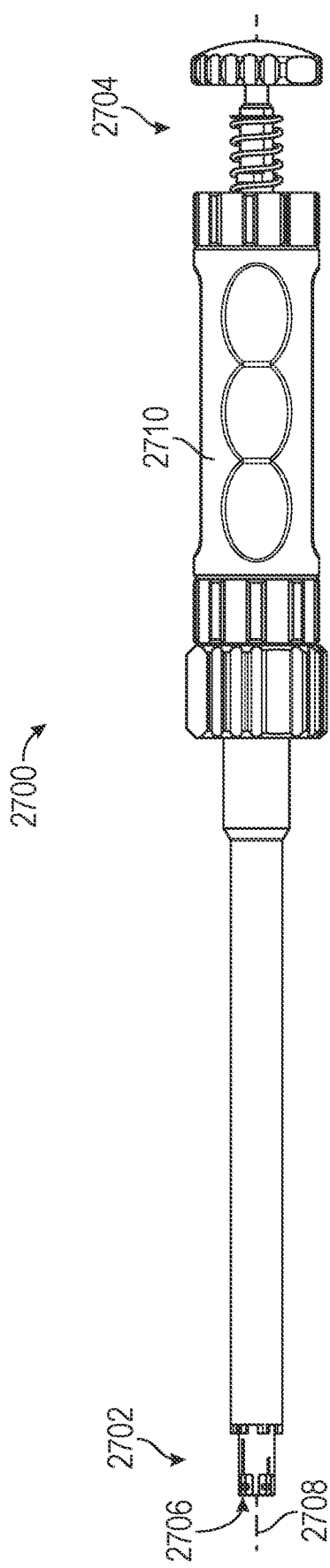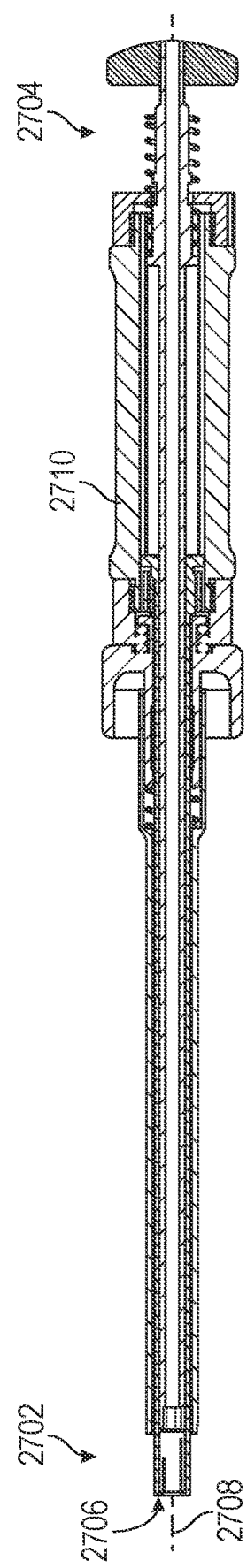
FIG. 27A
FIG. 27B

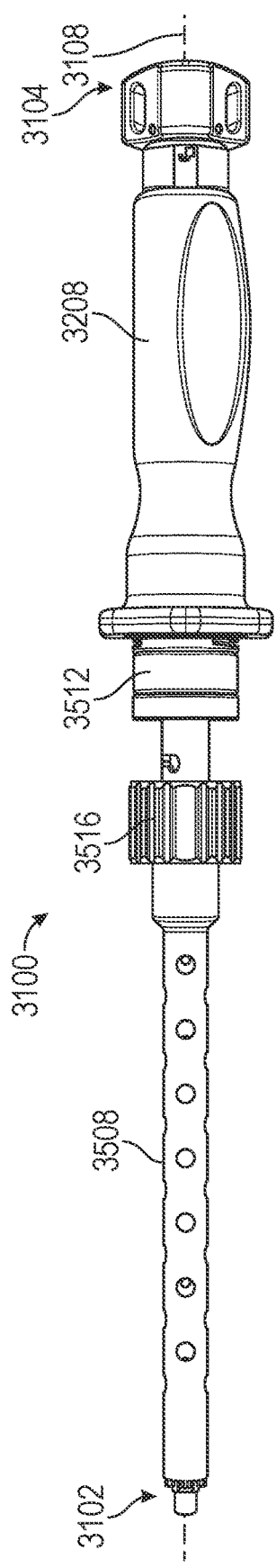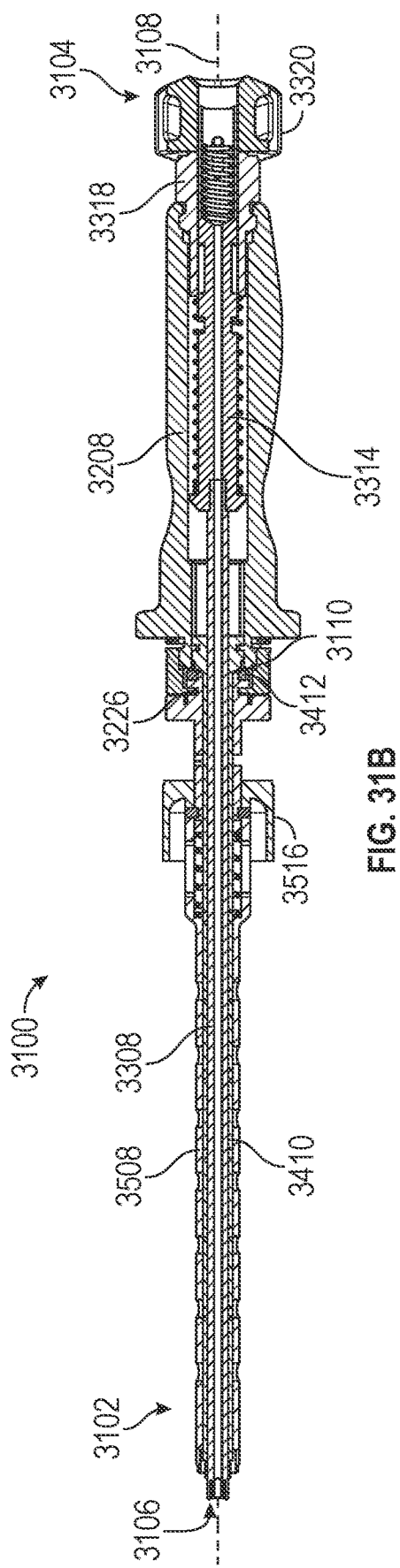
FIG. 31A
FIG. 31B

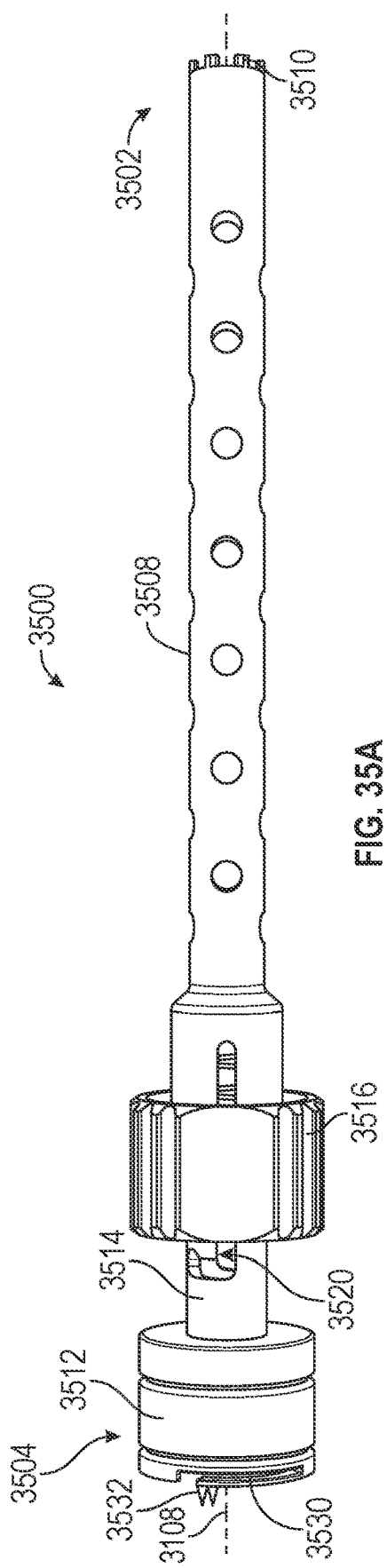
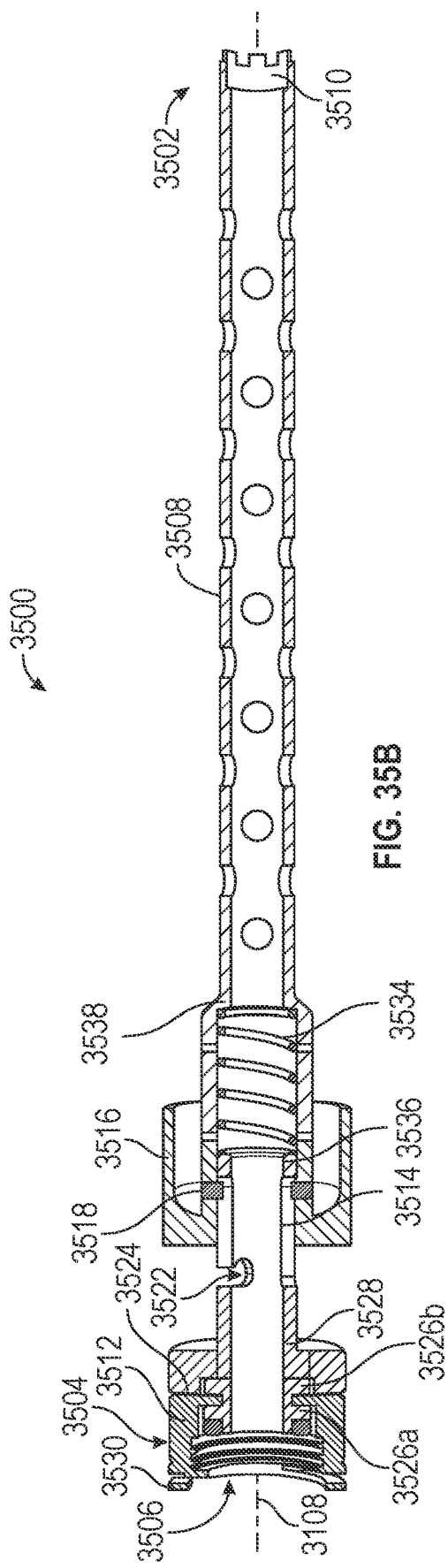

SACROILIAC JOINT FUSION IMPLANTS, INSERTION INSTRUMENTS, AND METHODS

CROSS-REFERENCE TO RELATED APPLICATIONS

This non-provisional patent application claims prior benefit, with regard to all subject matter, of U.S. Provisional Patent Application No. 63/576,430, filed Dec. 13, 2022, and entitled "SACROILIAC JOINT FUSION IMPLANTS AND METHODS"; and U.S. Provisional Patent Application No. 63/498,649, filed Apr. 27, 2023, and entitled "SACROILIAC JOINT FUSION IMPLANTS, INSERTION INSTRUMENTS, AND METHODS". The above-identified applications are hereby incorporated by reference in their entirety.

This non-provisional patent application shares certain common subject matter with U.S. application Ser. No. 18/504,635, filed Nov. 8, 2023, and entitled "SYSTEMS, METHODS, AND DEVICES FOR LATERAL AND POSTERIOR SACROILIAC JOINT FUSION." The above-identified application is hereby incorporated by reference in its entirety.

TECHNICAL FIELD

Embodiments of the present disclosure generally relate to systems, devices, and methods for spinal procedures. More specifically, embodiments of the present disclosure relate to systems, devices, and methods for fusion and stabilization of the sacroiliac joint.

RELATED ART

The spine consists of a column of twenty-four vertebrae that extends from the skull to the hips. The most inferior lumbar vertebra (L5) connects to the sacrum, which is a large bone that is formed by the fusion of the sacral vertebrae. On each side of the sacrum is an ilium, and the sacrum articulates with each ilium to form two sacroiliac (SI) joints. The SI joints play a significant role in absorbing impact from walking, lifting, and other movements.

When the ligaments or bony surfaces are damaged (e.g., due to trauma, arthritis, or other conditions), the SI joints can be a source of intense pain that can radiate into the leg. Inflammation in the SI joints is known as sacroiliitis. Sacroiliitis can be treated via non-surgical and surgical methods. Sacroiliitis may be treated surgically via an SI joint fusion procedure that uses an implant device to provide stability. The SI joints experience significant micromotions that make SI joint fusion difficult. Causing compression across the SI joint can reduce these micromotions; however, typical SI joint fusion devices fail to provide adequate compression across the SI joint to enhance fusion of the joint. Typical SI joint implants that can be inserted over a guidewire lack moving mechanical components that are actuated once the implant is at the implantation site. Improvements in SI joint fusion devices are needed.

SUMMARY

In some aspects, the techniques described herein relate to an implant for insertion across a sacroiliac (SI) joint, including: a first body defining a longitudinal axis extending along a length of the first body and a lateral axis extending along a width of the first body, the first body including: a window extending laterally along the lateral axis of the first body; a distal end along the length of the first body; a threaded proximal end along the length of the first body; and a distal anchor selectively positioned in an open configuration and a closed configuration, the distal anchor including a first wing and a second wing, wherein the first wing and the second wing are housed within the window in the closed configuration, and wherein the first wing and the second wing are deployed at least partially external from the window in the open configuration; a second body coupled to the threaded proximal end, the second body including a proximal anchor disposed on an outer surface of the second body, wherein the second body is configured to be threaded along the threaded proximal end to adjust an overall length of the implant, thereby adjusting an amount of compression across the SI joint.

In some aspects, the techniques described herein relate to an implant, further including: a plunger received within the first body, the plunger coupled to the first wing and the second wing, wherein longitudinal distal movement of the plunger deploys the first wing and the second wing at least partially external from the window.

In some aspects, the techniques described herein relate to an implant, further including: a first linkage including a first outer end and a first inner end; a second linkage including a second outer end and a second inner end, wherein the first linkage is coupled to the first wing at the first outer end and the second linkage is coupled to the second wing at the second outer end; and a pin coupling the first wing to the second wing via the first inner end and the second inner end to form a first pivot point such that the longitudinal distal movement of the plunger causes the first linkage and the second linkage to pivot about the first pivot point to transition the distal anchor from the closed configuration to the open configuration.

In some aspects, the techniques described herein relate to an implant, wherein the distal end of the first body includes an externally threaded portion and a non-threaded portion, the non-threaded portion disposed proximally from the externally threaded portion, and wherein the non-threaded portion includes one or more openings for receiving bone graft.

In some aspects, the techniques described herein relate to an implant, wherein a proximal end of the second body includes a bore extending along the longitudinal axis, and wherein an inner surface of the proximal end includes a shape configured to couple with an instrument configured to rotate the second body along the threaded proximal end of the first body.

In some aspects, the techniques described herein relate to an implant, wherein the distal end of the first body includes a blunt distal tip, the blunt distal tip defining an opening.

In some aspects, the techniques described herein relate to an implant, wherein the distal end includes one or more fenestrations proximal to the opening to self-harvest bone.

In some aspects, the techniques described herein relate to an implant, wherein at least one of the first wing or the second wing includes a generally flat surface configured to anchor against a cortical bone of a sacrum, wherein when the implant is in the open configuration, the implant is configured to be retracted proximally to anchor the first wing and the second wing against the cortical bone.

In some aspects, the techniques described herein relate to an implant for insertion across a sacroiliac (SI) joint, including: a first body defining a longitudinal axis extending along a length of the first body and a lateral axis extending along a width of the first body, the first body including: a window extending laterally along the lateral axis of the first body; a distal anchor having an open configuration and a closed configuration, the distal anchor including a first wing and a second wing, wherein the first wing and the second wing are housed within the window in the closed configuration, and wherein the first wing and the second wing are deployed at least partially external from the window in the open configuration; a second body including a proximal anchor disposed on an outer surface of the second body, wherein the proximal anchor includes a compressive element; and a threaded body including a distal end and a proximal end, the threaded body coupled to the first body at the distal end and to the second body at the proximal end, wherein the second body is configured to be threaded along the threaded body to adjust an overall length of the implant, thereby adjusting an amount of compression across the SI joint.

In some aspects, the techniques described herein relate to an implant, further including: a plunger received within the first body, wherein the plunger is coupled to the first wing and to the second wing, and wherein longitudinal distal movement of the plunger transitions the first wing and the second wing from the closed configuration to the open configuration.

In some aspects, the techniques described herein relate to an implant, wherein the threaded body is configured to be advanced distally within the first body to abut against a proximal end of the plunger to hold the first wing and the second wing in the open configuration.

In some aspects, the techniques described herein relate to an implant, wherein the first wing includes a first slot therethrough and the second wing include a corresponding second slot therethrough, and wherein the implant further includes: a fixed pin extending through the first body and received in the first slot and the second slot, wherein when the plunger is advanced distally, the first slot and the second slot move along the fixed pin such that a first curvature of the first slot defines a first travel path of the first wing, and a second curvature of the second slot defines a second travel path of the second wing.

In some aspects, the techniques described herein relate to an implant, wherein the first curvature of the first slot is configured to deploy the first wing along a first path that is tangent to a first curve formed by the first wing in the closed configuration, and wherein the second curvature of the second slot is configured to deploy the second wing along a second path that is tangent to a second curve formed by the second wing in the closed configuration.

In some aspects, the techniques described herein relate to an implant, wherein the first body further includes: an externally threaded distal end, a proximal end of the first body, and a central section therebetween, and wherein at least one flute extends along the externally threaded distal end and the central section.

In some aspects, the techniques described herein relate to an implant, wherein the second body defines a longitudinal bore, the longitudinal bore having an exterior surface configured to be engaged by an instrument to rotate and thread the second body along the threaded body.

In some aspects, the techniques described herein relate to an implant, wherein the compressive element is a polyaxial washer.

In some aspects, the techniques described herein relate to a method for fusion and stabilization of a sacroiliac (SI) joint, including: providing instructions for inserting an implant across the SI joint, the instructions including: make a minimally invasive incision on a patient to provide access to the SI joint of the patient; dilate soft tissue of the patient by sequentially advancing dilators over a guide wire, each sequential dilator having a larger width than a previous dilator; insert the implant through the minimally invasive incision, through an ilium, through the SI joint, and into a sacrum of the patient, wherein the implant includes: a first body having a distal anchor including a pair of deployable wings; and a second body having a proximal anchor including a compressive element; deploy the pair of deployable wings; and advance the second body distally to anchor the compressive element and cause compression across the SI joint.

In some aspects, the techniques described herein relate to a method, wherein the instructions further include: prior to advancing the second body distally, retracting the implant proximally to anchor the pair of deployable wings against cortical bone of the sacrum.

In some aspects, the techniques described herein relate to a method, wherein the implant defines a central bore extending therethrough and further includes: a plunger received within the central bore and coupled to the pair of deployable wings, the plunger including internal threads, and wherein deploying the pair of deployable wings includes: engaging the internal threads with an instrument; and rotating the instrument to advance the plunger distally, thereby deploying the pair of deployable wings.

In some aspects, the techniques described herein relate to a method, wherein the implant further includes one or more slots, and wherein the instructions further include: prior to inserting the implant, adding bone graft into the one or more slots.

In some embodiments, the techniques described herein relate to an implant for insertion across a sacroiliac (SI) joint, including: a main body defining a longitudinal axis extending along a length of the main body and a lateral axis extending along a width of the main body, the main body including: a window extending laterally along the lateral axis of the main body; a distal end along the length of the main body and including a distal anchor having an open configuration and a closed configuration, the distal anchor including a first wing and a second wing, wherein the first wing and the second wing are housed within the window in the closed configuration, and wherein the first wing and the second wing are deployed at least partially external from the window in the open configuration; and a threaded proximal end along the length of the main body; a compressive body coupled to the threaded proximal end, the compressive body forming a proximal anchor for the implant, wherein the compressive body is configured to be threaded along the threaded proximal end to adjust an overall length of the implant, thereby adjusting an amount of compression across the SI joint; and a cannula extending along the longitudinal axis.

In some embodiments, the techniques described herein relate to an implant, further including: a plunger received within the main body, the plunger coupled to the first wing and the second wing, wherein longitudinal distal movement of the plunger deploys the first wing and the second wing at least partially external from the window.

In some embodiments, the techniques described herein relate to an implant, wherein the compressive body includes teeth configured to engage with an ilium.

In some embodiments, the techniques described herein relate to an implant, wherein the first wing includes a first offset portion and the second wing includes a second offset portion, and wherein the first offset portion and the second offset portion define an opening therebetween when the distal anchor is in the closed configuration such that the cannula is unobstructed entirely along the length of the implant.

In some embodiments, the techniques described herein relate to an implant, wherein the distal end of the main body includes threads and flutes for self-drilling the implant.

In some embodiments, the techniques described herein relate to an implant, wherein the first wing includes a first slot, wherein a first pin is fixed to the main body and received within the first slot, and wherein the first wing rides along the first pin when moving between the open configuration and the closed configuration.

In some embodiments, the techniques described herein relate to an implant, wherein the second wing includes a second slot, wherein a second pin is fixed to the main body and received within the second slot, and wherein the second wing rides along the second pin when moving between the open configuration and the closed configuration.

In some embodiments, the techniques described herein relate to an implant, wherein at least one of the first wing or the second wing includes one or more fangs configured to engage with cortical bone of a sacrum, wherein when the implant is in the open configuration, the implant is configured to be retracted proximally to anchor the first wing and the second wing against the cortical bone.

In some embodiments, the techniques described herein relate to an implant for insertion across a sacroiliac (SI) joint, including: a main body defining a longitudinal axis extending along a length of the main body and a lateral axis extending along a width of the main body, the main body including: a window extending laterally along the lateral axis of the main body; a distal anchor having an open configuration and a closed configuration, the distal anchor including a first wing and a second wing, wherein the first wing and the second wing are housed within the window in the closed configuration, and wherein the first wing and the second wing are deployed at least partially external from the window in the open configuration; and a compressive body coupled to the main body and forming a proximal anchor for the implant, wherein the compressive body is adjustable along the main body to adjust an overall length of the implant, thereby adjusting an amount of compression across the SI joint.

In some embodiments, the techniques described herein relate to an implant, further including: a plunger received within the main body, wherein the plunger is coupled to the first wing and to the second wing, and wherein longitudinal distal movement of the plunger transitions the first wing and the second wing from the closed configuration to the open configuration.

In some embodiments, the techniques described herein relate to an implant, wherein the first wing includes a first slot therethrough and the second wing include a corresponding second slot therethrough, and wherein the implant further includes: a first pin coupled to the main body and received in the first slot and a second pin coupled to the main body and received in the second slot, wherein when the plunger is advanced distally, the first slot moves along the first pin and the second slot move along the second pin such that a first curvature of the first slot defines a first travel path of the first wing, and a second curvature of the second slot defines a second travel path of the second wing.

In some embodiments, the techniques described herein relate to an implant, wherein the first curvature of the first slot is configured to deploy the first wing along a first path that is tangent to a first curve formed by the first wing in the closed configuration, and wherein the second curvature of the second slot is configured to deploy the second wing along a second path that is tangent to a second curve formed by the second wing in the closed configuration.

In some embodiments, the techniques described herein relate to an implant, wherein the compressive body is threadedly engaged with a proximal end of the main body.

In some embodiments, the techniques described herein relate to an implant, wherein the compressive body includes one or more engaging features configured to be engaged by an insertion instrument to rotate and thread the compressive body along the proximal end of the main body.

In some embodiments, the techniques described herein relate to an implant, wherein the implant is cannulated along the longitudinal axis.

In some embodiments, the techniques described herein relate to an implant, wherein the main body includes a central, non-threaded section having a roughened outer surface to promote bony fusion.

In some embodiments, the techniques described herein relate to a method for fusion and stabilization of a sacroiliac (SI) joint, including: providing instructions for inserting an implant across the SI joint, the instructions including: make a minimally invasive incision on a patient to provide access to the SI joint of the patient; dilate soft tissue of the patient by sequentially advancing dilators over a guide wire, each sequential dilator having a larger width than a previous dilator; insert the implant through the minimally invasive incision, through an ilium, through the SI joint, and into a sacrum of the patient, wherein the implant includes: a first body having a distal anchor including a pair of deployable wings; and a second body having a proximal anchor including a compressive element; deploy the pair of deployable wings; and advance the second body distally to engage the compressive element with the ilium and cause compression across the SI joint.

In some embodiments, the techniques described herein relate to a method, wherein the instructions further include: prior to advancing the second body distally, retracting the implant proximally to anchor the pair of deployable wings against cortical bone of the sacrum.

In some embodiments, the techniques described herein relate to a method, wherein the implant defines a central bore extending therethrough and further includes: a plunger received within the central bore and coupled to the pair of deployable wings, the plunger including internal threads or a female hex, and wherein deploying the pair of deployable wings includes: engaging the internal threads or the female hex with an instrument; and rotating the instrument to advance the plunger distally, thereby deploying the pair of deployable wings.

In some embodiments, the techniques described herein relate to a method, wherein the instructions further include: fill the implant with bone graft through a central bore extending along a length of the implant. This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current present disclosure will be apparent from the following detailed description of the embodiments and the accompanying drawing figures.

BRIEF DESCRIPTION OF THE FIGURES

Embodiments of the present disclosure are described in detail below with reference to the attached drawing figures, wherein:

FIG. 10 illustrates a plunger of the second embodiment;

FIG. 23A illustrates a perspective view of an insertion instrument for some embodiments;

FIG. 23B illustrates a cross-sectional view of the insertion instrument of for some embodiments;

FIG. 27A illustrates a second insertion instrument for some embodiments;

FIG. 27B illustrates a cross-sectional view of the second insertion instrument for some embodiments;

FIG. 31A illustrates a third insertion instrument for some embodiments;

FIG. 31B illustrates a cross-sectional view of the third insertion instrument for some embodiments;

FIG. 35A illustrates a compressive body driver subassembly of the third insertion instrument for some embodiments;

FIG. 35B illustrates a cross-sectional view of the compressive body driver for some embodiments;

Figure 1A:
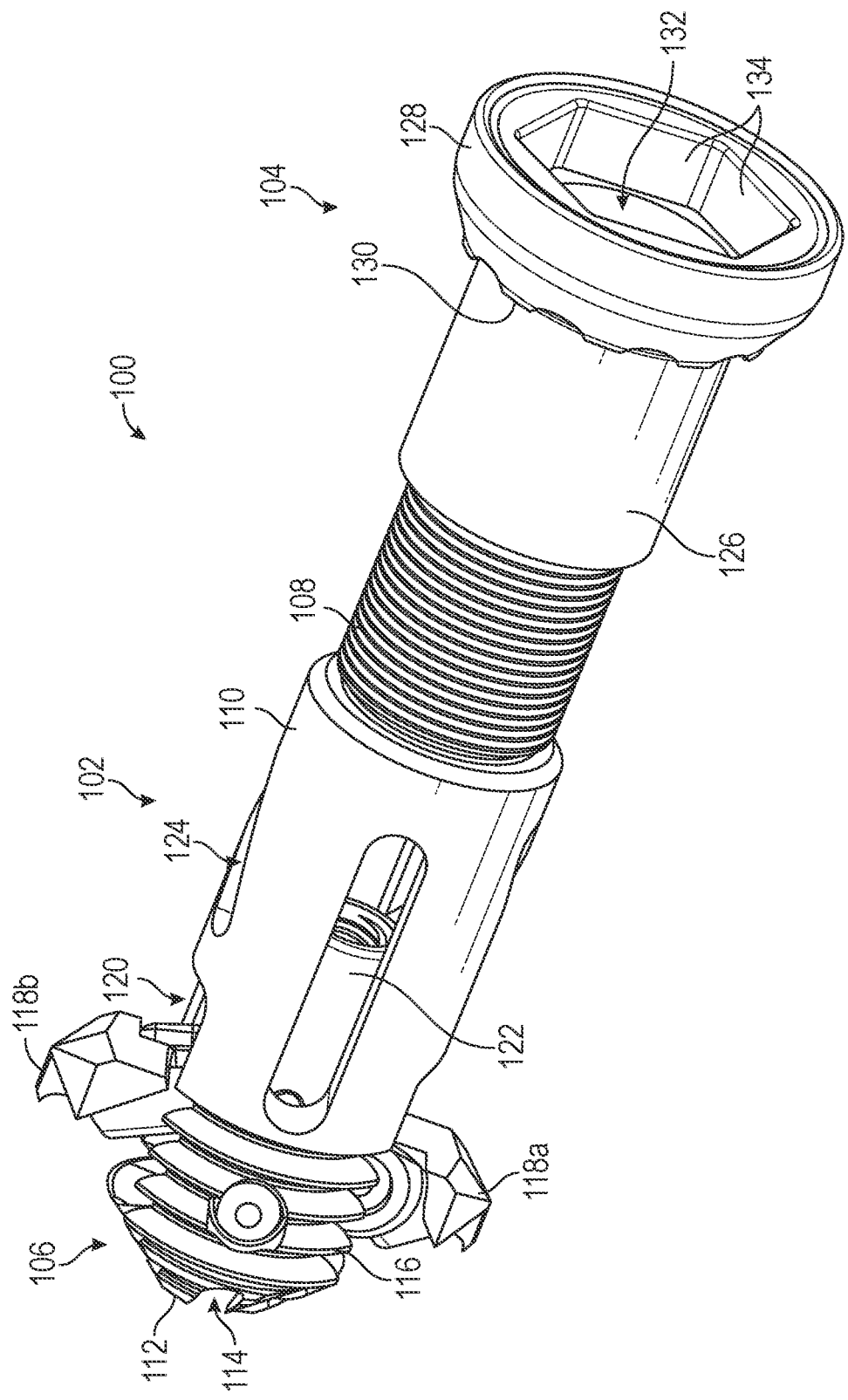
FIG. 1A illustrates an implant for insertion across the sacroiliac joint in an open configuration for some embodiments.

The drawing figures do not limit the present disclosure to the specific embodiments disclosed and described herein. The drawings are not necessarily to scale, emphasis instead being placed upon clearly illustrating the principles of the present disclosure.

DETAILED DESCRIPTION

The subject matter of the present disclosure is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be understood by one skilled in the art and are intended to be captured within the scope of the claims. Terms should not be interpreted as implying any particular ordering of various steps described unless the order of individual steps is explicitly described.

The following detailed description of embodiments of the present disclosure references the accompanying drawings that illustrate specific embodiments in which the present disclosure can be practiced. The embodiments are intended to describe aspects of the present disclosure in sufficient detail to enable those skilled in the art to practice the present disclosure. Other embodiments can be utilized and changes can be made without departing from the scope of the present disclosure. The following detailed description is, therefore, not to be taken in a limiting sense. The scope of embodiments of the present disclosure is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate reference to "one embodiment" "an embodiment", or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments but is not necessarily included. Thus, the technology can include a variety of combinations and/or integrations of the embodiments described herein.

Embodiments of the present disclosure are generally directed to systems, devices, and methods for stabilization and fusion of the sacroiliac (SI) joint. The SI joint is located between the ilium and the sacrum in the pelvic region of the body. An implant may be inserted laterally across the SI joint such that the implant passes into and through the ilium, across the SI joint, and into the sacrum. The ilium comprises an outer cortical bone region, an inner cortical bone region that is adjacent to the SI joint, and a cancellous bone (also called trabecular bone) region between the outer and inner cortical bone regions. Likewise, the sacrum comprises an outer cortical bone region adjacent to the SI joint, an inner cortical bone region, and a cancellous bone region between the outer and inner cortical bone regions. Medial from the inner cortical bone region of the sacrum are critical vascular structures of the body. When inserted, the implant may be placed through the ilium and the SI joint and into the cancellous bone of the sacrum, but not through the interior cortical bone of the sacrum to protect the critical vascular structures on the other side of the interior cortical bone. The implant may be placed in or proximal to the S1 vertebra of the sacrum.

The implant may be inserted via a minimally invasive incision. A minimally invasive incision may comprise an incision of less than about 2 inches, in contrast to traditional open surgeries having five to six inch incisions. Minimally invasive surgeries allow for muscle to be distracted as opposed to cut away as in open surgeries, which allows for quicker recoveries, reduced blood loss, and hospital stay, among other benefits.

In some embodiments, the implant comprises a first or distal body and a second or proximal body. The first body may comprise a distal anchor formed by a pair of deployable wings configured to anchor within the sacrum, and the second body may comprise a proximal anchor formed by a compressive element configured to anchor against the ilium. The distal anchor and the proximal anchor may cause compression across the SI joint. The second body may be connected to the first body via a threaded body which, in some embodiments, is integral with the first body, and, in other embodiments, is not integral with the first body, such as, for example, being removably separable from the first body. The second body may be moved along the threaded body to adjust an overall length of the implant. As the second body is moved distally along the threaded body and the length of the implant decreases, compression is added to the SI joint. In some embodiments, a central, longitudinal bore extends through the implant and provides an opening through which bone graft may be delivered after insertion of the implant. The longitudinal bore further allows for the implant to be placed over a guidewire for inserting the implant into the patient. Adding compression to the SI joint can improve fusion and stabilization of the joint by reducing the micromotions in the joint. In some embodiments, one or more implants are inserted across the SI joint.

First Implant Embodiment

Figure 1B:
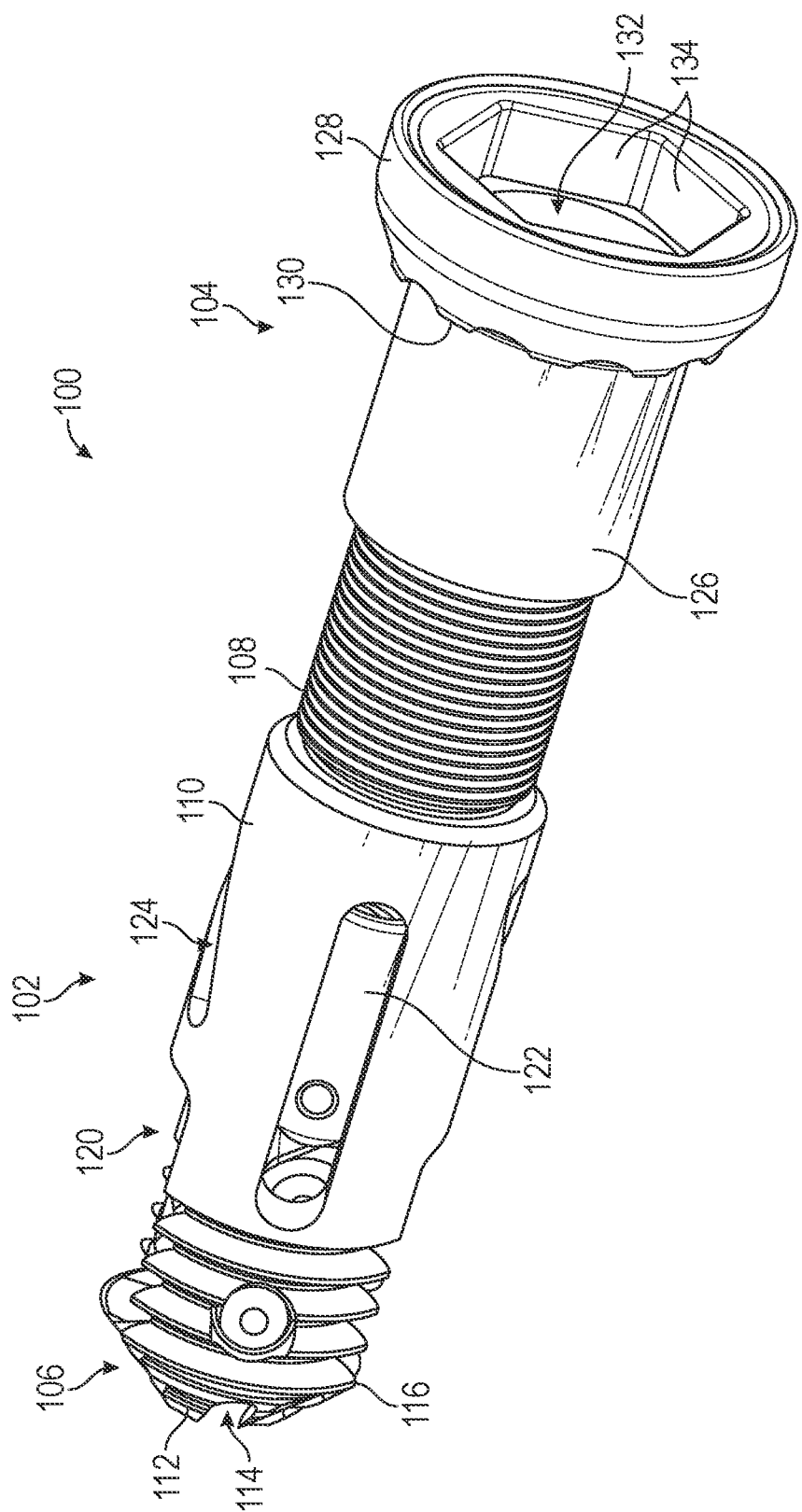
FIG. 1B illustrates the implant in a closed configuration for some embodiments.

FIG. 1A illustrates an implant 100 in an open configuration, and FIG. 1B illustrates implant 100 in a closed configuration for some embodiments. Implant 100 may be configured to be inserted across the SI joint for fusion and stabilization of the joint. Implant 100 may comprise a distal or first body 102 and a proximal or second body 104. First body 102 may have a length extending along a longitudinal axis, a width extending along a lateral axis, a distal end 106 at one end of the length, a proximal end 108 at an opposing end of the length, and a central section 110 disposed between distal end 106 and proximal end 108. The distal end 106 may include a distal tip 112. In some embodiments, distal tip 112 is substantially conical. In some embodiments, distal tip 112 is substantially blunt or rounded. By providing a blunt distal tip, the likelihood that implant 100, when inserted, will pierce the innermost layer of cortical bone in the sacrum is reduced, thereby protecting the critical vascular structures that are medial therefrom.

In some embodiments, distal tip 112 is formed with one or more openings to promote self-harvesting of bone when inserting implant 100 into the patient. In some embodiments, distal tip 112 comprises one or more fenestrations 114 that are configured to self-harvest bone. In some embodiments, fenestrations 114 are formed as substantially U-shaped openings. In some embodiments, the number of fenestrations 114 is two or four. In some embodiments, fenestrations 114 are spaced at substantially even intervals around distal tip 112 (e.g., in intervals of 45°, 90°, 180°, etc.). The fenestrations of implant 100 may promote bony fusion of the SI joint. In some embodiments, distal tip 112 is solid.

Distal end 106 may comprise external threads 116 along at least a portion thereof. In some embodiments, threads 116 are helical threads. Additionally, or alternatively, the external threads 116 may be cutting threads or box threads. In some embodiments, threads 116 may comprise a depth of about 0.5 mm to about 3.0 mm, an angle of about 45° to about 100°, and a spacing of about 1.0 mm to about 4.0 mm. Other thread dimensions may be used without departing from the scope hereof. In some embodiments, threads 116 are formed with one or more flat surfaces or "flats" that aid in inserting implant 100 into the sacrum.

First body 102 may also comprise a first wing 118a and a second wing 118b. Wings 118a, 118b may be housed within a window 120 formed in first body 102. In some embodiments, window 120 is substantially rectangular. In some embodiments, window 120 extends laterally from a first side of implant 100 to a second side of implant 100. Wings 118a, 118b may be deployable out of window 120 to transition implant 100 from the closed configuration (FIG. 1B) to the open configuration (FIG. 1A). When implant 100 is inserted into a patient, implant 100 may be in the closed configuration. When implant 100 is at the desired position where wings 118a, 118b can be deployed into the cancellous bone of the sacrum, wings 118a, 118b may be deployed to transition implant 100 to the open configuration. Wings 118a, 118b may be coupled to a plunger 122 that is housed within first body 102. Plunger 122 may comprise internal threads (FIG. 2) that can be engaged by an insertion tool. The insertion tool may advance plunger 122 distally to deploy wings 118a, 118b out of window 120. Proximal movement of plunger 122 may retract wings 118a, 118b back within window 120.

Central section 110 may extend proximally from distal end 106 and may comprise a non-threaded portion. In some embodiments, central section 110 comprises a substantially smooth outer surface. In some embodiments, central section 110 comprises a rough outer surface to promote bony fusion. Alternatively, or additionally, 110 may be coated with a material (e.g., hydroxyapatite) to promote bony fixation. As discussed further below, after wings 118a, 118b are deployed, the implant 100 may be pulled proximally to anchor wings 118a, 118b to the cortical bone of the sacrum. Providing a non-threaded central section 110 aids in pulling the implant 100 proximally as compared to having an externally threaded body as the threads would thread into the surrounding bone, which would cause a resisting force when retracting implant 100. In some embodiments, central section 110 comprises one or more openings 124 in which bone graft may be added to promote bony fusion. Openings 124 may also aid in self-harvesting bone during insertion of implant 100. In some embodiments, central section 110 comprises two opposing openings 124 that extend longitudinally along central section 110, and two opposing openings 124 that are oriented at an angle. Openings 124 may take various geometries. As shown, openings 124 are stadium-shaped; however, openings 124 may instead be rectangular, ovular, circular, or any other shape. Openings 124 may be oriented in any direction, such as laterally, longitudinally, or diagonally across the outer surface of central section 110. In some embodiments, central section 110 is solid without any openings 124.

Central section 110 transitions into proximal end 108. In some embodiments, proximal end 108 is integral with first body 102. In some embodiments, proximal end 108 comprises external threads that are configured to mate with an outer sleeve 126 of second body 104. Outer sleeve 126 may comprise internal threads configured to mate with the external threads on proximal end 108. Thus, second body 104 may be threaded along proximal end 108 to adjust a length of implant 100, thereby applying compression to the SI joint. The amount of compression may be adjusted by adjusting the position of second body 104 on proximal end 108. Longitudinal distal movement of second body 104 may increase the compression provided by implant 100, while longitudinal proximal movement of second body 104 may reduce the compression provided by implant 100. In some embodiments, central section 110 and outer sleeve 126 comprise substantially the same diameter, and proximal end 108 comprises a smaller diameter than central section 110 and outer sleeve 126. Thus, if second body 104 is threaded along the entire length of proximal end 108 to provide compression across the SI joint, as shown in FIG. 1B, central section 110 and outer sleeve 126 may be substantially flush.

In some embodiments, proximal end 108 comprises a length of about 10 mm to about 20 mm. In some embodiments, proximal end 108 comprises a length of about 15 mm. The length of proximal end 108 may define an adjustment length of implant 100. Implant 100 may have a minimum length defined as a length of the implant 100 when second body 104 is threaded distally as far as possible along proximal end 108. The minimum length of implant 100, therefore, may correspond to a length at which a maximum amount of compression is applied to the SI joint. Likewise, implant 100 may have a maximum length defined as a length of the implant 100 when second body 104 is threaded proximally as far as possible along proximal end 108. The maximum length of implant 100, therefore, may correspond to a length at which a minimum amount of compression is applied to the SI joint. In some embodiments, the minimum length of implant 100 is about 25 mm to about 35 mm. In some embodiments, the maximum length of implant 100 is about 60 mm to about 70 mm. In some embodiments, the maximum length of implant 100 is about 70 mm to about 120 mm. The length at which implant 100 is set during implantation may depend on the anatomy of the patient, and implant 100 may take any suitable length based on the anatomy of the patient.

In some embodiments, a compressive element 128 is received on an outer surface of outer sleeve 126 and may be configured to anchor against the ilium. Compressive element 128 may add additional compression to the SI joint, along with the compression provided by wings 118a, 118b and adjusting the length of implant 100. In some embodiments, the compressive element 128 is a washer or a nut. Compressive element 128 may be substantially rigid. In some embodiments, compressive element 128 comprises one or more engagement features 130 for engaging with the ilium. For example, one or more engagement features 130 may comprise prongs, fangs, teeth, ridges, bumps, or other like features that engage or embed with the ilium to help anchor compressive element 128 thereto.

Second body 104 may define a bore 132 that extends longitudinally therethrough. In some embodiments, a longitudinal bore extends through the entirety of implant 100. For example, when distal tip 112 is formed with an opening, a bore may extend from second body 104 and through first body 102. When distal tip 112 is solid, the bore may extend from second body 104 and terminate at distal tip 112. Thus, a tool may be inserted through the bore 132 to drive plunger 122 for deployment of wings 118a, 118b. A proximal end of bore 132 may have a particular shape to receive a device configured to rotate second body 104 about proximal end 108. For example, as shown, the proximal end of 132 is hexagonal, having six inner walls 134 and is configured to be engaged by a hex driver that can rotate second body 104. Other shapes and configurations for receiving other driving tools are within the scope hereof. The proximal end of bore 132 may be formed with detents or other features to lock the driver tool therein.

Figure 2:
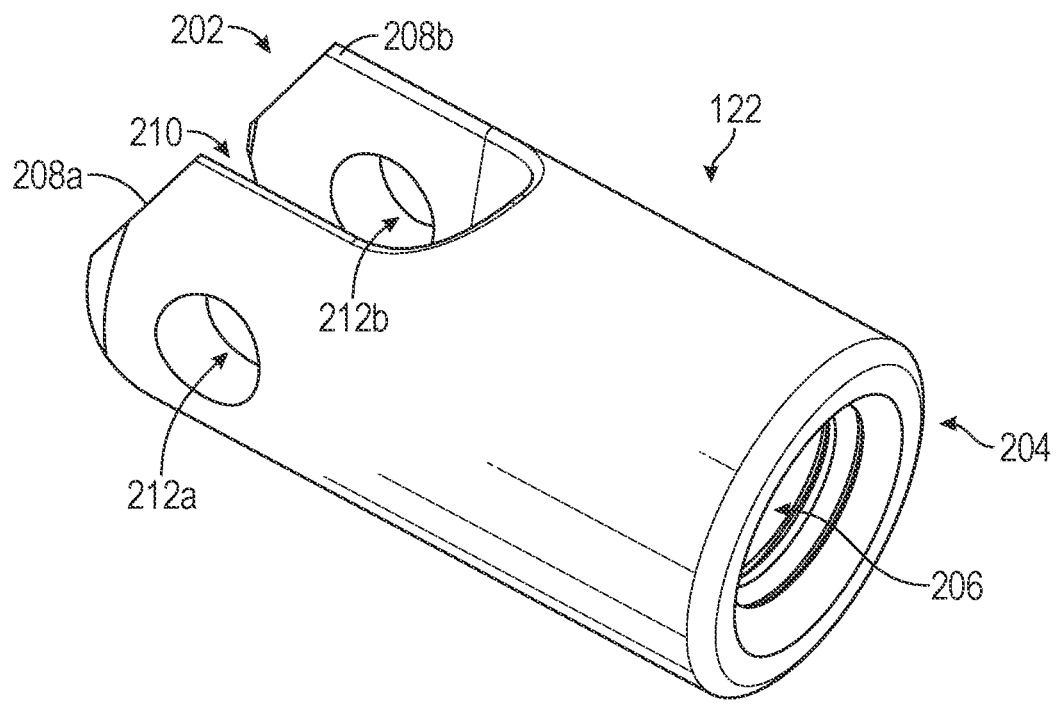
FIG. 2 illustrates a plunger of the implant for some embodiments.

FIG. 2 illustrates plunger 122 for some embodiments of the present disclosure. In some embodiments, plunger 122 has a distal end 202 and a proximal end 204. Plunger 122 can be moved longitudinally within first body 102 to open and close wings 118a, 118b as mentioned previously. In some embodiments, proximal end 204 has a central bore 206 in which a threaded inserter device (not shown) can be received. Central bore 206 may comprise internal threading configured to mate with the inserter device. Thus, the inserter device may threadedly engage with plunger 122 to move plunger 122 longitudinally. Other methods of driving plunger 122 may be employed without departing from the scope hereof. Additionally, central bore 206 provides an opening through which bone graft may be added after deployment of wings 118a, 118b into the cancellous bone of the sacrum.

In some embodiments, plunger 122 is substantially Y-shaped with a first arm 208a and a second arm 208b defining an opening 210 therebetween. First arm 208a may define a first opening 212a that is substantially in-line with a second opening 212b in second arm 208b. An inner end of wings 118a, 118b may be received within opening 210, and a pin (see FIGS. 5A and 5B) may be inserted through first opening 212a, through the inner end of first wing 118a, the inner end of second wing 118b, and through second opening 212b to couple wings 118a, 118b to plunger 122.

Figure 3:
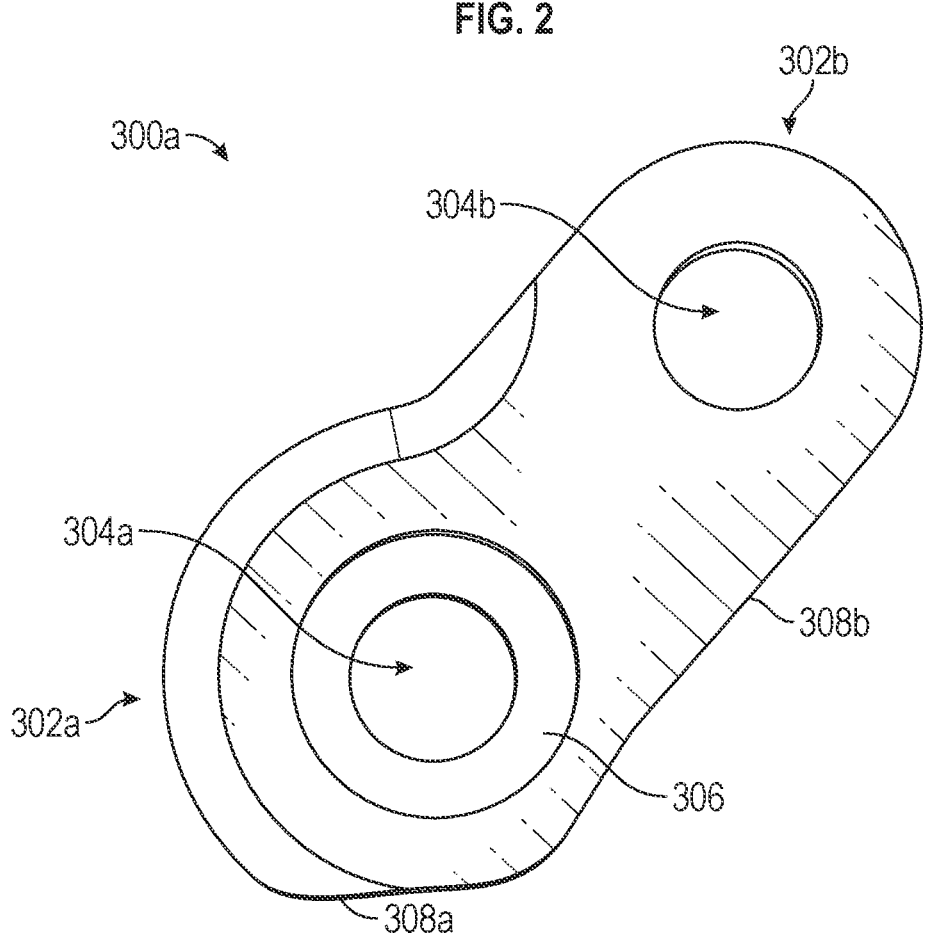
FIG. 3 illustrates a linkage of the implant for some embodiments.
Figure 5A:
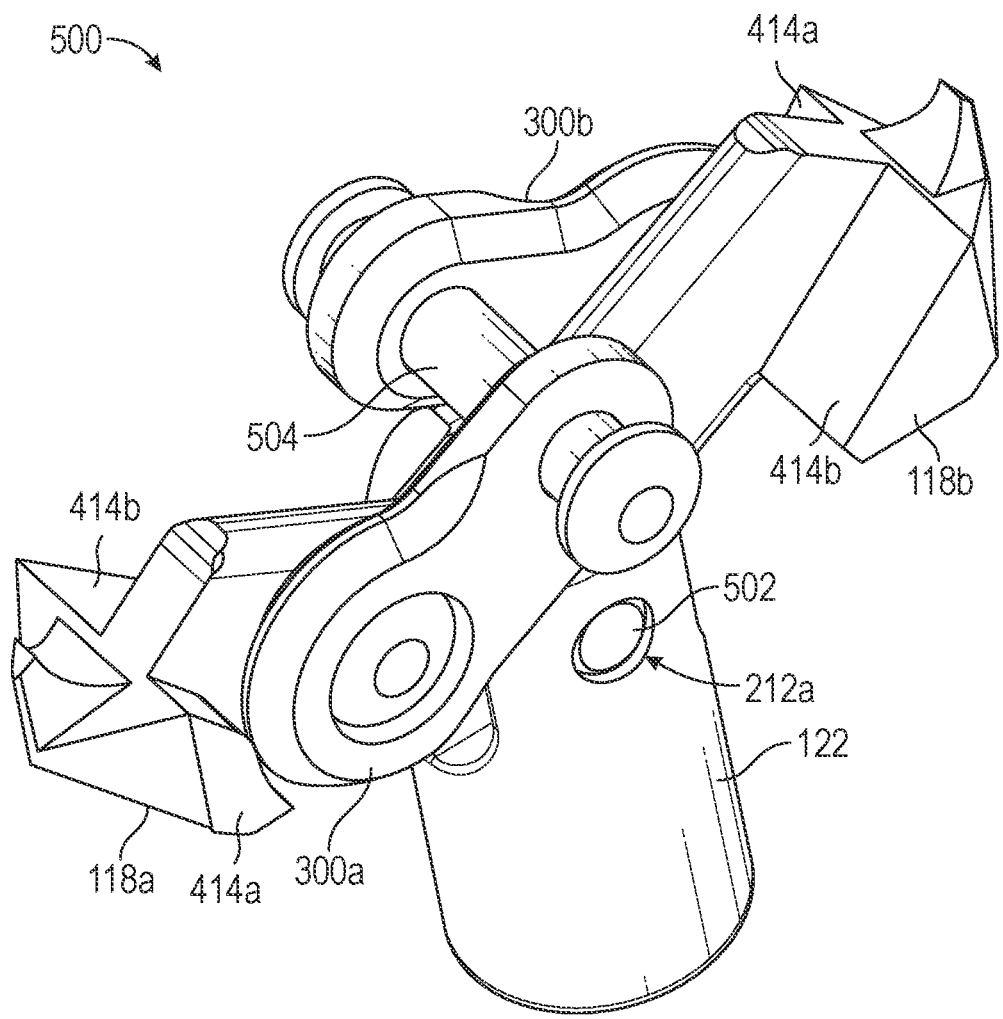
FIG. 5A illustrates a wing assembly of the implant in the open configuration for some embodiments.
Figure 5B:
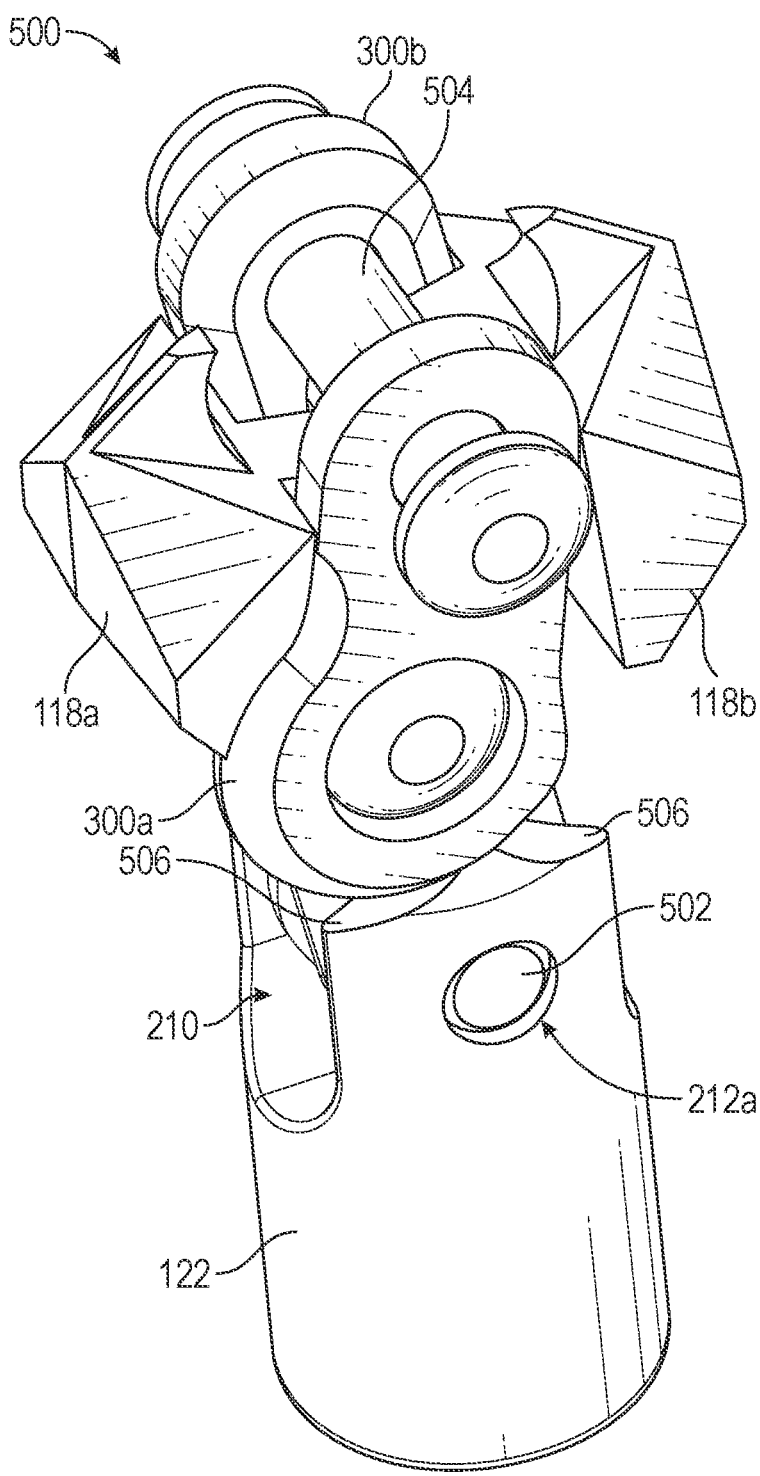
FIG. 5B illustrates the wing assembly in the closed configuration for some embodiments.

FIG. 3 illustrates a first linkage 300a for some embodiments of the present disclosure. As shown in FIGS. 5A and 5B, first linkage 300a may operatively connect first wing 118a to second wing 118b via a second linkage 300b. Second linkage 300b may be substantially similar to first linkage 300a.

First linkage 300a may comprise a first end 302a and a second end 302b. First end 302a may have a first opening 304a, and second end 302b may have a second opening 304b. First opening 304a may be configured to couple to a connecting member on first wing 118a to couple first linkage 300a thereto. First end 302a may comprise a recessed surface 306 concentric with first opening 304a in which a cap may be placed to secure the first linkage 300a to wings 118a. Second opening 304b may be configured to receive a pin (FIGS. 5A and 5B) that is inserted through a corresponding second opening 304b on first linkage 300a to connect first wing 118a to second wing 118b.

In some embodiments, first linkage 300a comprises a first edge 308a and a second edge 308b. In some embodiments, edges 308a, 308b are substantially flat. When wings 118a, 118b are in the closed configuration, first edge 308a may abut or be proximal to a top surface of first arm 208a on plunger 122 (see FIG. 5B). As plunger 122 is advanced distally, the top surface may push against first edge 308a and rotate first linkage 300a. When first linkage 300a rotates, the top surface of first arm 208a may push against second edge 308b to continue driving the rotation of first linkage 300a, thereby deploying first wing 118a out of window 120.

Figure 4A:
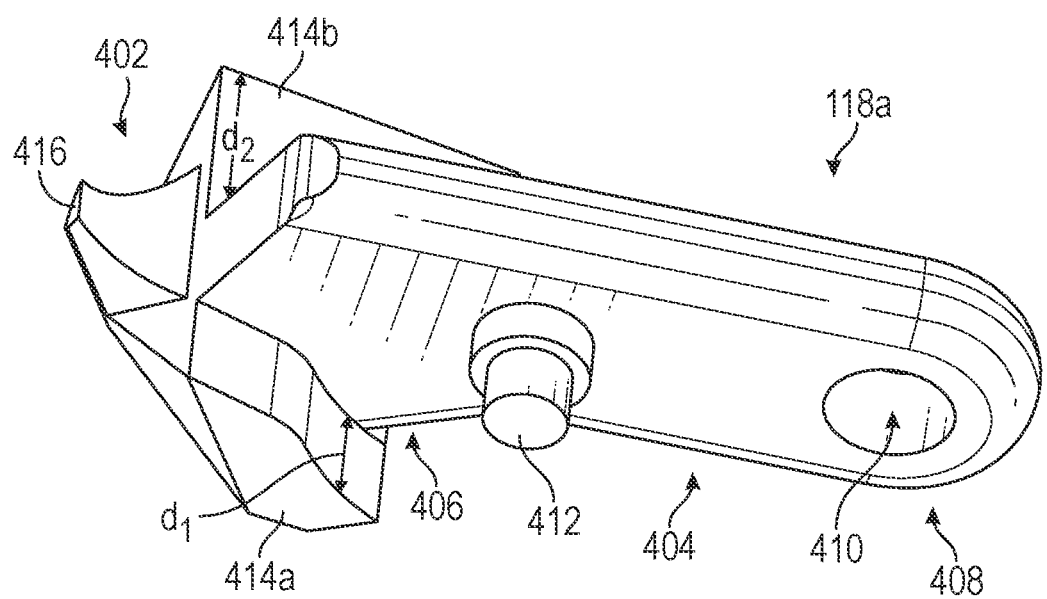
FIGS. 4A, 4B, and 4C illustrate a wing of the implant for some embodiments.
Figure 4B:
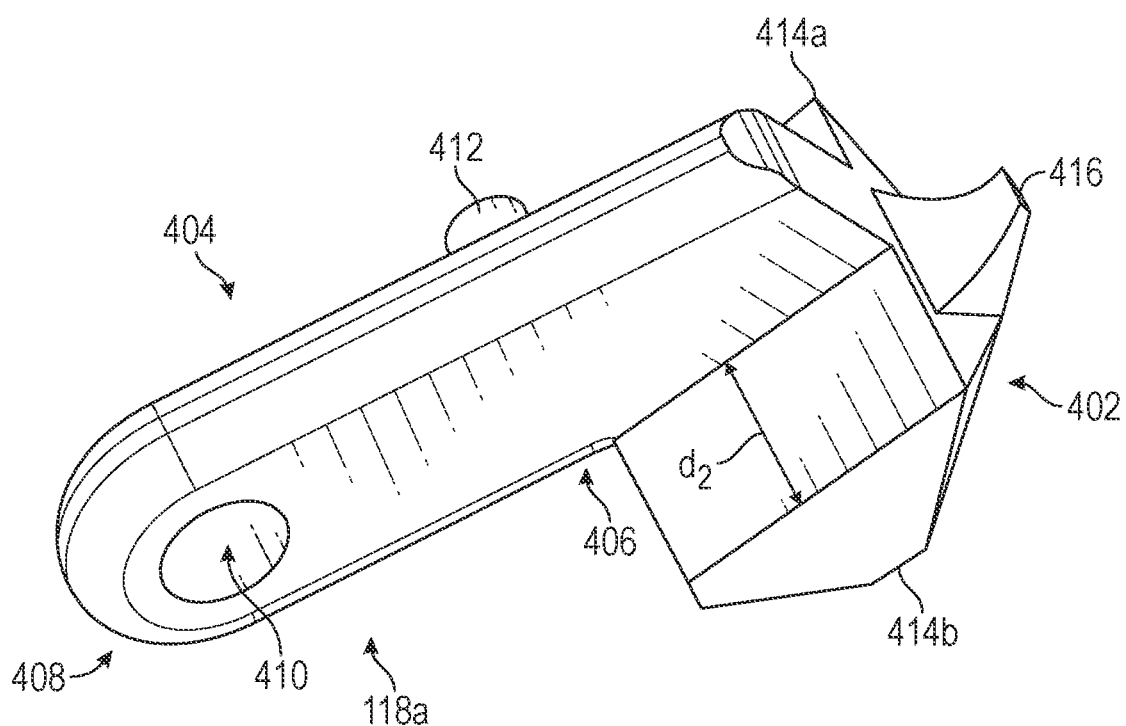
Figure 4C:
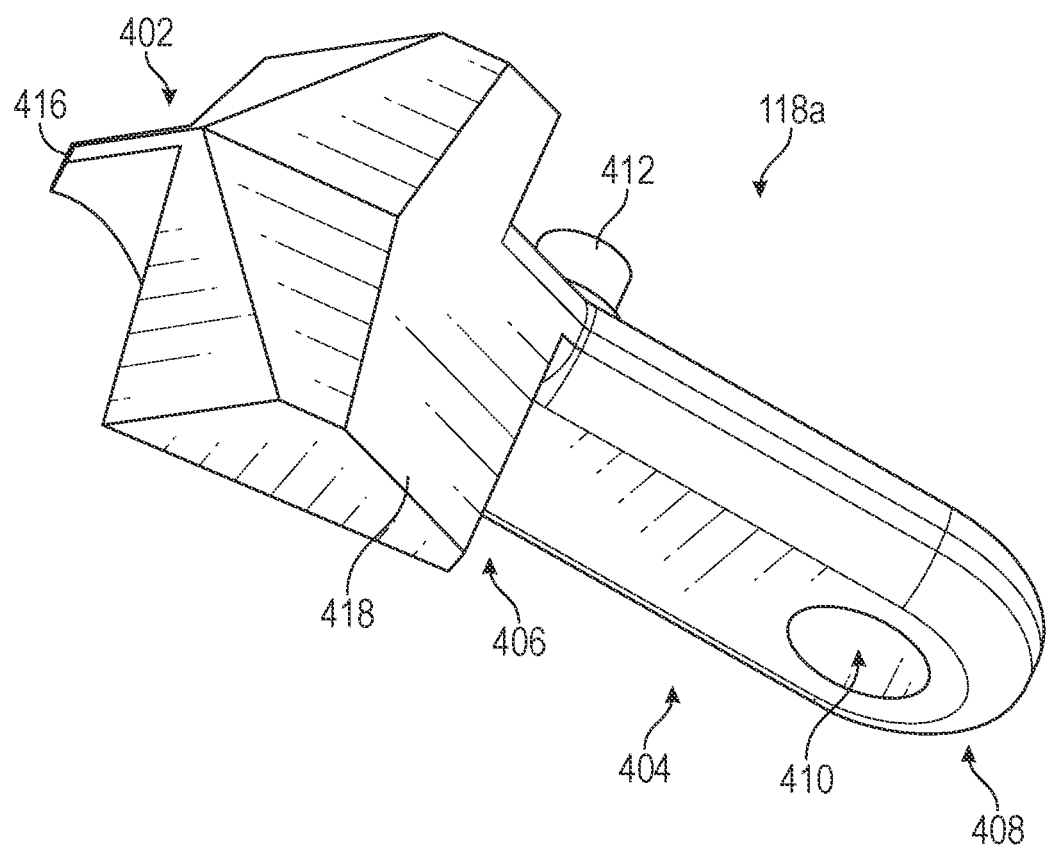

FIGS. 4A, 4B, and 4C illustrate first wing 118a for some embodiments of the present disclosure. First wing 118a may be substantially similar to second wing 118b. In some embodiments, first wing 118a comprises a wing tip 402 and a main body 404. Main body 404 has a distal end 406 that transitions into wing tip 402 (also referred to as an outer end) and a proximal end 408 (also referred to as an inner end) that may be received within opening 210 of plunger 122. Proximal end 408 may comprise a hole 410 therethrough in which a pin (see FIGS. 5A and 5B) may be inserted to couple first wing 118a to plunger 122. A connecting member 412 may protrude from main body 404 to which first linkage 300a may be mounted via first opening 304a.

Wing tip 402 may comprise a first side 414a and a second side 414b that are on opposing sides of main body 404. A fang 416 may extend from wing tip 402 and may be substantially in-line with main body 404. In some embodiments, first side 414a has a first length $d_1$ extending laterally from main body 404, and second side 414b has a second length $d_2$ extending laterally from main body 404. In some embodiments, $d_2$ is greater than $d_1$. In some embodiments, $d_2$ is about 1.5 times, about 2 times, about 2.5 times, or about 3 times greater than $d_1$. The asymmetry of first wing 118a may maximize the surface area with the contact surface, while also allowing for wings 118a, 118b to be stowed within window 120 as shown in FIG. 5B. An exterior surface 418 of wing tip 402 may comprise one or more flat faces that may sit against or anchor to the cortical bone of the sacrum when implant 100 is in its final position. In some embodiments, the one or more flat faces are entirely flat, while in other embodiments, the one or more flat faces may have a slight curvature and/or other surface features to increase surface contact with the cortical bone of the sacrum. For example, exterior surface 418 may comprise teeth, scallops, knurls, and the like, or any combination thereof.

FIG. 5A illustrates wing assembly 500 of implant 100 in the open configuration, and FIG. 5B illustrates wing assembly 500 in the closed configuration for some embodiments of the present disclosure. Broadly, wing assembly 500 comprises first wing 118a, second wing 118b, plunger 122, and linkages 300a, 300b. As discussed above, plunger 122 may be advanced distally within first body 102 to deploy wings 118a, 118b out of window 120 and into the cancellous bone of the sacrum. As shown, first side first side 414a of first wing 118a may oppose second side 414b of second wing 118b, and second wide 414b of first wing 118a may oppose first side 414a of second wing 118b. Thus, when stowed, main bodies 404 of wings 118a, 118b may be adjacent.

A first pin 502 may couple wings 118a, 118b to plunger 122. Pin 502 may be inserted through first opening 212a on plunger 122, through hole 410 on first wing 118a, through hole 410 on second wing 118b, and then through first opening 212a on plunger 122. Thus, the inner end 408 of each wing 118a, 118b may be received within opening 210 of plunger 122. First pin 502 may form a pivot point for wings 118a, 118b. Therefore, as plunger 122 is advanced distally to deploy wings 118a, 118b, first wing 118a and second wing 118b may pivot in a first direction about the pivot point to extend out of window 120. Likewise, when plunger 122 is moved proximally, wings 118a, 118b may pivot in a second direction that is opposite the first direction to return to the closed configuration illustrated in FIG. 5B.

A second pin 504 may couple first linkage 300a to second linkage 300b and may be received within second opening 304b on both first linkage 300a and second linkage 300b. As shown in FIGS. 1A and 1B, second pin 504 may be fixed within first body 102 such that second pin 504 does not move when plunger 122 is moved longitudinally. Thus, a distance between first pin 502 and second pin 504 may change between the closed configuration and the open configuration. As such, second pin 504 may form a second pivot point for wing assembly 500. Linkages 300a, 300b may pivot about second pin 504 as plunger 122 is moved longitudinally. Further, as shown in FIG. 5B, first ends 302a of linkages 300a, 300b may abut a top surface 506 of arms 208a, 208b on plunger 122 such that, as plunger 122 is advanced distally, top surface 506 pushes first ends 302a to rotate linkages 300a, 300b to deploy wings 118a, 118b. In the orientation of wing assembly 500 depicted in FIGS. 5A and 5B, as plunger 122 moves distally, plunger 122 pushes on first end 302a of first linkage 300a to rotate clockwise and on first end 302a of second linkage 300b to rotate counterclockwise. Caps may be coupled to the ends of second pin 504 to secure second pin 504 to first body 102.

Figure 6:
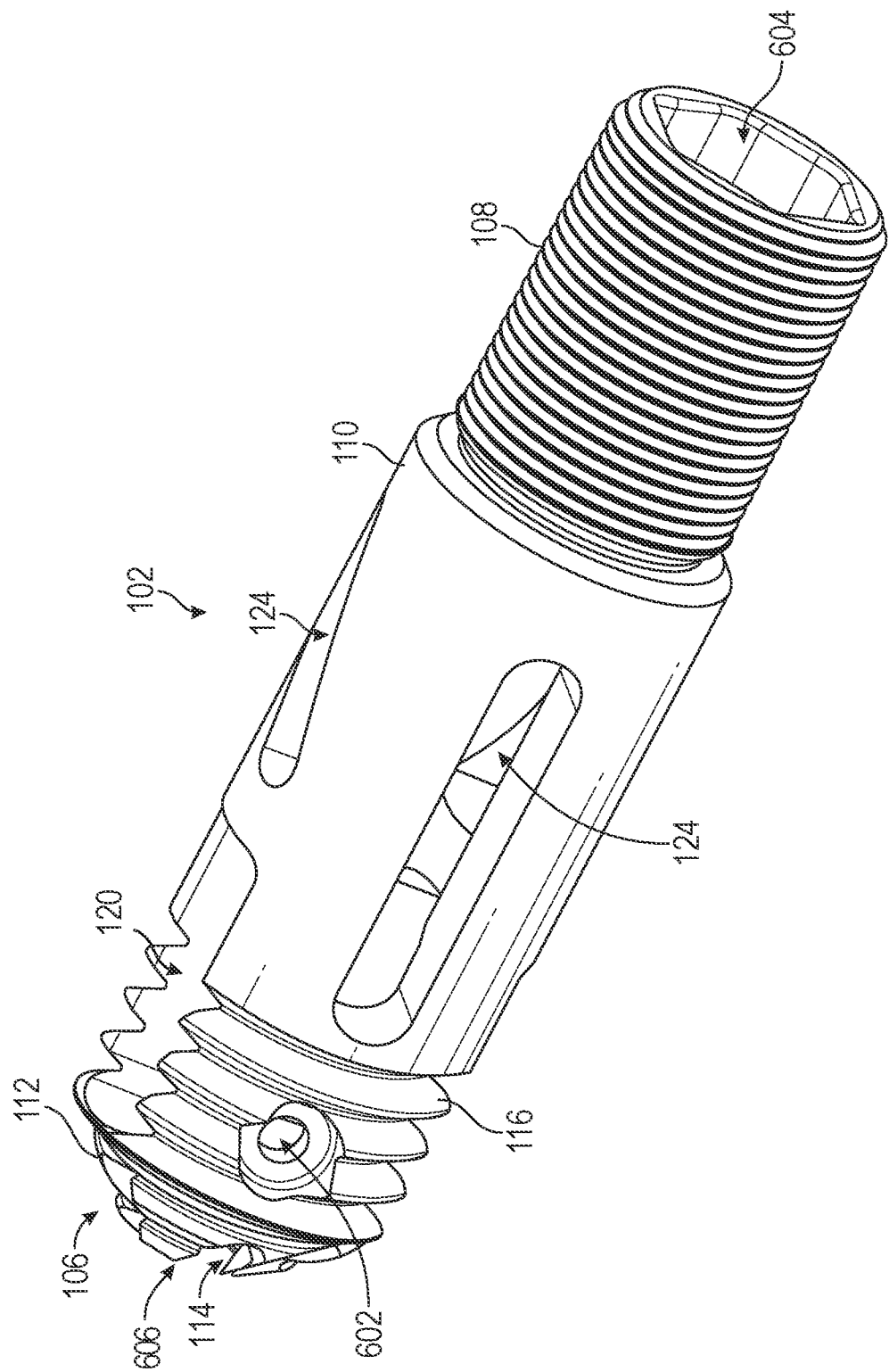
FIG. 6 illustrates a first body of the implant for some embodiments.

FIG. 6 illustrates first body 102 for some embodiments of the present disclosure. As discussed above, first body 102 may comprise distal end 106 having threads 116 thereon to aid in advancing implant 100 into the target space. Distal end 106 may further comprise an opening 602 through which second pin 504 may be received to couple first wing 118a to second wing 118b via linkages 300a, 300b as discussed above.

Proximal end 108 may define a bore 604 corresponding to bore 132. Bore 604, in some embodiments, extends entirely through first body 102, such as when distal tip 112 comprises an opening 606 to promote self-harvesting of bone. In other embodiments, bore 604 extends through proximal end 108, central section 110, and distal end 106 and terminates at distal tip 112 when distal tip 112 is formed as a solid tip. As discussed above, an inserter device may be received within bore 604 and interface with plunger 122 to move plunger 122 longitudinally to adjust wings 118a, 118b between the open and closed configurations.

Figure 7:
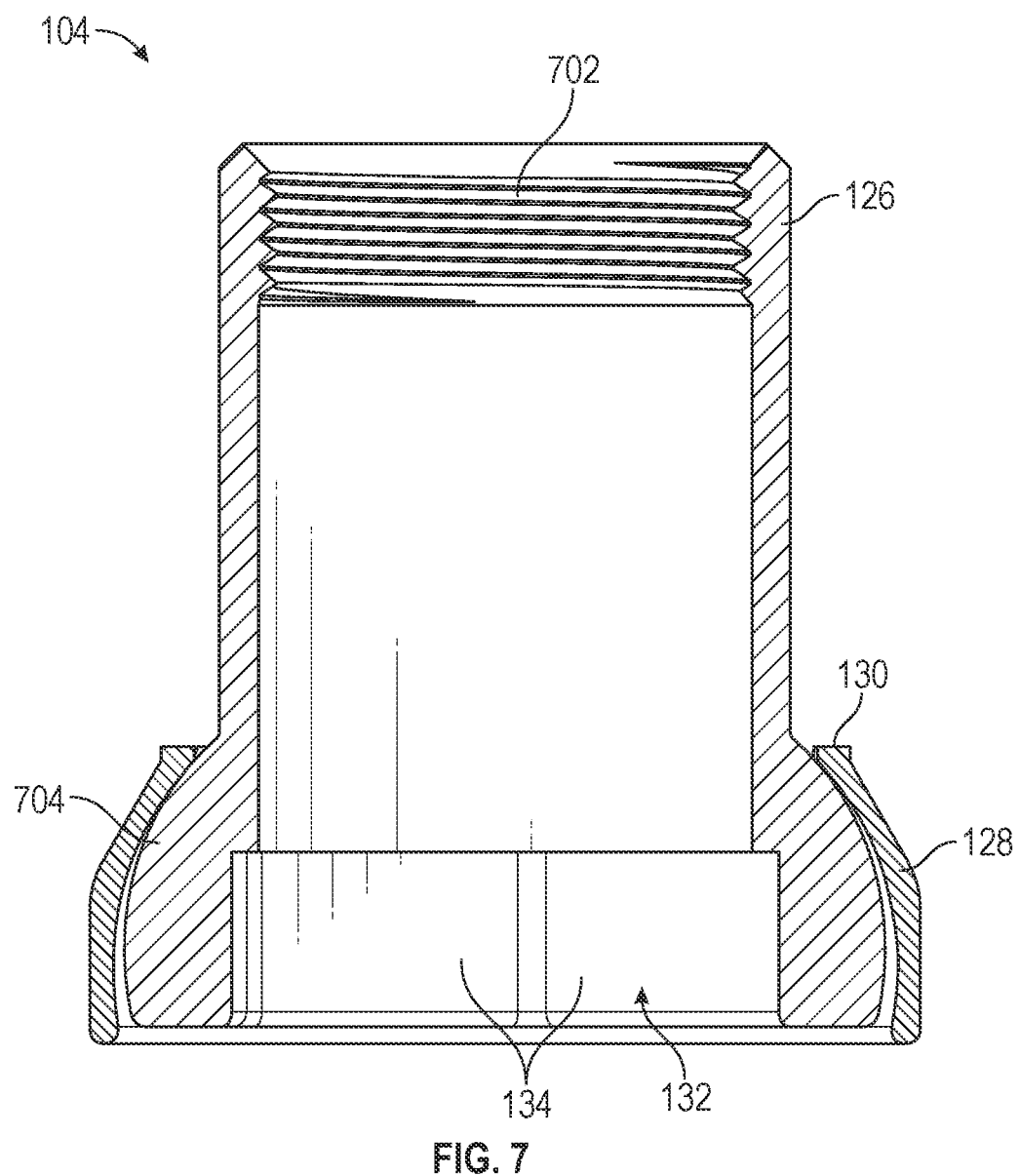
FIG. 7 illustrates a cross-sectional view of a second body of the implant for some embodiments.

FIG. 7 illustrates a cross sectional view of second body 104 for some embodiments of the present disclosure. Outer sleeve 126 may comprise internal threads 702 that mate with the threaded proximal end 108. Thus, after anchoring wings in the sacrum, outer sleeve 126 may be threaded along proximal end 108 to add compression across the SI joint, thereby increasing stabilization of the SI joint and promoting fusion thereof. Due to poor bone quality in the sacrum, it can be difficult to fuse the SI joint. Increasing the amount of compression provided by implant 100 enhances fusion because the movement is reduced when the SI joint is compressed. In some embodiments, outer sleeve 126 is formed with a retaining feature configured to prevent outer sleeve 126 from being removed or otherwise decoupled from proximal end 108. In some embodiments, second body 104 is removable from first body 102. As shown, internal threads 702 are disposed at a distal end of outer sleeve 126 and a smooth inner portion extends proximally from internal threads 702. Outer sleeve 126 may comprise a flared proximal end 704 configured to retain compressive element 128 thereon. The inner walls 134 of flared proximal end 704 may define the shape of a proximal end of bore 132 for receiving an inserter device therein as previously discussed.

Figure 8:
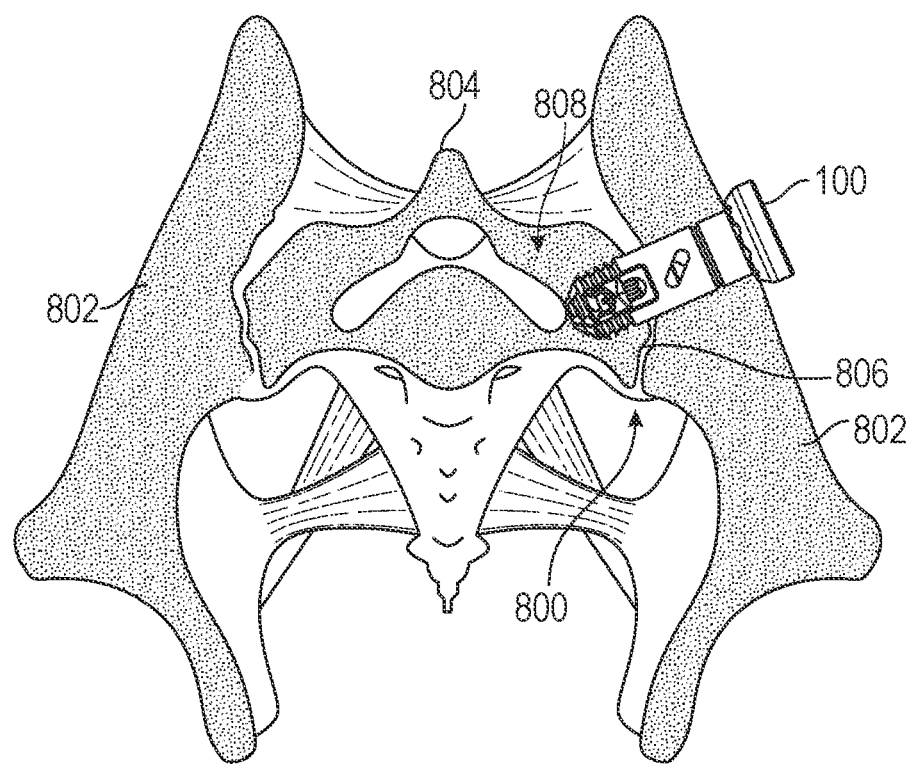
FIG. 8 illustrates the implant inserted across the SI joint for some embodiments.

FIG. 8 illustrates implant 100 inserted across an SI joint 800 for some embodiments. The SI joint 800 connects each ilium 802 to the sacrum 804 on either side of the sacrum 804. To access the sacrum 804, a minimally invasive incision may be made using a lateral approach such that the implant 100 can be inserted across the SI joint 800, and a drill may be used to drill through the ilium 802 and into the sacrum 804.

Once access to sacrum 804 is created, implant 100 may be inserted across the SI joint as follows. First, an implant insertion instrument may be engaged with implant 100 to insert implant 100 into the hole created by the drill. Exemplary insertion instruments are discussed below with respect to FIGS. 23A-35B. Implant 100 may be inserted into the hole until wings 118a, 118b are within the cancellous bone 808. Second, a plunger instrument may be inserted through bores 132, 604 and engage with the internal threads on plunger 122. The plunger instrument may have an externally threaded distal end to mate with plunger 122. The plunger instrument may then move plunger 122 distally to deploy wings out of window 120 and into cancellous bone 808. Third, implant 100 may be pulled proximally to anchor wings 118a, 118b to the cortical bone 808. The implant insertion instrument may be used to retract implant 100 proximally. Fourth, second body 104 may be threaded along proximal end 108 to add compression across the SI joint. A hex driver or other tool may be received within bore 132 and couple to inner walls 134 to rotate second body 104 along proximal end 108. Proximal end 108 may be advanced distally to anchor compressive element 128 against ilium 802 and/or to partially embed compressive element 128 into the ilium 802. As such, a distal anchor is formed by wings 118a, 118b anchored against cortical bone 808, and compressive element 128 anchors against the ilium 802, forming a proximal anchor. The distal anchor is selectively positioned in the open configuration and the closed configuration. As discussed above, plunger 122 may have an opening or cannulation such that, once implant 100 is in the open configuration, implant 100 may be packed with bone graft, and the bone graft may be packed through central bore 206.

Second Implant Embodiment

Figure 9A:
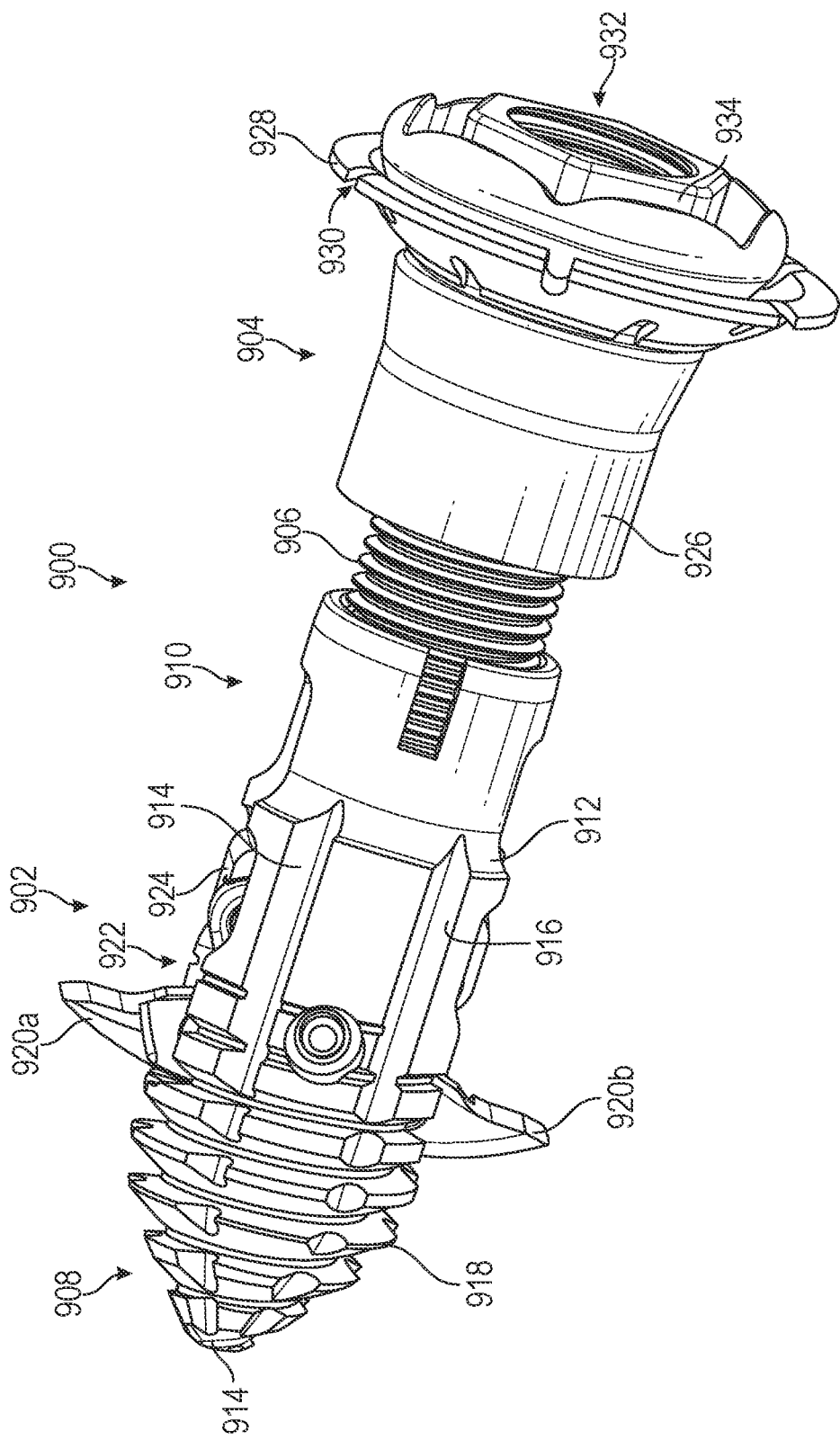
FIG. 9A illustrates a second embodiment of the implant in an open configuration for some embodiments.
Figure 9B:
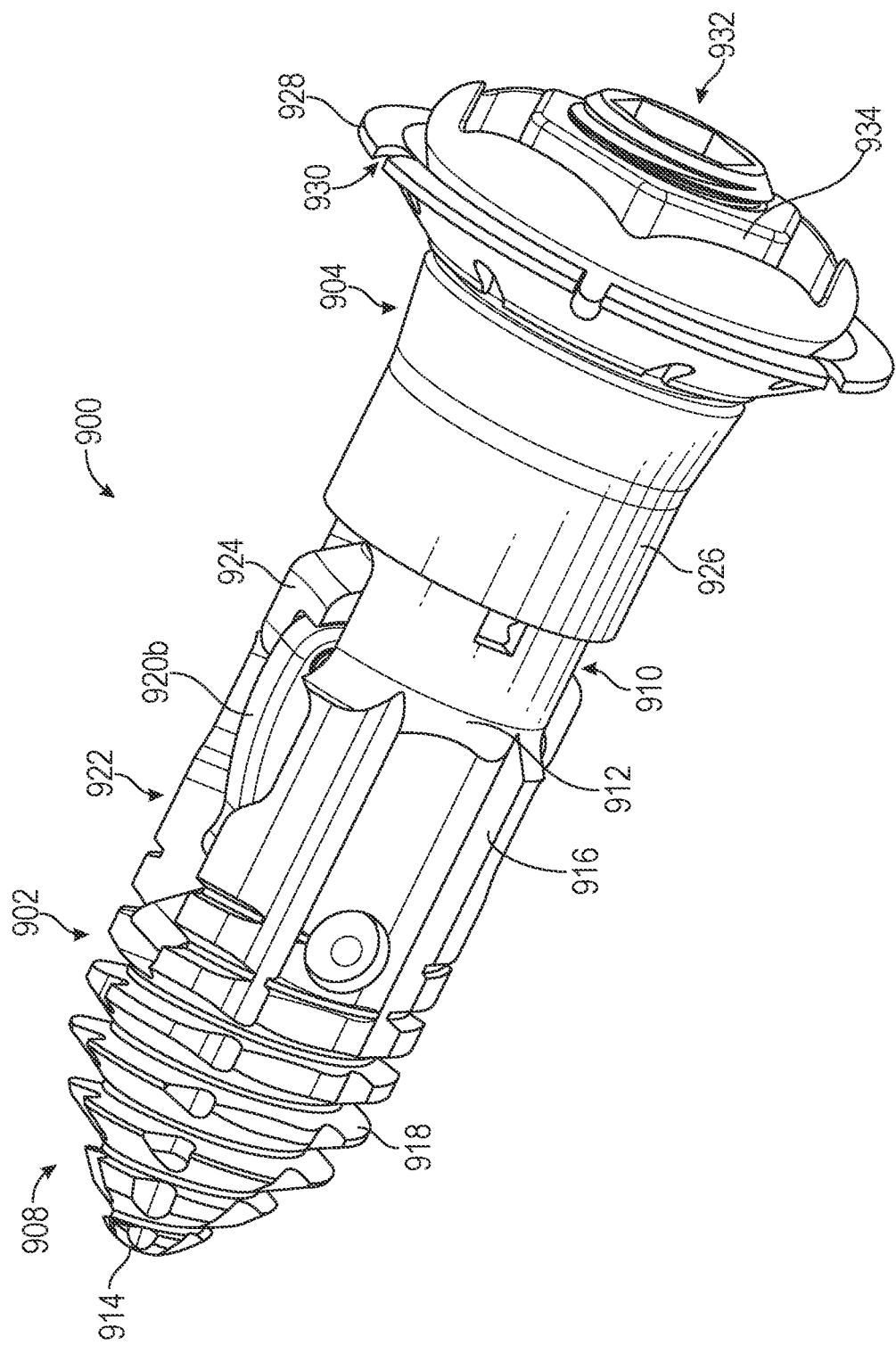
FIG. 9B illustrates the second embodiment in a closed configuration for some embodiments.

FIG. 9A illustrates another embodiment of an implant 900 for stabilization and fusion of the SI joint in an open configuration, and FIG. 9B illustrates implant 900 in a closed configuration for some embodiments of the present disclosure. Implant 900 may comprise a distal or first body 902, a proximal or second body 904, and a threaded body 906. Differing from implant 100, threaded body 906 may not be integral with first body 902 and may be moved relative to first body 902. In some embodiments, threaded body 906 is a lead screw.

In some embodiments, first body 902 comprises a distal end 908 and a proximal end 910. Distal end 908 transitions to proximal end 910 via a concave portion 912 that reduces the diameter of proximal end 910 relative to distal end 908. The distal end 908 may include a distal tip 914, which may be solid or formed with one or more fenestrations as discussed above with respect to implant 100. First body 902 may comprise one or more flutes 916 that extend proximally from distal tip 914 and may terminate at concave portion 912 of first body 902. Flutes 916 may aid in self-harvesting of bone during insertion and implantation of implant 900. Further, flutes 916 aid in self-tapping implant 900 into the target space. In some embodiments, one or more flutes 916 extend from distal tip 914 but terminate before concave portion 912. In other embodiments, flutes 916 extend from distal end 908 to proximal end 910. Broadly, flutes 916 may extend along any portion of implant 900 and may take various sizes. In some embodiments, flutes 916 are substantially evenly spaced on first body 902. In some embodiments, the spacing between adjacent flutes 916 is not even. In some embodiments, the number of flutes 916 is in the range of 1-10.

Distal tip 914 may comprise external threads 918 along a portion thereof. In some embodiments, the threads are helical threads 918. Additionally, or alternatively, the external threads may be cutting threads or box threads. In some embodiments, the threads may comprise a depth of about 0.5 mm to about 3.0 mm, an angle of about 45° to about 100°, and a spacing of about 1.0 mm to about 4.0 mm. Other thread dimensions may be used without departing from the scope hereof. In some embodiments, the non-threaded portion of first body 902 comprises a rough, outer surface and/or be coated to promote bony fusion.

First body 902 may also comprise a first wing 920a and a second wing 920b housed within a window 922 in the closed configuration and deployable out of the window 922 in the open configuration. In some embodiments, window 922 is substantially rectangular. In some embodiments, window 922 extends laterally from a first side of implant 900 to a second side of implant 900. Wings 920a, 920b may be coupled to a plunger 924 that is housed within first body 902. Plunger 924 may comprise internal threads (see FIG. 10) that can be engaged by a plunger instrument (not shown) to advance plunger 924 longitudinally for deployment and retraction of wings 920a, 920b. As compared to wings 118a, 118b on implant 100, wings 920a, 920b may be configured to follow a different deployment path and may be sharper to help cut through the cancellous bone 808 of the sacrum 804. Other differences are discussed further below. It will be appreciated that the wings and other features of implants 100, 900 may be interchangeable. For example, wings 920a, 920b may instead be used with implant 100.

Proximal end 910 may comprise internal threads that mate first body 902 to threaded body 906. Thus, threaded body 906 may be moved distally within first body 902. When wings 920a, 920b are deployed, threaded body 906 may be moved distally to abut a distal end thereof against a proximal end of plunger 924 to hold wings 920a, 920b in the deployed position. A proximal end of threaded body 906 may define a bore having a perimeter configured to receive a hex drive or other tool to thread threaded body 906 along the internal threads of proximal end 910. Threaded body 906 may also mate with internal threads on an outer sleeve 926 that is disposed on second body 904. Thus, to add compression across the SI joint when implant 900 is implanted, second body 904 can be threaded distally along threaded body 906. Second body 904 may be threaded along threaded body 906 after moving threaded body 906 distally to hold plunger 924 in place.

In some embodiments, threaded body 906 comprises a length of about 5 mm to about 50 mm. In some embodiments, threaded body 906 comprises a length of about 10 mm. Implant 900 may have a minimum length defined as a length of the implant 900 when threaded body 906 is threaded distally a maximum length and second body 904 is threaded along threaded body 906 a maximum length. The minimum length of implant 900, therefore, may correspond to a length at which a maximum amount of compression is applied to the SI joint. Likewise, implant 900 may have a maximum length defined as a length of the implant 900 when threaded body 906 is threaded proximally a maximum length, and second body 904 is threaded proximally a maximum length along threaded body 906. The maximum length of implant 900, therefore, may correspond to a length at which a minimum amount of compression is applied to the SI joint. In some embodiments, the minimum length of implant 900 is about 15 mm to about 30 mm. In some embodiments, the maximum length of implant 900 is about 60 mm to about 80 mm.

A compressive element 928 may be received on an outer surface of outer sleeve 926. As compared to compressive element 128 on implant 100, compressive element 928 may be less rigid and configured to flex more. Compressive element 928 may provide active compression across the SI joint 800 when engaged with ilium 802. In some embodiments, compressive element 928 comprises one or more slots 930 that increase the flexure of compressive element 928 as compared to a solid compressive element. In some embodiments, compressive element 928 is a polyaxial washer. In some embodiments, compressive element 928 is a Belleville washer. In some embodiments, compressive element 928 is a canted coil spring. For example, compressive element 928 may be a Bal Seal® canted coil spring.

Second body 904 may define a bore 932 that extends longitudinally therethrough. Bore 932 may extend throughout implant 900 and/or terminate at distal tip 914. Threaded body 906 may have a corresponding bore (see FIG. 13) such that an inserter device can be inserted through second body 904 and threaded body 906 and into first body 902 to mate with plunger 924. A proximal end of second body 904 may have a particular shape to receive a device configured to rotate second body 904 about threaded body 906. For example, as shown, an exterior surface 934 of the proximal end of second body 904 is hexagonal and configured to be engaged by a hex sleeve that can rotate second body 904. Other shapes and configurations for receiving other driving tools are within the scope hereof. Bore 932 also provides an opening through which bone graft can be delivered after placing implant 900 within the patient. Further, as discussed below with respect to FIG. 13, threaded body 906 may comprise openings that allow for the bone graft to flow around the implant 900 to further promote bony fusion. FIG. 10 illustrates plunger 924 for some embodiments of the present disclosure. Plunger 924 comprises a distal end 1002 and a proximal end 1004. In some embodiments, plunger 924 defines a central bore 1006 therethrough. Central bore 1006 may have internal threading configured to mate with threading on a plunger instrument for moving plunger 924 longitudinally within first body 902.

Plunger 924 may also comprise a first lateral side 1008a and a second lateral side 1008b. A first hub 1010a may protrude from distal end 1002 on first lateral side 1008a, and a second hub 1010b may protrude from distal end 1002 on second lateral side 1008b. First wing 920a may be coupled to plunger 924 via first hub 1010a, and second wing 920b may be coupled to plunger 924 via second hub 1010b. Each hub 1010a, 1010b may have an opening 1012 extending therethrough in which a pin may be received. The pin may extend through opening 1012 and an opening on an inner end of each wing 920a, 920b to couple the wings 920a, 920b to plunger 924 (see FIGS. 12A and 12B).

Figure 11A:
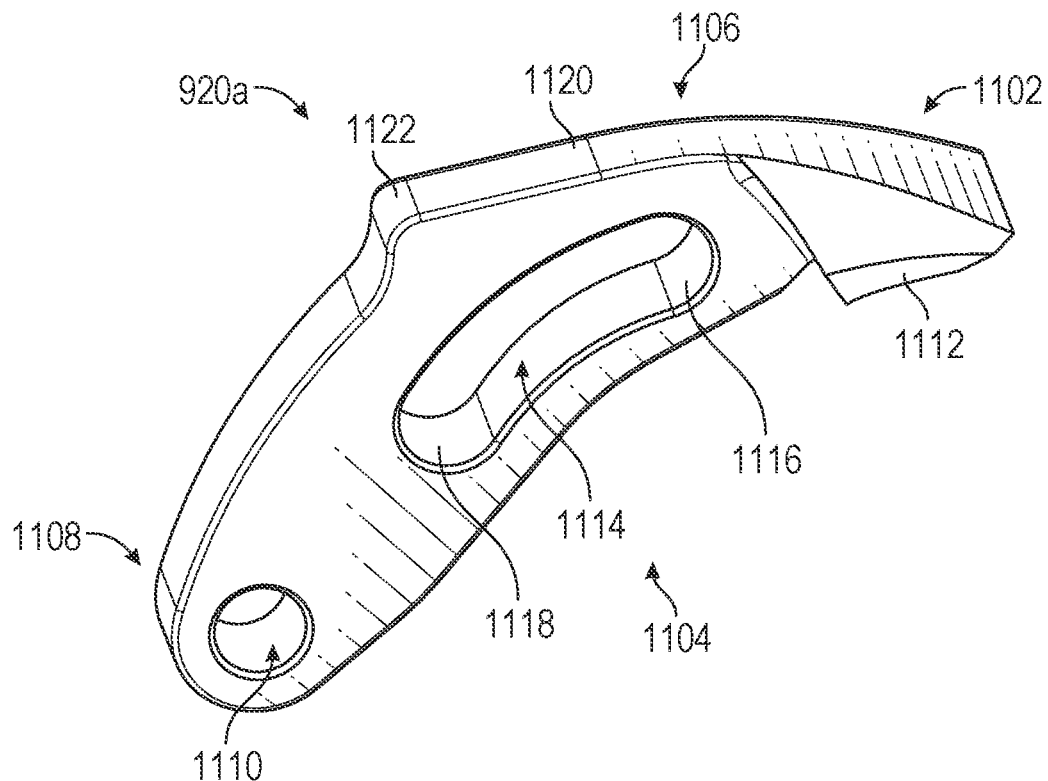
FIGS. 11A and 11B illustrate a wing of the second embodiment.
Figure 11B:
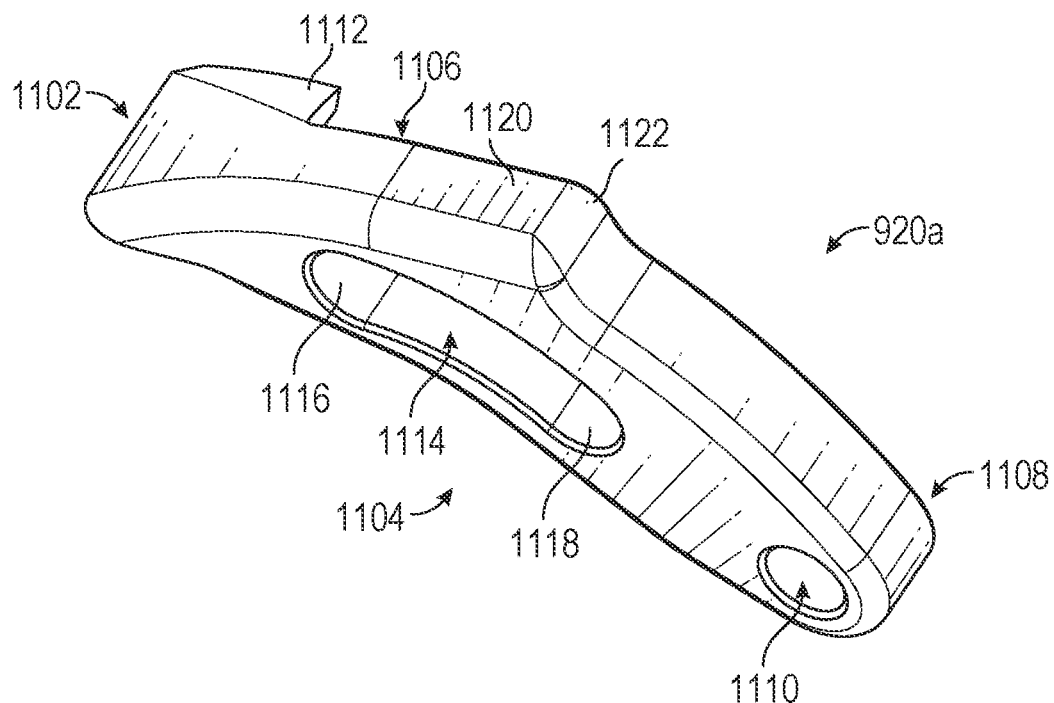

FIGS. 11A and 11B illustrate perspective views of first wing 920a for some embodiments of the present disclosure. Second wing 920b may be substantially similar to first wing 920a. First wing 920a may comprise a wing tip 1102 and a main body 1104. Main body 1104 may have distal end 1106 and a proximal or inner end 1108. Proximal end 1108 may comprise an opening 1110 therethrough for receiving the pin to couple first wing 920a to plunger 924. Distal end 1106 may transition into wing tip 1102. Wing tip 1102 may be substantially rectangular with an offset portion 1112 that may include a sharp edge. The sharp edge may aid in pushing through cancellous bone 808 of the sacrum 804 when wings 920a, 920b are deployed. In some embodiments, a bottom surface of wing tip 1102 is substantially flat to anchor against cortical bone 808.

Figure 12A:
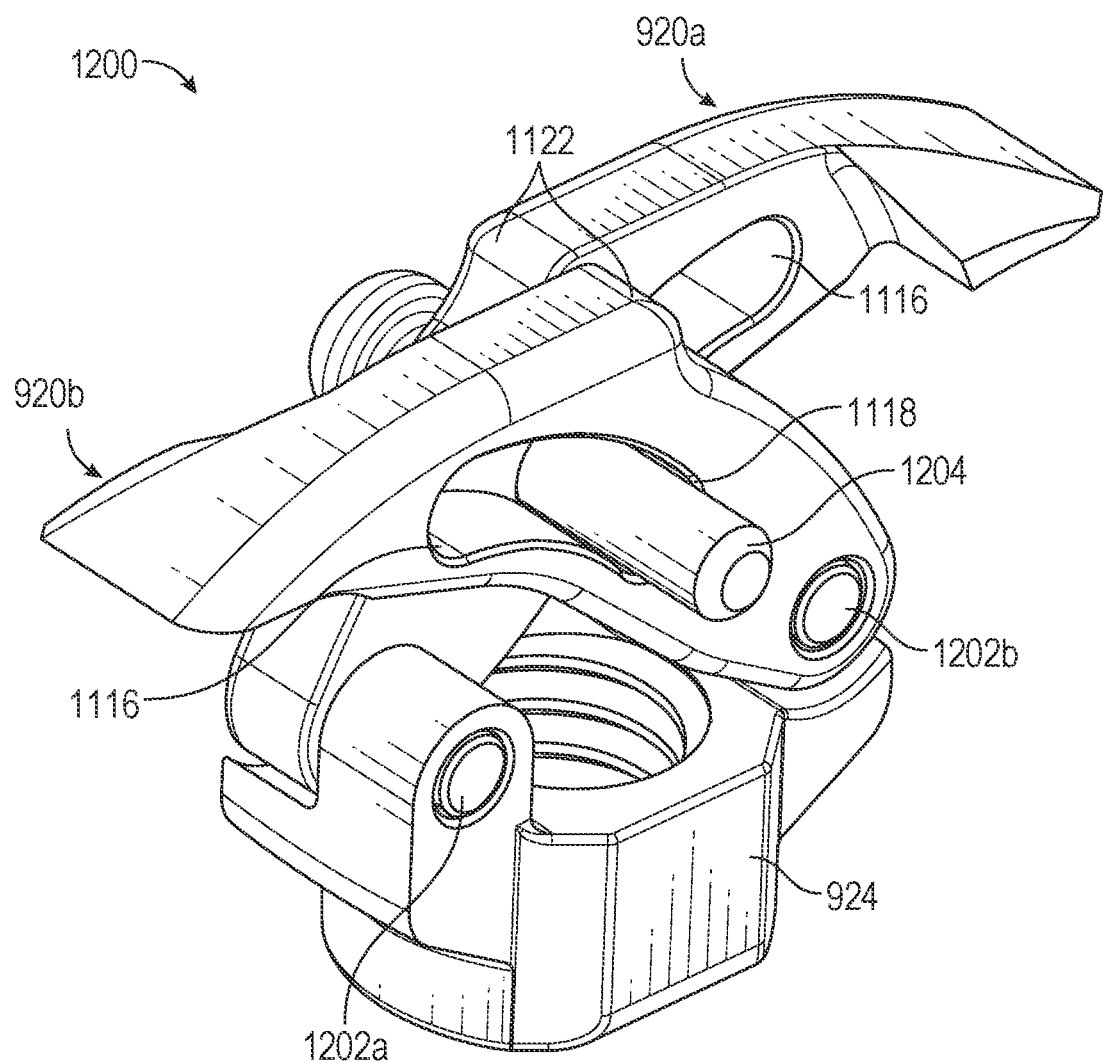
FIG. 12A illustrates a wing assembly of the second embodiment in the open configuration.
Figure 12B:
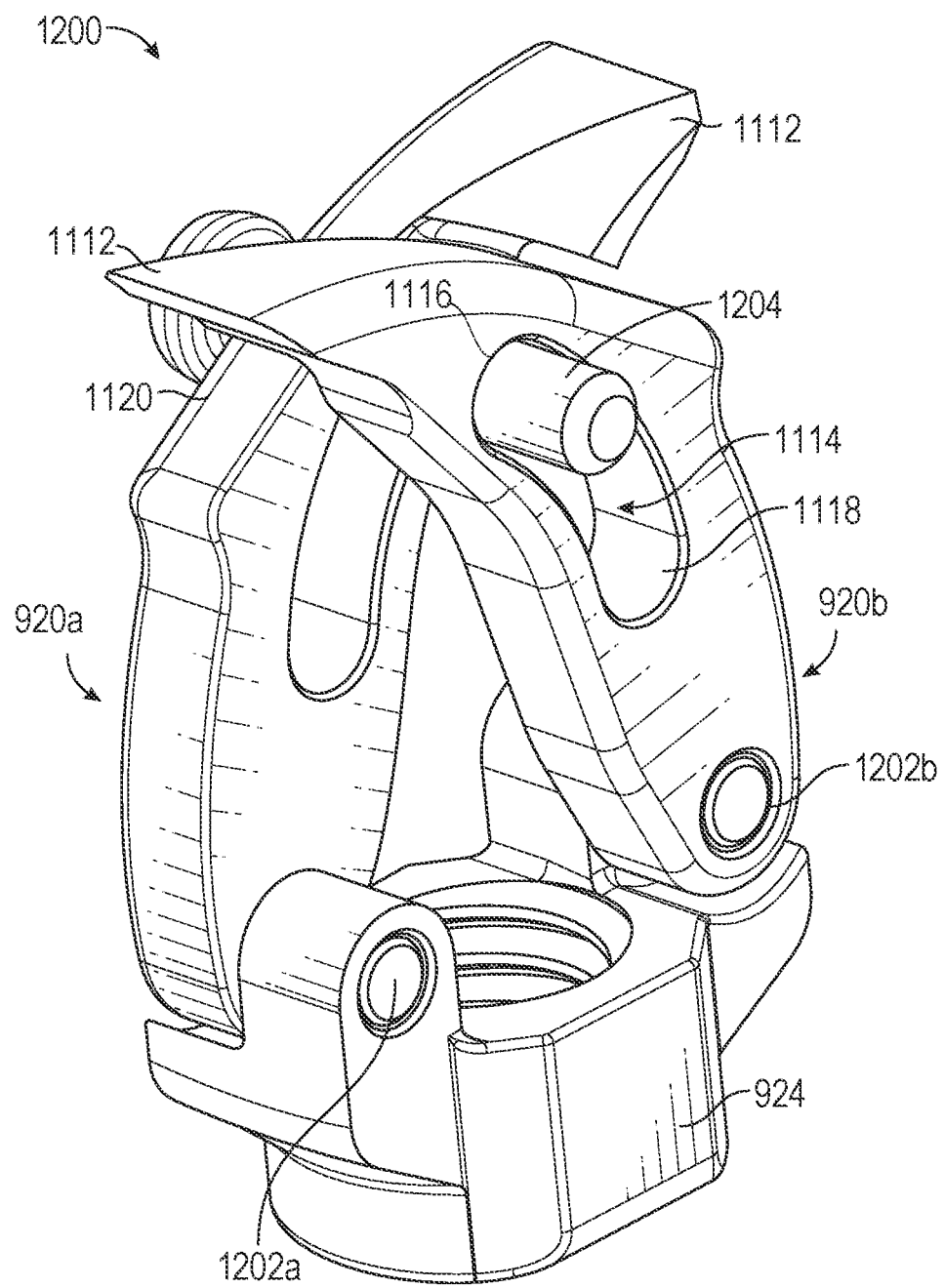
FIG. 12B illustrates the wing assembly of the second embodiment in the closed configuration.

A slot 1114 may extend through main body 1104. Slot 1114 may have a distal end 1116 and a proximal end 1118. As shown in FIGS. 12A and 12B, a fixed pin may extend through slot 1114 on first wing 920a and a corresponding slot 1114 on second wing 920b. The pin may be fixed within first body 902 such that, as plunger 924 is moved longitudinally, pin 1204 may remain substantially stationary, and slots 1114 may move relative to the pin 1204. Thus, in some embodiments, the travel path of wing 920a, 920b is defined by a curvature of the slot 1114. In some embodiments, slot 1114 defines a travel path such that wings 920a, 920b deploy path tangentially out of window 922. By path tangentially, it is meant that the wings 920a, 920b follow a path that is tangent to a curve formed by the wings in the closed configuration. This allows the wings to displace a minimal amount of cancellous bone during the deployment process, thus minimizing trauma to the surrounding areas of the sacrum. In the closed configuration, the pin 1204 may be seated at or proximal to the distal end 1116 (FIG. 12B), and, in the open configuration, the pin 1204 may be seated at or proximal to the proximal end 1118 (FIG. 12A). Further, when in the closed configuration offset portion 1112 of first wing 920*a* may be disposed above a top surface 1120 of second wing 920*b*, and an offset portion 1112 of second wing 920*b* may be disposed above a top surface 1120 of first wing 920*a*. When in the open configuration, shoulders 1122 of wings 920*a*, 920*b* may be adjacent.

FIG. 12A illustrates a wing assembly 1200 in the open configuration, and FIG. 12B illustrates wing assembly 1200 in the closed configuration for some embodiments of the present disclosure. Wing assembly 1200 comprises first wing 920*a* and second wing 920*b* coupled to plunger 924 via hubs 1010*a*, 1010*b*. A first mounting pin 1202*a* and a second mounting pin 1202*b* may be inserted through first hub 1010*a* and second hub 1010*b*, respectively, and further through opening 1110 in each of wings 920*a*, 920*b*. When in the closed configuration, the offset portion 1112 of each wing 920*a*, 920*b* may extend over a top surface of the opposing wing.

A pin 1204 may be received within slots 1114 on wings 920*a*, 920*b* and may be fixed to first body 902. As plunger 924 moves longitudinally, wings 920*a*, 920*b* follow the curvature of slot 1114 to deploy into the cancellous bone 808 of the sacrum 804. The path may be tangent relative to a curve formed by a curvature of top surface 1120 when wings 920*a*, 920*b* are in the closed configuration. Pin 1204 may remain substantially stationary as plunger 924 moves longitudinally.

Figure 13:
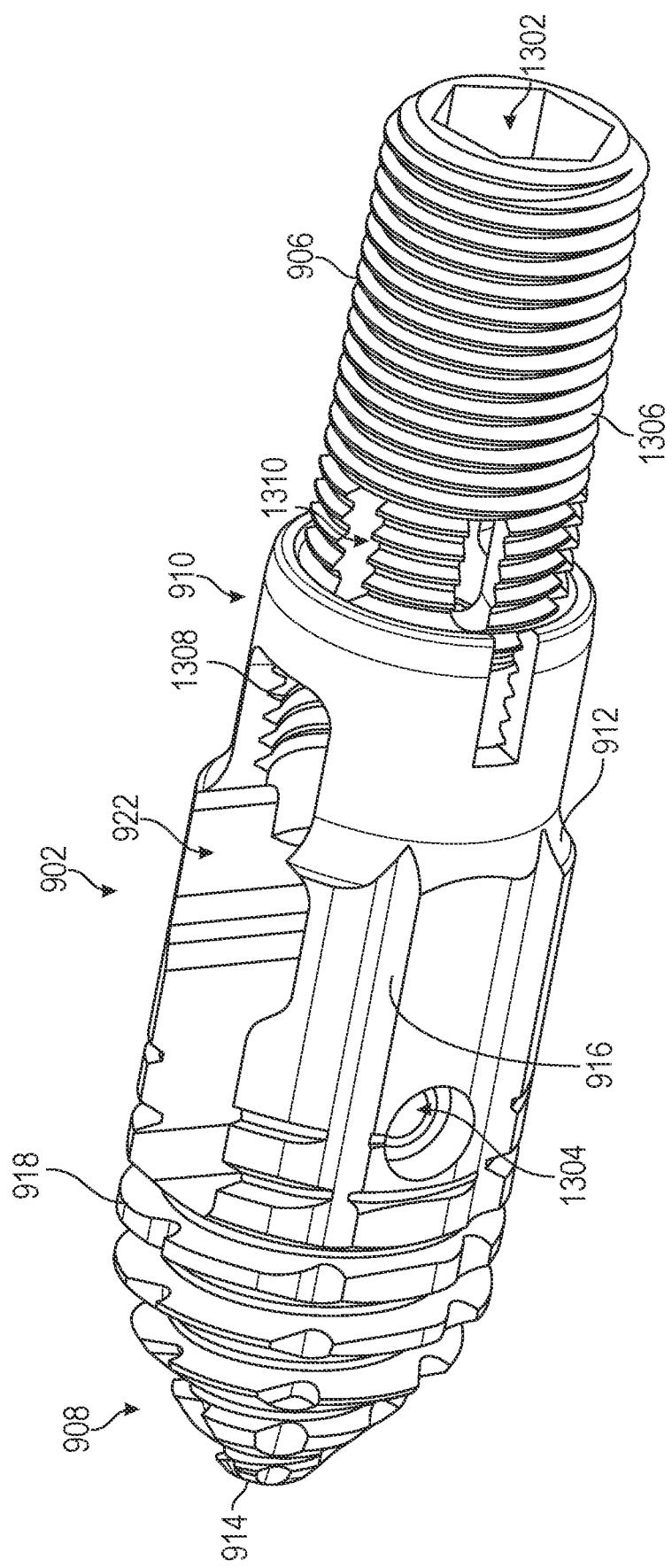
FIG. 13 illustrates a first body and a threaded body of the second embodiment.

FIG. 13 illustrates first body 902 coupled to threaded body 906 for some embodiments of the present disclosure. As shown threaded body 906 comprises a bore 1302 corresponding to bore 932. Thus, an operator may insert tools through second body 904 and threaded body 906 into first body 902 to move plunger 924. First body 902 may further comprise an opening 1304 through which pin 1204 may be fixed and operatively connect first wing 920*a* to second wing 920*b*. Additionally, threaded body 906 may comprise external threads 1306 configured to mate with internal threads 1308 on an inner surface of first body 902 such that threaded body 906 can be moved distally to abut against plunger 924. A proximal end of bore 1302 may have a perimeter shaped to receive a hex driver or other tool therein to rotate threaded body 906 along internal threads 1308 to abut the distal end of threaded body 906 against the proximal end 1004 of plunger 924. In some embodiments, threaded body 906 comprises one or more openings 1310 on a distal end thereof. In some embodiments, bone graft may be inserted through openings 1310. Further, openings 1310 allows for the bone graft to flow around the implant 900 after placement of implant 900 to promote bony fusion.

Figure 14:
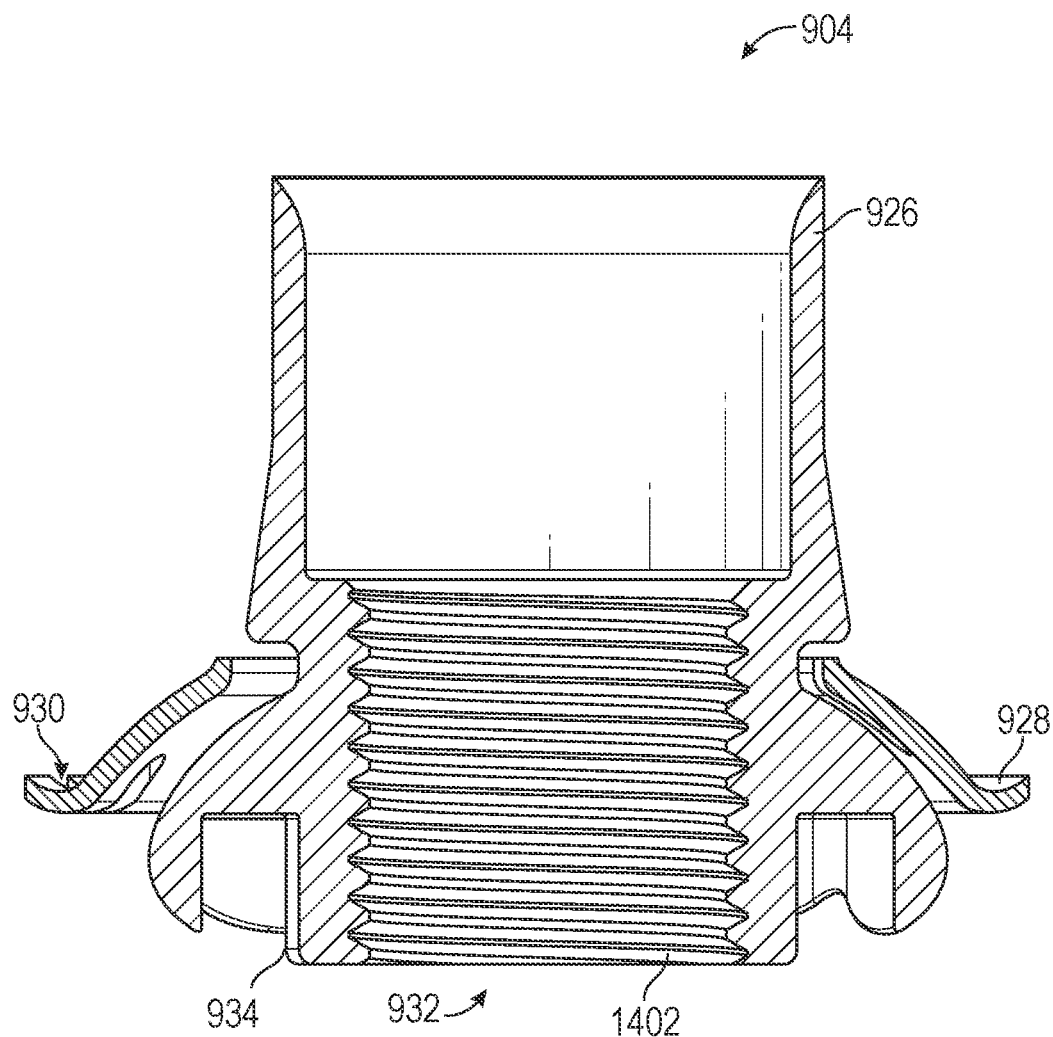
FIG. 14 illustrates a cross-sectional view of a second body of the second embodiment.

FIG. 14 illustrates a cross-sectional view of second body 904 for some embodiments of the present disclosure. Like outer sleeve 126 discussed above, outer sleeve 926 may comprise internal threads 1402 on a portion of an inner surface thereof. The internal threads 1402 may mate with external threads 1306 to move outer sleeve 926 distally to apply compression across the SI joint. In some embodiments, outer sleeve 926 comprises a proximal end defining exterior surface 934 that is hex-shaped such that a hex driver or other like tool can engage with proximal end to rotate outer sleeve 926 for longitudinal movement thereof. In some embodiments, second body 904 is removable from first body 902. As such, in some embodiments, second body 904 may be provided in various lengths, and the surgeon can choose a second body 904 having an appropriate length based on the patient's anatomy.

Figure 15:
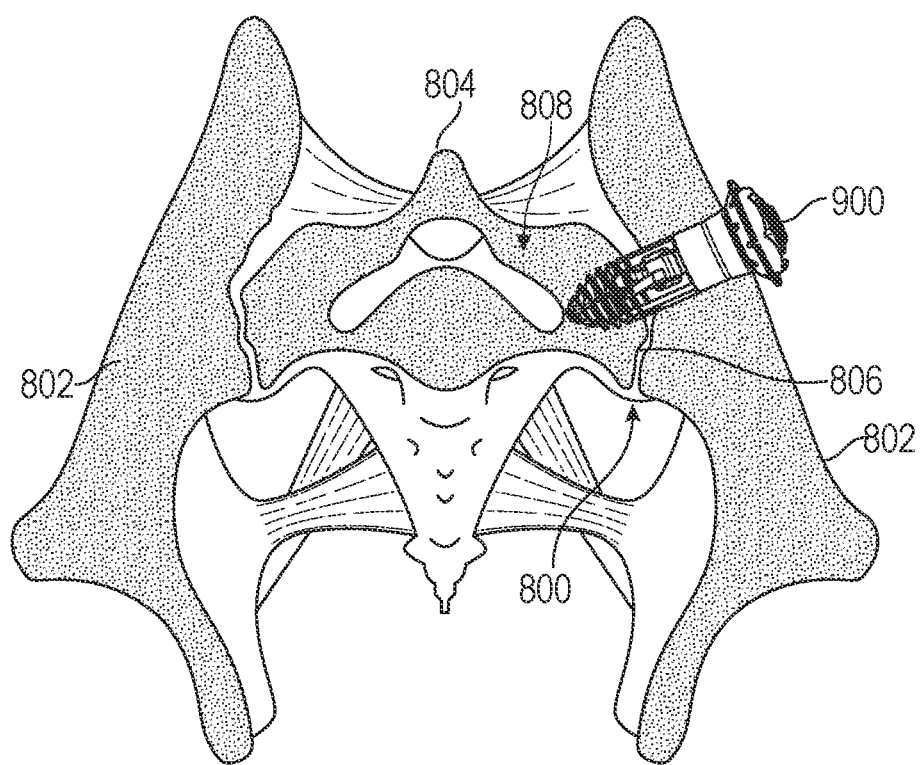
FIG. 15 illustrates the second embodiment of the implant inserted across the SI joint.

FIG. 15 illustrates implant 900 inserted across the SI joint 800 for some embodiments of the present disclosure. Implant 900 may be inserted as follows. First, an insertion instrument may be engaged with implant 900 to insert implant 900 into the hole created by the drill as discussed above with respect to FIG. 8. Implant 900 may be inserted into the hole until wings 920*a*, 920*b* are within cancellous bone 808. Second, a plunger instrument may be inserted through the bore 932 and engage with the internal threads on plunger 924. The plunger instrument may then be used to drive plunger 924 to deploy wings 920*a*, 920*b* out of window 922. Third, threaded body 906 may be threaded distally to abut against proximal end 1004 of plunger 924 to hold wings 920*a*, 920*b* in the deployed position. A hex driver or other tool may be inserted within bore 1302 to engage with the inner walls of threaded body 906 for rotation thereof. Fourth, a hex sleeve or other like tool may be used to drive second body 904 by engaging an exterior surface 934 of second body 904 to advance second body 904 along threaded body 906 to apply compression across SI joint 800. Second body 904 may be advanced distally until compressive element 928 is anchored against and/or partially embedded into ilium 802. Once inserted, bone graft may be inserted into the interior of implant 900 through bores 932, 1302. Openings 1310 in threaded body 906 allow for the bone graft to flow around the various components of implant 900.

Third Implant Embodiment

Figure 16A:
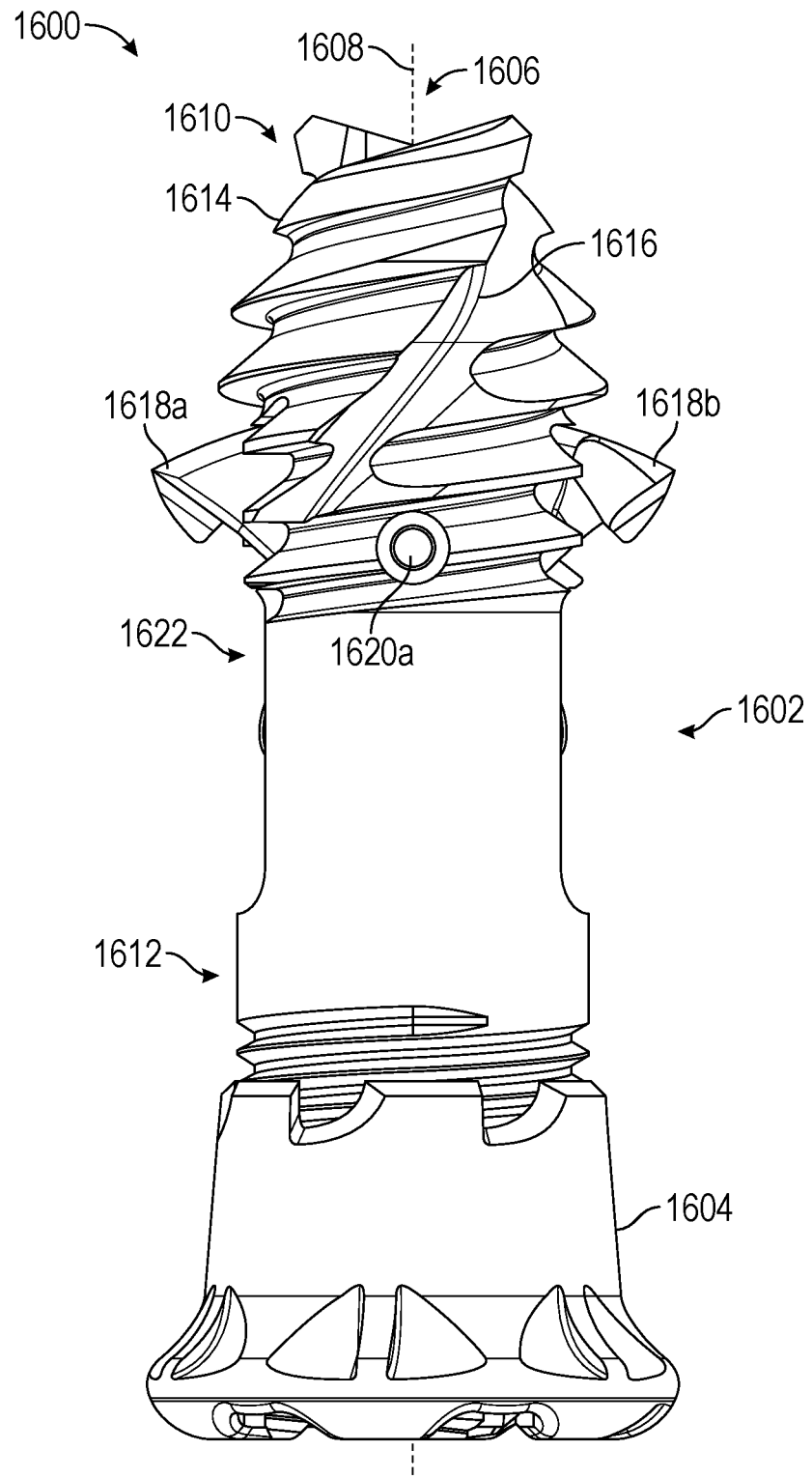
FIG. 16A illustrates a planar view of a third embodiment of the implant in a partially-open configuration for some embodiments of the present disclosure.
Figure 16B:
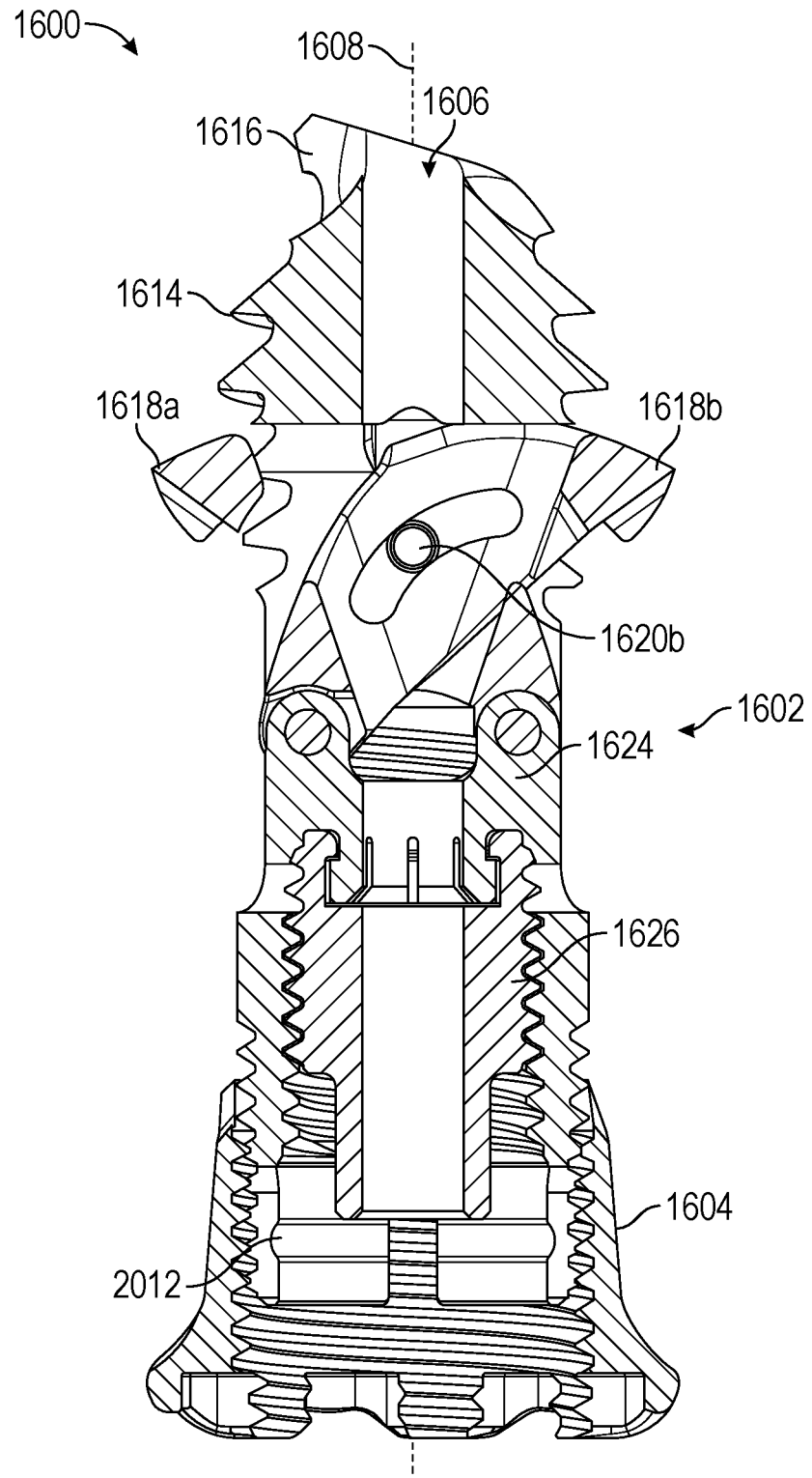
FIG. 16B illustrates a cross-sectional view of the third embodiment for some embodiments.

FIGS. 16A and 16B illustrate a planar view and a cross-sectional view, respectively, of an implant 1600 in a partially-open configuration for some embodiments of the present disclosure. Implant 1600 may share common features or elements with implants 100, 900 described herein. Implant 1600 may comprise a distal anchor formed by a pair of wings that are selectively actuatable between a closed configuration (where the wings are housed within the implant 1600) and a closed configuration (where the wings extend externally from the implant 1600). A compressive body on a proximal end of implant 1600 may form a proximal anchor. The distal anchor and the proximal anchor may cause compression across the SI joint 800.

Implant 1600 may comprise main body 1602 and compressive body 1604. A bore 1606 may extend along a longitudinal axis 1608 of implant 100. Internally, the bore 1606 may be unobstructed along longitudinal axis 1608 such that the implant 1600 can be inserted over a guidewire for implantation into a patient. As discussed further below, various components of implant 1600 may be moved to deploy the wings while maintaining an unobstructed path for a guidewire to be received through the bore 1606.

Main body 1602 may comprise a distal end 1610 and a proximal end 1612. In some embodiments, distal end 1610 is configured with one or more self-drilling features to self-drill implant 1600 into the patient. In some embodiments, distal end 1610 comprises threads 1614 and flutes 1616 to self-drill implant 1600 through the ilium 802 and into the sacrum 804. By self-drilling implant 1600 into the patient, the need for a pilot hole to be drilled into the patient before inserting implant 1600 is alleviated. Threads 1614 and flutes 1616 may also self-tap implant 1600 into the patient. In some embodiments, threads 1614 are dual-lead threads. In some embodiments, threads 1614 are single-lead threads, triple-lead threads, or quad-lead threads. Generally, threads 1614 may have any number of leads. Threads 1614 and flutes 1616 may also be configured to reduce proximal movement of implant 1600 once implanted into the patient. For example, threads 1614 and flutes 1616 may resist a proximal pulling force that may act on implant 1600, thereby holding implant 1600 in the implantation site.

Threads 1614 may be substantially similar to threads 116, 918 described above. For example, in some embodiments, threads 116 may comprise a depth of about 0.5 mm to about 3.0 mm, an angle of about 45° to about 100°, and a spacing of about 1.0 mm to about 5.0 mm. In some embodiments, the angle is 50° on the leading face and 5° on the trailing face. In some embodiments, the thread has a pitch of 4 mm. In some embodiments, the spacing of peaks between threads is about 2 mm. Other thread dimensions may be used without departing from the scope hereof.

In some embodiments, distal end 1610 comprises two flutes 1616. In some embodiments, distal end 1610 comprises fewer or greater than two flutes 1616 (e.g., four). In some embodiments, the number of flutes 1616 is equivalent to the number of leads for threads 1614. Flutes 1616 may be helical and wrap around the outer surface of distal end 1610, following the path of threads 1614. Along with self-drilling implant 1600 into bone, flutes 1616 may also help self-harvest bone during insertion and implantation of implant 1600.

Implant 1600 may comprise a distal anchor formed by a first wing 1618a and a second wing 1618b. Differing from wings 920a, 920b described above, each wing 1618a, 1618b may be fixed within implant 1600 with a separate pin 1620a, 1620b. The pins 1620a, 1620b may not extend laterally across window 1622 such that bore 1606 remains unobstructed along the length of implant 1600. In a closed configuration of implant 1600, wings 1618a, 1618b may be entirely within window 1622, while in an open configuration, wings 1618a, 1618b may be deployed out of the window 1622 (see, e.g., implant 900 shown in FIGS. 9A and 9B). As shown in FIG. 16B, second wing 1618b has a slot that rides along the second pin 1620b. When the second pin 1620b sits proximal to a first or distal end of the slot, the second wing 1618b may be in the open configuration, and when the second pin 1620b sits in a second or proximal end of the slot, the second wing 1618b may be in the closed configuration.

Each wing 1618a, 1618b may be coupled at an inner end to a distal plunger 1624. The distal plunger 1624, in turn, may be coupled to a proximal plunger 1626. The distal plunger 1624 and the proximal plunger 1626 may be housed within main body 1602. As discussed further below, the proximal plunger 1626 may be configured to be driven longitudinally to cause longitudinal movement of distal plunger 1624. When proximal plunger 1626 moves distal plunger 1624 distally, wings 1618a, 1618b may be deployed out of window 1622. Proximal plunger 1626 may threadedly engage with internal threads on main body 1602 and be threaded to move longitudinally along main body 1602.

Compressive body 1604 may form a proximal anchor for implant 1600. Compressive body 1604 may have internal threading (see FIG. 21) for threadedly engaging with external threads on proximal end 1612 of main body 1602. Accordingly, compressive body 1604 may be threaded along proximal end 1612 to adjust an effective length of implant 1600 and to change the amount of compression applied by compressive body 1604 to the SI joint 800. In contrast to implant 900, compressive body 1604 on implant 1600 may be a single piece that is configured to provide compression. Compressive body 1604 is discussed further below with respect to FIG. 21.

Figure 16C:
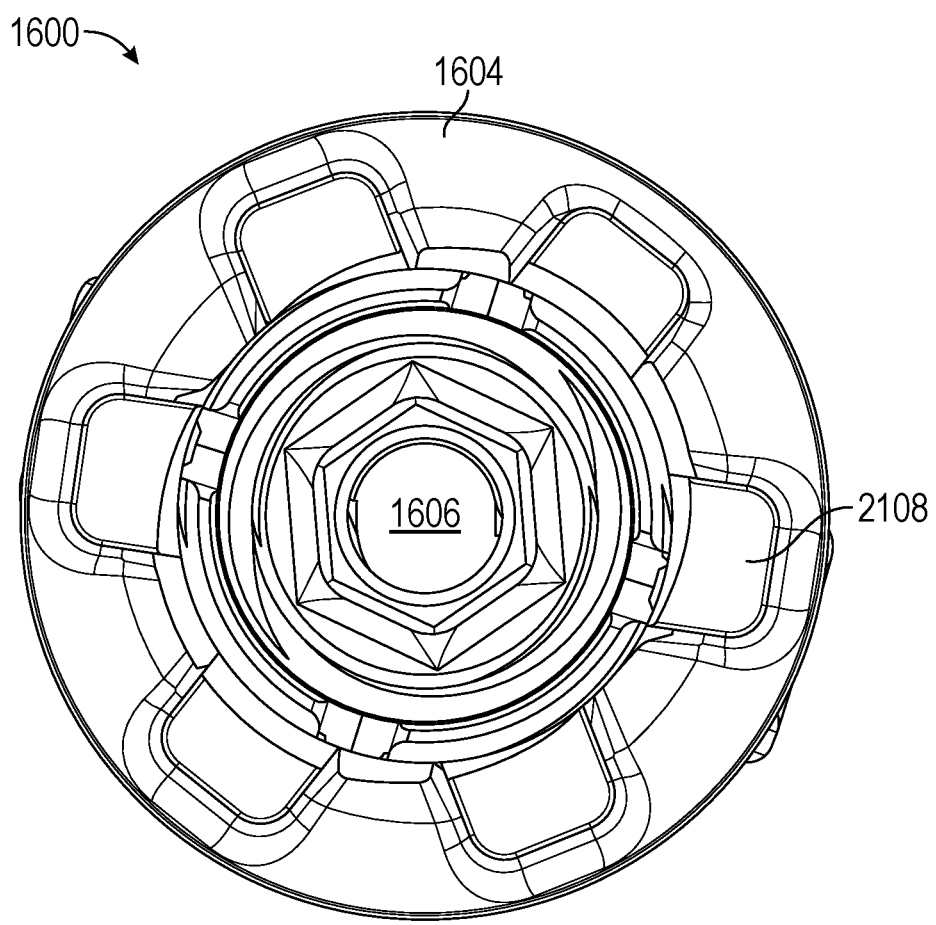
FIG. 16C illustrates a distal-looking view of the third embodiment for some embodiments.

Turning now to FIG. 16C, a distal-looking view of implant 1600 is illustrated for some embodiments of the present disclosure. As shown, bore 1606 is unobstructed centrally, along the length of implant 1600 such that implant 1600 can be inserted over the guidewire for insertion into the patient. Bore 1606 may remain unobstructed as distal plunger 1624, proximal plunger 1626, and wings 1618a, 1618b move implant 1600 between the open and closed configurations.

In some embodiments, implant 1600 is provided in various lengths. Implants of different lengths may be selected based on patient anatomy. In some embodiments, a surgical kit may be provided for performing the surgery, comprising various sized implant lengths and any instrumentation (discussed further below) necessary to perform the operations. In some embodiments, compressive body 1604 is configured to accommodate main bodies 1602 of different lengths. In some embodiments, implant 1600 is provided in a first size having a maximum length of implant 1600 at a fully-extended position of about 28.5 mm, and a minimum length of about 22 mm. In some embodiments, implant 1600 is provided in a second size where the maximum length is about 24.5 mm and the minimum length is about 18 mm. In some embodiments, implant 1600 is provided in a third size having a maximum length of implant 1600 at a fully-extended position of about 40.4 mm, and a minimum length of about 32.4 mm. In some embodiments, implant 1600 is provided in a fourth size where the maximum length is about 65.9 mm and the minimum length is about 57.9 mm.

Figure 17:
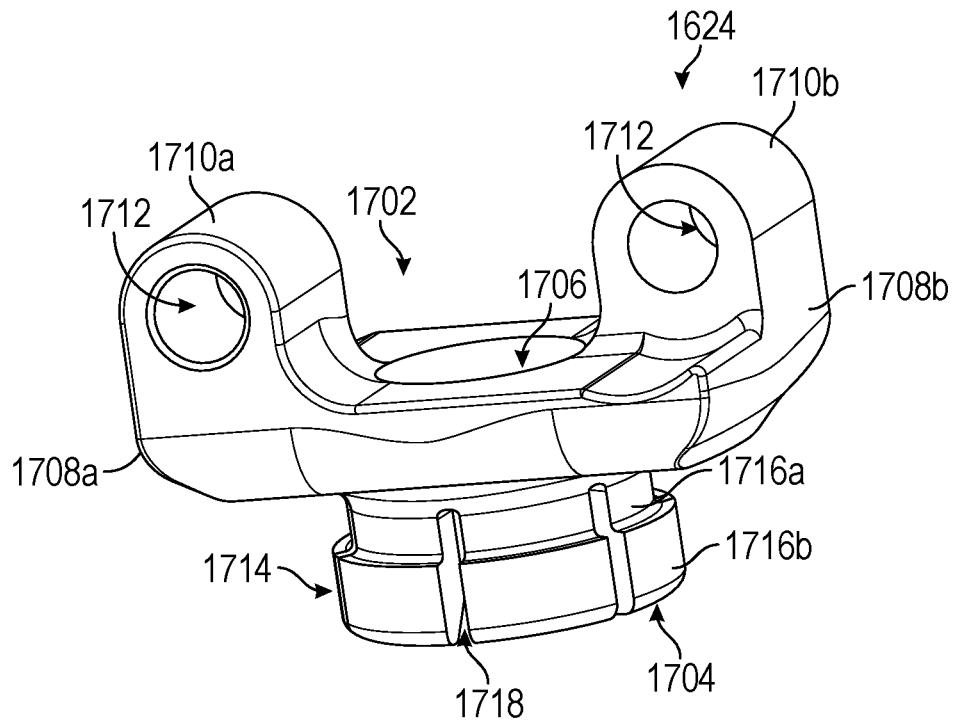
FIG. 17 illustrates an implant plunger of the third embodiment.

FIG. 17 illustrates distal plunger 1624 for some embodiments of the present disclosure. Distal plunger 1624 may comprise a distal end 1702 and a proximal end 1704. In some embodiments, distal plunger 1624 defines a central bore 1706 therethrough corresponding to bore 1606. Distal plunger 1624 may comprise a first lateral side 1708a and a second lateral side 1708b. A first hub 1710a may protrude from distal end 1702 on first lateral side 1708a, and a second hub 1710b may protrude from distal end 1702 on second lateral side 1708b. First wing 1618a may be coupled to distal plunger 1624 via first hub 1710a, and second wing 1618b may be coupled to distal plunger 1624 via second hub 1710b. Each hub 1710a, 1710b may have an opening 1712 extending therethrough in which a pin may be received. The pin may extend through opening 1712 and a corresponding opening on an inner end of each wing 1618a, 1618b to couple the wings 1618a, 1618b to hubs 1710a, 1710b (see FIG. 19).

Proximal end 1704 may comprise a connecting portion 1714 for coupling distal plunger 1624 to proximal plunger 1626. Connecting portion 1714 may have a first portion 1716a and a second portion 1716b. First portion 1716a may have a smaller diameter than second portion 1716b. Proximal plunger 1626 may couple with connecting portion 1714, and the larger diameter second portion 1716b may prevent proximal plunger 1626 from decoupling from distal plunger 1624 (see also FIG. 16B). In some embodiments, connecting portion 1714 further comprises one or more openings 1718 extending through the connecting portion 1714. The openings 1718 may be configured to provide flexure in the connecting portion 1714 as compared to forming connecting portion 1714 as a solid piece. In some embodiments, connecting portion 1714 comprises two to eight openings 1718 that are spaced evenly around connecting portion 1714. Connecting portion 1714 may comprise more, fewer, or no openings 1718 in some embodiments. In some embodiments, openings 1718 extend longitudinally through first portion 1716a and partially into second portion 1716b.

Figure 18:
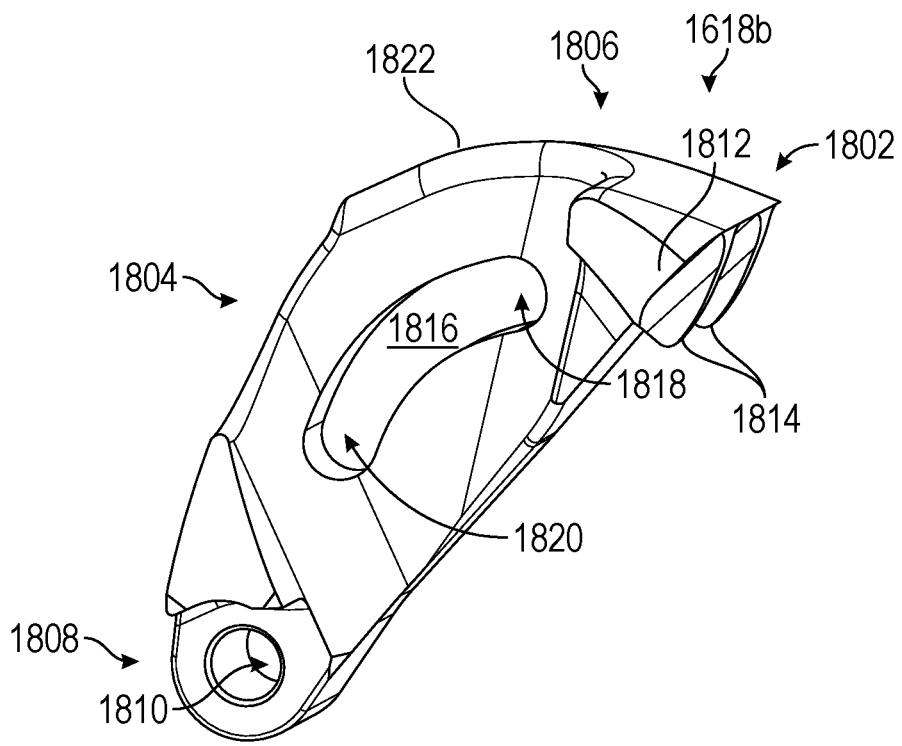
FIG. 18 illustrates a wing of the third embodiment.
Figure 19:
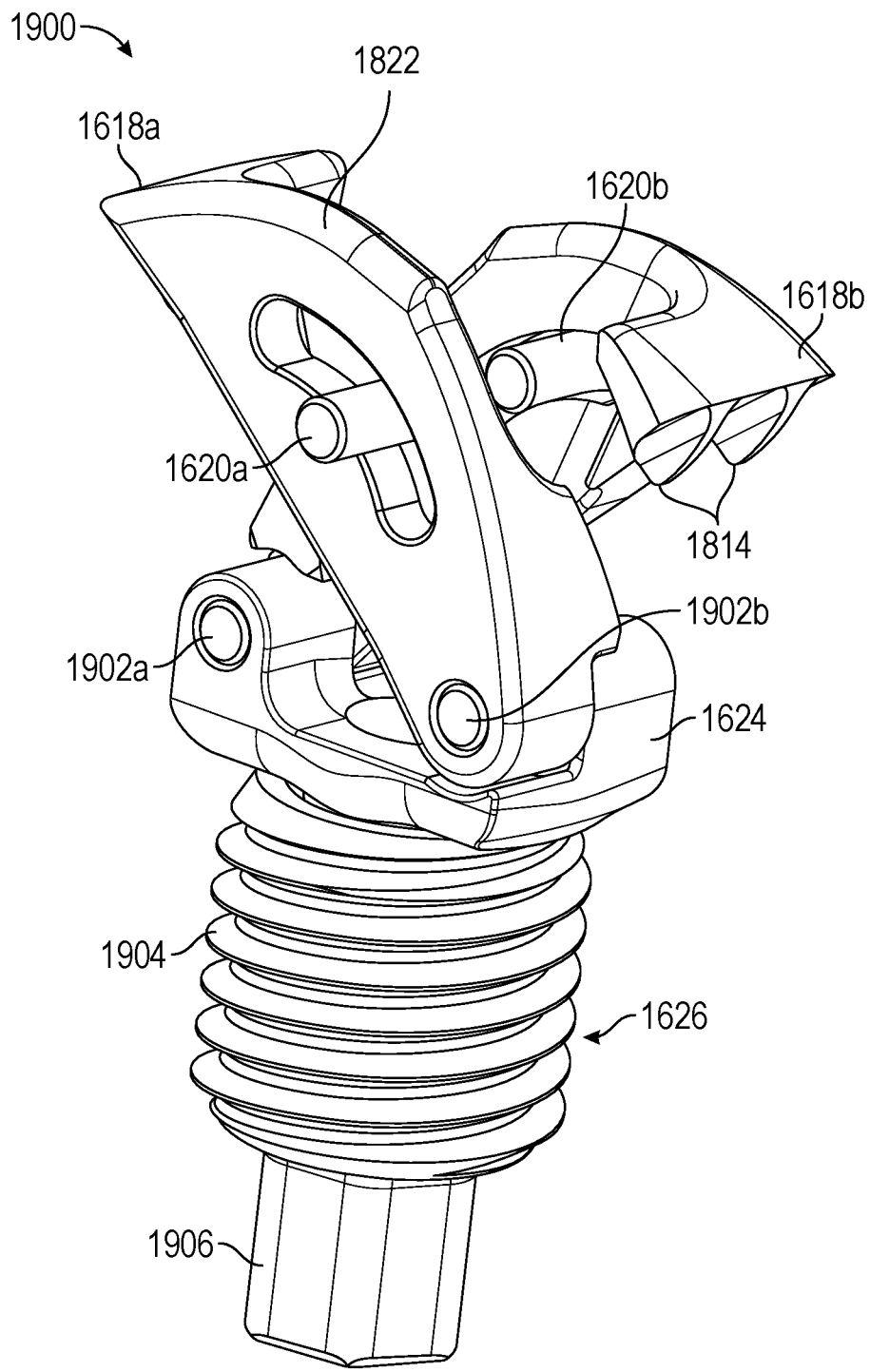
FIG. 19 illustrates a wing assembly of the third embodiment.

Turning now to FIG. 18, a perspective view of second wing 1618b is illustrated for some embodiments of the present disclosure. Second wing 1618b may be substantially similar to first wing 1618a. Wings 1618a, 1618b may be substantially similar to wings 920a, 920b. Second wing 1618b may comprise a wing tip 1802 and a main body 1804. Main body 1804 may have a distal end 1806 and a proximal or inner end 1808. Proximal end 1808 may comprise an opening 1810 therethrough for receiving a pin to couple second wing 1618b to distal plunger 1624 as shown in FIG. 19 below. Distal end 1806 may transition into wing tip 1802. Wing tip 1802 may be substantially rectangular with an offset portion 1812 that may include a sharp edge. The sharp edge may aid in pushing through cortical bone 806 of the sacrum 804 when wings 1618a, 1618b are deployed. In some embodiments, one or more fangs 1814 protrude from a bottom surface of wing tip 1802. The fangs 1814 may help anchor implant 1600 into the cortical bone 806. Further, the fangs 1814, when engaged with the cortical bone 806, may help prevent rotation of implant 1600 once implanted. In some embodiments, the bottom surface of wing tip 1802 comprises one, two, or more fangs 1814. In some embodiments, the bottom surface of wing tip 1802 is flat with no fangs 1814.

A slot 1816 may extend through main body 1804. Slot 1816 may have a distal end 1818 and a proximal end 1820. Second pin 1620b may be received within slot 1816. Second pin 1620b may be fixed within main body 1602 such that, as distal plunger 1624 is moved longitudinally, thereby forcing second wing 1618b distally, second pin 1620b may remain substantially stationary, and slot 1816 may move relative to second pin 1620b. Thus, in some embodiments, the travel path of wing 1618a, 1618b is defined by a curvature of the slot 1816. In some embodiments, slot 1816 defines a travel path such that wings 1618a, 1618b deploy path tangentially out of window 1622. As previously discussed, by path tangentially, it is meant that the wings 1618a, 1618b follow a path that is tangent to a curve formed by the wings 1618a,1618b in the closed configuration. The path tangential deployment allows the wings 1618a, 1618b to displace a minimal amount of cancellous bone 808 during the deployment process, thus minimizing trauma to the surrounding areas of the sacrum 804. In the closed configuration, second pin 1620b may be seated at or proximal to the distal end 1818 and, in the open configuration, second pin 1620b may be seated at or proximal to the proximal end 1820. Further, when in the closed configuration, the offset portion 1812 of second wing 1618b may be disposed above a top surface 1822 of second wing 1618b, and an offset portion 1812 of first wing 1618a may be disposed above a top surface 1822 of second wing 1618b. As shown in FIG. 16C, when wings 1618a, 1618b are in the closed configuration, bore 1606 remains unobstructed for the guidewire to be received therethrough.

FIG. 19 illustrates a wing assembly 1900 formed by wings 1618a, 1618b, distal plunger 1624, and proximal plunger 1626 for some embodiments of the present disclosure. The wing assembly 1900 is depicted in a partially-deployed configuration with each pin 1620a, 1620b near a center of the slot 1816, about halfway between distal end 1818 and proximal end 1820. As shown, first wing 1618a is coupled to first hub 1710a via a first pin 1902a, and second wing 1618b is coupled to second hub 1710b via a second pin 1902b. The distance between inner walls of main body 1602 and the external ends of pins 1902a, 1902b when inserted through openings 1712, 1810 may be such that pins 1902a, 1902b are unable to slide out of openings 1712, 1810, thereby maintaining the connection between wings 1618a, 1618b and distal plunger 1624.

As previously discussed, pins 1620a, 1620b may be received within openings on main body 1602 and fixed to main body 1602 such that pins 1620a, 1620b do not move during operations of the device. Pins 1620a, 1620b may extend into and/or partially through offset portion 1812 on wings 1618a, 1618b, respectively, maintaining a clear path for the guidewire to be received within bore 1606. Accordingly, when distal plunger 1624 moves distally, wings 1618a, 1618b may move along pins 1620a, 1620b to deploy out of window 1622. The path of wings 1618a, 1618b when deployed may be tangent relative to a curve formed by a curvature of top surface 1822 when wings 1618a, 1618b are in the closed configuration.

Distal plunger 1624 may be moved by longitudinal movement of proximal plunger 1626. In some embodiments, proximal plunger 1626 comprises a threaded portion 1904 and a non-threaded portion 1906. The threaded portion 1904 may engage with internal threading on main body 1602 (see FIG. 20) to move proximal plunger 1626 longitudinally. In some embodiments, the non-threaded portion 1906 has a geometry configured to couple to the insertion instrument, such that the non-threaded portion 1906 may be rotationally driven to rotate and thread non-threaded portion 1904 along the internal threads in main body 1602. For example, non-threaded portion 1906 may have a hexagonal shape for coupling to a hex driver (i.e., non-threaded portion 1906 may be a female hex), which may be formed in the insertion instrument (see FIGS. 23A-24B). It will be understood that proximal plunger 1626 has a bore therethrough corresponding to bore 1606 described above.

Figure 20:
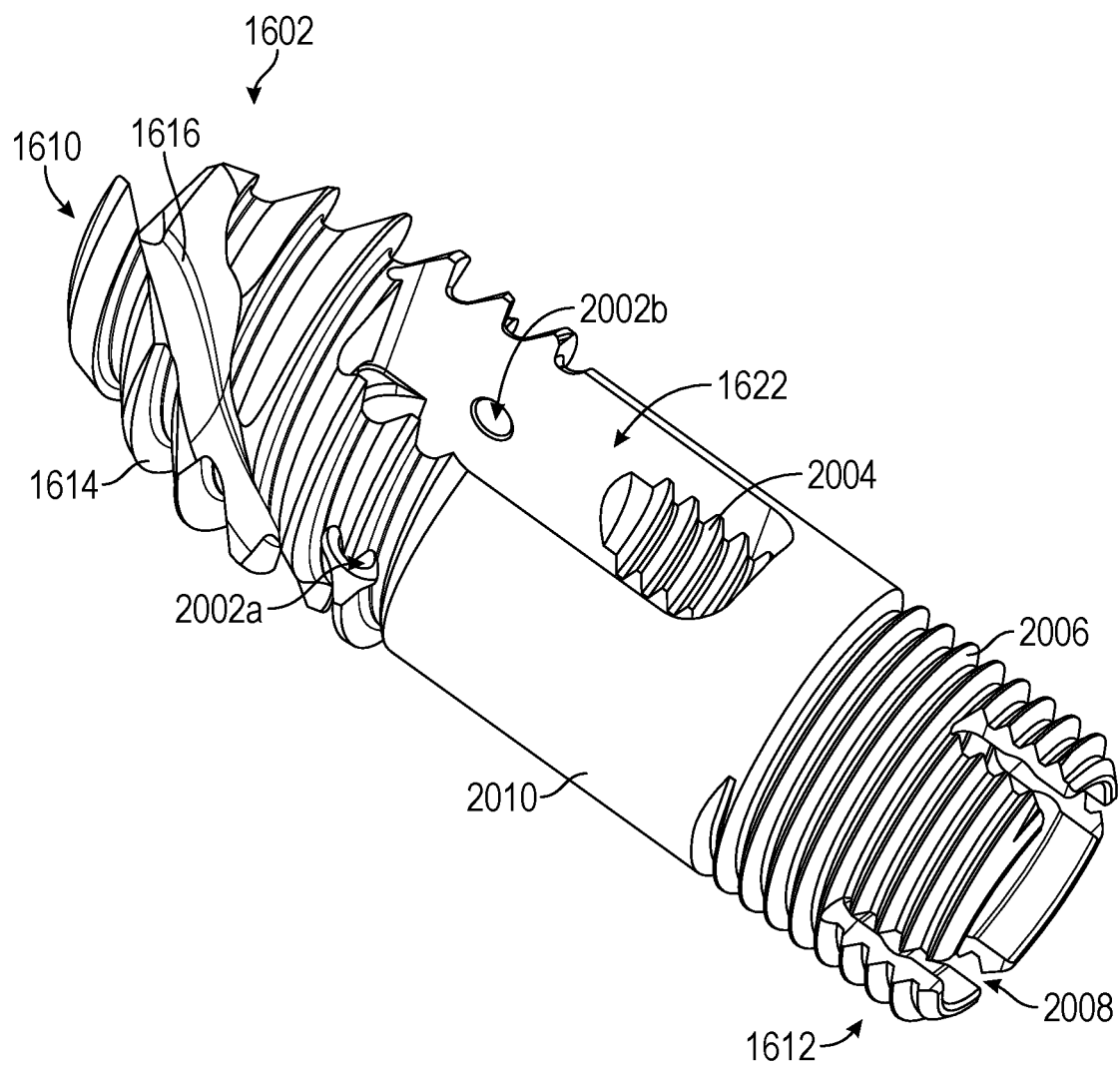
FIG. 20 illustrates a main body of the third embodiment.

FIG. 20 illustrates a perspective view of main body 1602 for some embodiments of the present disclosure. Main body may comprise distal end 1610 and proximal end 1612. Distal end 1610 may comprise threads 1614 and flutes 1616 for self-drilling implant 1600 into bone. Threads 1614 and flutes 1616 may extend proximally from a distal tip of distal end 1610 lengthwise about a third of the overall length of main body 1602. In some embodiments, threads 1614 and/or flutes 1616 extend lengthwise about 20% to about 50% an overall length of main body 1602.

Main body 1602 may also comprise a first opening 2002a and a second opening 2002b. First opening 2002a may receive first pin 1620a that is received within slot 1816 on first wing 1618a, and second opening 2002b may receive second pin 1620b that is received within slot 1816 on second wing 1618b. The use of two, separate pins instead of a single pin extending across window 1622 may allow for bore 1606 to remain unobstructed along longitudinal axis 1608 such that implant 1600 may be inserted over a guidewire and into the target space within a patient.

An inner surface of main body 102 may comprise internal threads 2004. Internal threads 2004 may be configured to mate with non-threaded portion 1904 on proximal plunger 1626. Accordingly, proximal plunger 1626 may be rotationally driven and move longitudinally due to the threaded engagement of the non-threaded portion 1904 with internal threads 2004. Longitudinal distal movement of proximal plunger 1626 may cause deployment of wings 1618a, 1618b, and longitudinal proximal movement of proximal plunger 1626 may cause retraction of wings 1618a, 1618b.

Proximal end 1612 may comprise external threads 2006. External threads 2006 may be configured to mate with internal threads on compressive body 1604 (see FIG. 21). Accordingly, compressive body 1604 may be threaded along external threads 2006 to apply compression to the SI joint 800 (via distal movement of compressive body 1604) or reduce compression to the SI joint 800 (via proximal movement of compressive body 1604). Proximal end 1612 may also comprise openings 2008. In some embodiments, proximal end 1612 comprises four openings 2008. In some embodiments, the openings 2008 are configured to mate with a corresponding feature on a distal tip of the insertion instrument (see FIG. 25B) Openings 2008 may also allow bone graft to flow around implant 1600 after placement of implant 1600 to promote bony fusion.

In some embodiments, main body 1602 comprises a central section 2010 extending between the threads 1614 on distal end 1610 and the external threads 2006 on proximal end 1612. Central section 2010 may aid in retracting implant 1600 to anchor wings 1618a, 1618b to the sacrum 804. In some embodiments, central section 2010 is substantially smooth. In some embodiments, central section 2010 is a non-threaded section of main body 1602 and may have a rough outer surface to promote bony fusion. It is contemplated that one or more openings may extend through central section 2010 to aid in self-harvesting bone, similar to openings 124 of implant 100.

Figure 21:
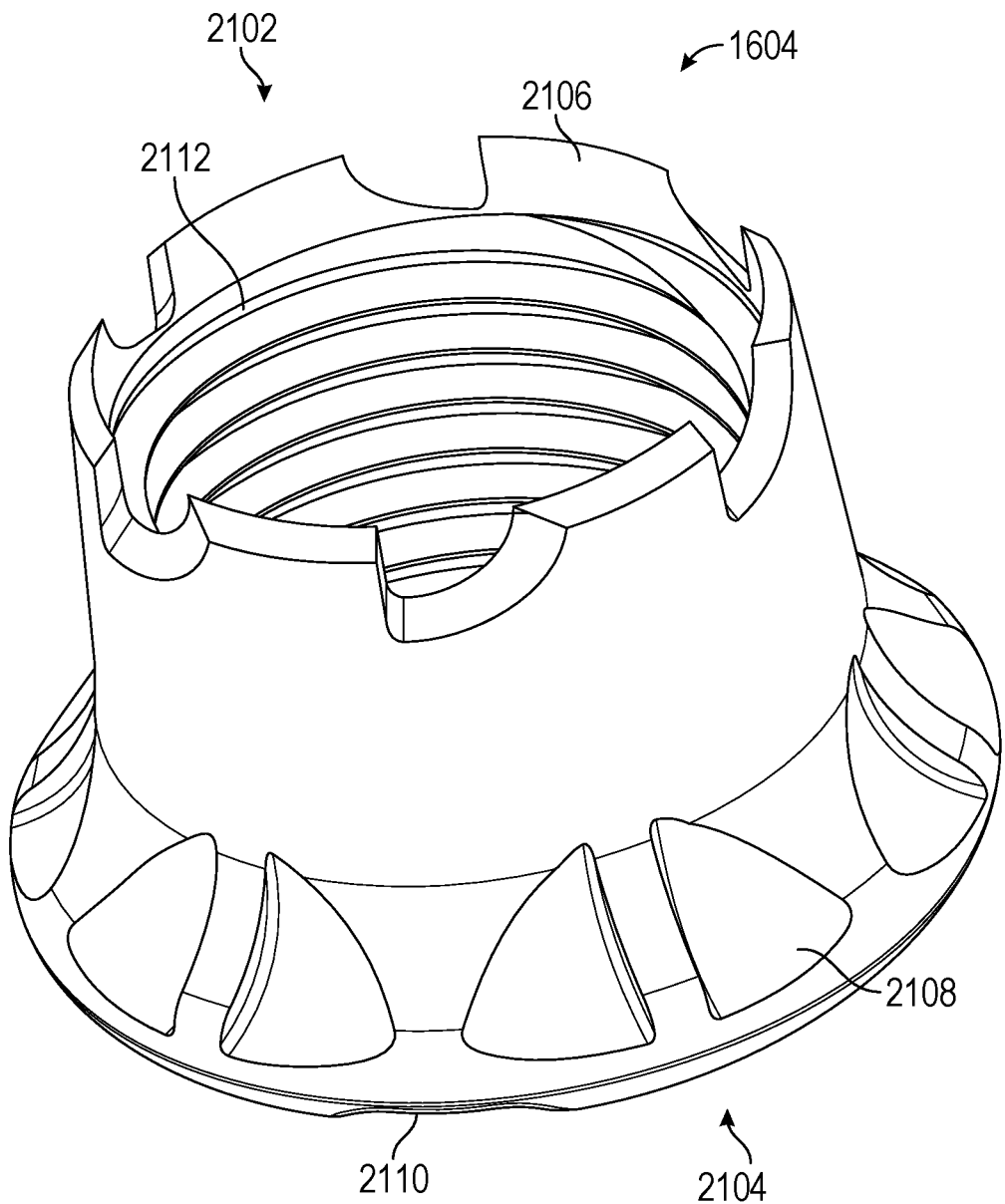
FIG. 21 illustrates a compressive body of the third embodiment.

FIG. 21 illustrates a perspective view of compressive body 1604 for some embodiments. Compressive body 1604 may comprise a distal end 2102 and a proximal end 2104. Distal end 2102 may be formed with teeth 2106 that may extend circumferentially around distal end 2102. In some embodiments, the teeth 2106 are sharp such that teeth 2106 help burrow compressive body 1604 into the ilium (e.g., at least partially embed into the ilium).

Proximal end 2104 may comprise one or more recesses 2108 extending circumferentially around proximal end 2104. In some embodiments, the one or more recesses 2108 may be substantially triangular shaped, although embodiments are not limited to a triangle shape. In some embodiments, the recesses 2108 are configured to prevent implant 1600 from bottoming out. That is, recesses 2108 help keep compressive body 1604 flush against the ilium 802. Recesses 2108 may also act as a counter rotating feature for implant 1600. As discussed above, the distal anchor (i.e., wings 1618a, 1618b) may also have fangs 1814 that act as an anti-rotational feature. Thus, rotation of implant 1600, when inserted, may be minimized by both wings 1618a, 1618b and compressive body 1604.

As seen best in FIG. 16C, a bottom surface of compressive body 1604 may comprise an annular array of receiving portions 2110. The receiving portions 2110 may be configured to cooperatively engage with a driver on the insertion instrument (see FIGS. 26A and 26B). Accordingly, the driver may rotationally drive compressive body 1604. Internal threads 2112 on compressive body 1604 may thread along external threads 2006 to move compressive body 1604 longitudinally.

Figure 22:
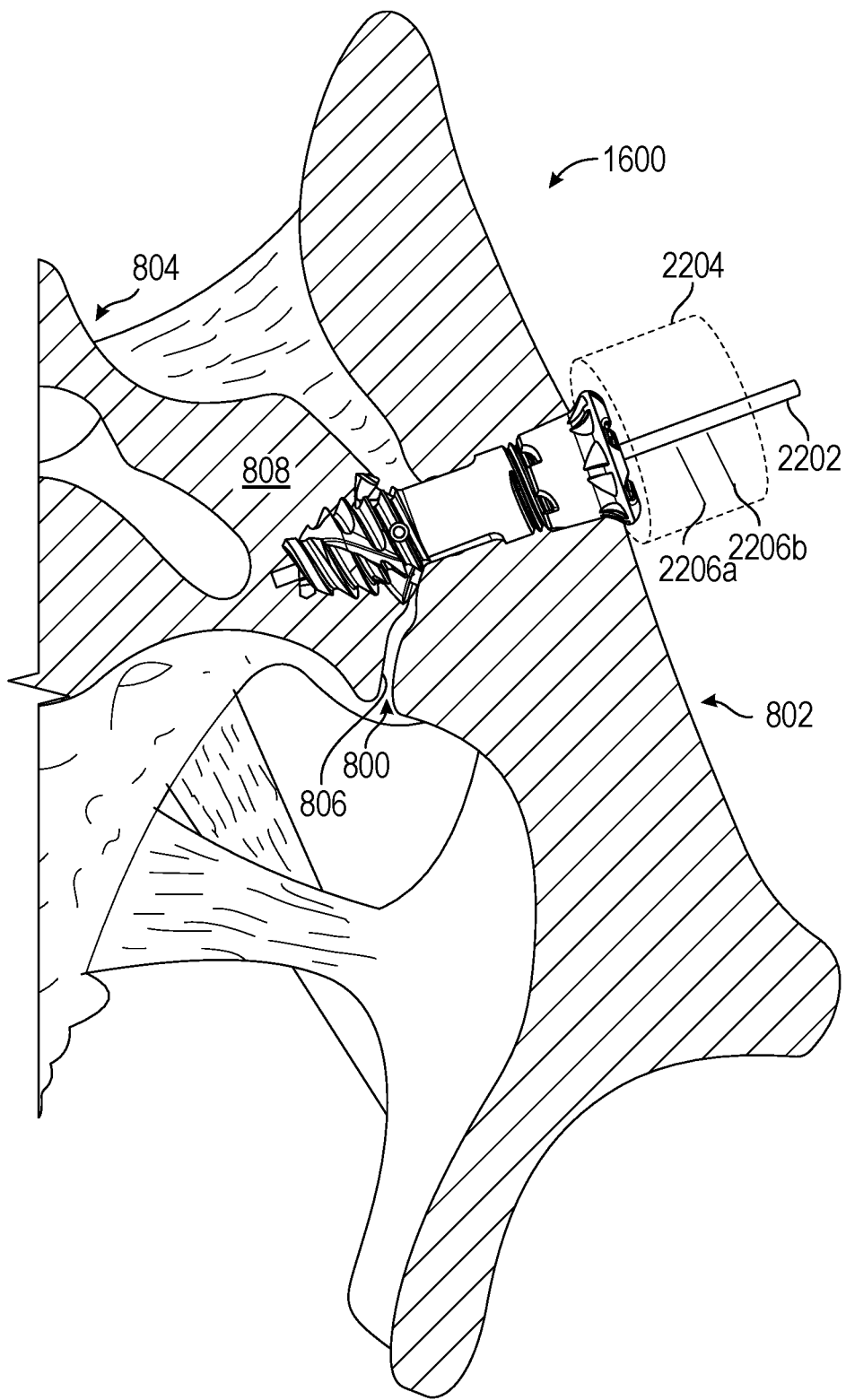
FIG. 22 illustrates the third embodiment inserted across the SI joint.

FIG. 22 illustrates implant 1600 inserted into a patient for some embodiments of the present disclosure. As discussed above with respect to FIGS. 8 and 15, implant 1600 may be inserted across the SI joint 800 to cause compression across the SI joint 800. Once a minimally invasive incision has been made, implant 1600 may be inserted as follows. A guidewire 2202 may be inserted through the incision and the ilium 802 and into the sacrum 804. In some embodiments, the guidewire 2202 is configured to be visible under fluoroscopy to allow the surgeon to view the guidewire 2202 in the patient's body. Next, one or more sleeves 2204 may be inserted over the guidewire 2202 to dilate and/or distract surrounding tissue. Each successive sleeve 2204 may be larger than a previous sleeve. As shown in FIG. 22, once a final, largest sleeve 2204 has been inserted, the smaller sleeves may be removed, leaving the guidewire 2202 and a single sleeve 2204 in place. The sleeves 2204 may be advanced against an outer surface of the ilium 802.

When the last sleeve 2204 is in place, implant 1600 may be inserted over the guidewire 2202. By "over the guidewire" it is meant that the guidewire 2202 is received within bore 1606. As discussed above, implants 100, 900, 1600 may have a central, longitudinal bore extending throughout the implant. The bore may be unobstructed such that the guidewire 2202 can be received therein without obstructing the movement of the other components that are moved to deploy the wings. When two or more implants 1600 are inserted across the SI joint 800, guidewires 2202 may be inserted using a parallel pin guidewire tool as is known to those of skill in the art.

Once the implant 1600 is inserted over the guidewire, the implant 1600 may be self-drilled into the sacrum 804. Distal end 1610 may comprise threads 1614 and flutes 1616 that are configured for self-drilling into bone. Accordingly, the operator, using the insertion instrument, may rotationally drive implant 1600 to self-drill the implant 1600 into the sacrum 804.

When the implant 1600 is in the target space, the wings 1618a, 1618b may be deployed to transition the implant 1600 from the open configuration (see, e.g., FIG. 9B) to the open configuration (see, e.g., FIG. 9A). Wings 1618a, 1618b may be deployed by longitudinal, distal movement of distal plunger 1624. This longitudinal, distal movement may be accomplished using the insertion instrument, which may be configured to drive non-threaded portion 1906 using a hex driver, for example. When non-threaded portion 1906 is rotationally driven in a first direction, threaded portion 1904 may thread along internal threads 2004 on main body 1602. Accordingly, longitudinal distal movement of distal plunger 1624 may be achieved, causing slots 1816 on wings 1618a, 1618b to move along pins 1620a, 1620b, thereby deploying the wings 1618a, 1618b. Likewise, rotating the non-threaded portion 1906 in a second direction that is opposite the first direction may cause longitudinal, proximal movement of distal plunger 1624, thereby retracting wings 1618a, 1618b within window 1622. In some embodiments, once wings 1618a, 1618b are deployed, implant 1600 is pulled proximally towards the operator to engage fangs 1814 with the cortical bone 806 of the sacrum 804. Fangs 1814 may provide a counter-rotational measure to prevent rotation of implant 1600 when implanted.

Lastly, with wings 1618a, 1618b deployed, the insertion instrument may be used to thread compressive body 1604 along main body 1602 to provide additional compression across SI joint 800. Threading compressive body 1604 distally along main body 1602 may add compression to the SI joint 800, while threading compressive body 1604 proximally along main body 1602 may reduce compression on the SI joint 800. In some embodiments, the insertion instrument has engaging features configured to couple with internal threads 2112 on main body 1602. Accordingly, the engaging features on the insertion instrument may engage with receiving portions 2110 such that the insertion instrument can rotationally drive main body 1602 along the outer threads 2006 on the proximal end 1612 of main body 1602.

As previously discussed, implant 1600 may be provided in various lengths. Accordingly, a surgeon may select an appropriate length of implant 1600 based on patient anatomy when performing the SI joint fusion operation. In some embodiments, the length of implant 1600 needed can be determined using the guidewire 2202. In some embodiments, the guidewire 2202 comprises one or more marking holes that indicate a length of the guidewire 2202 at the location of each of the marking holes. Thus, the surgeon can view the guidewire 2202 within the patient (i.e., under fluoroscopy) to determine the length that guidewire 2202 is inserted into the patient. The length of implant 1600 may then be selected accordingly. In some embodiments, the implant size can be determined based on a distance between sleeve 2204 that is docked against an outer surface of ilium 802 and the marking hole on the guidewire 2202.

First Insertion Instrument

Figure 23C:
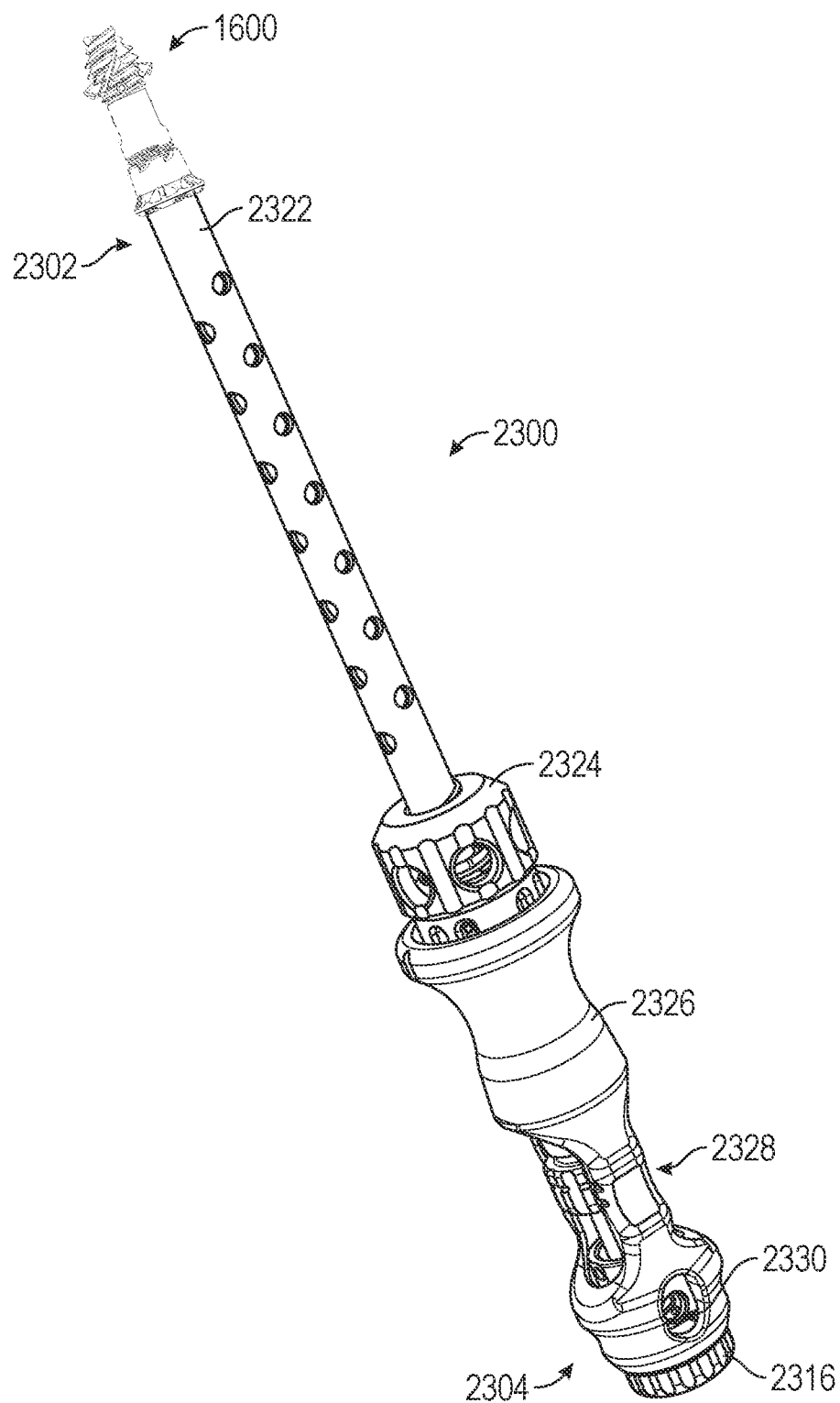
FIG. 23C illustrates the insertion instrument coupled to the third implant embodiment.

FIGS. 23A and 23B illustrate a planar view and a cross-sectional view, respectively, of an insertion instrument 2300 for some embodiments of the present disclosure. FIG. 23C illustrates insertion instrument 2300 coupled to implant 1600 for some embodiments. Insertion instrument 2300 may be configured to perform three actions for insertion and implantation of implant 1600: (1) insert the implant 1600 into the sacrum 804; (2) deploy the wings 1618a, 1618b; and (3) adjust the position of compressive body 1604 to apply the desired compression across SI joint 800. While insertion instrument 2300 is described herein with respect to use with implant 1600, it will be appreciated that insertion instrument 2300 may also be used for insertion and implantation of implants 100, 900.

Insertion instrument 2300 may comprise a distal end 2302 and a proximal end 2304. As seen in FIG. 23C, implant 1600 may couple to insertion instrument 2300 at distal end 2302. A bore 2306 may extend along a longitudinal axis 2308 of insertion instrument 2300. Like bore 1606 described above, bore 2306 may be unobstructed along longitudinal axis 2308 such that insertion instrument 2300 may be inserted over guidewire 2202. When insertion instrument 2300 is coupled to implant 1600, longitudinal axis 1608 and longitudinal axis 2308 may be coaxial. Accordingly, the guidewire 2202 may be inserted (e.g., tapped) into sacrum 804, implant 1600 may be coupled to insertion instrument 2300, and both implant 1600 and insertion instrument 2300 may be placed over the guidewire 2202 with guidewire 2202 extending through bores 1606, 2306. Bore 2306 may extend entirely through insertion instrument 2300 such that guidewire 2202 may extend out of proximal end 2304.

Insertion instrument 2300 may further comprise a rod assembly 2400 (see FIGS. 24A and 24B) comprising a rod 2310, a rod handle 2312, a rod spring 2314, a rod spring stop 2316; a first shaft assembly 2500 (see FIGS. 25A and 25B) comprising a shaft 2318 and a shaft handle core 2320; and a second shaft assembly 2600 (see FIGS. 26A and 26B) comprising a compressive body shaft 2322 and a shaft handle 2324. An outer handle 2326 may interface with shaft handle core 2320. Outer handle 2326 may define a window 2328 providing access to rod handle 2312. One or more holes 2330 may extend through outer handle 2326 for weight reduction and/or cleanability of insertion instrument 2300. As shown in FIG. 23B, rod 2310 may extend through shaft 2318, and shaft 2318 may extend through compressive body shaft 2322. Accordingly, rod 2310 may have an outer diameter (or width) that is smaller than an inner diameter (or width) of shaft 2318, and shaft 2318 may have an outer diameter (or width) that is smaller than an inner diameter (or width) of compressive body shaft 2322. Rod 2310 may have an inner diameter (or width) sized to receive guidewire 2202 therein. The inner diameter of rod 2310 may thus define the diameter of bore 2306.

In some embodiments, rod 2310 is configured to deploy wings 1618a, 1618b. In some embodiments, shaft 2318 is configured to rotate implant 1600 for self-drilling implant 1600 into the patient. In some embodiments, compressive body shaft 2322 is configured to move compressive body 1604 longitudinally along main body 1602. Rod 2310 may couple to proximal plunger 1626, shaft 2318 may couple to proximal end 1612, and compressive body shaft 2322 may couple to compressive body 1604. Operation of insertion instrument 2300 to insert implant 1600 may proceed as follows. Once insertion instrument 2300 is coupled to implant 1600, shaft 2318 may be rotated and advanced distally using outer handle 2326 to rotate and self-drill implant 1600 through the ilium 802 and into the sacrum 804. Next, rod 2310 may be rotated and advanced distally using rod handle 2312 to rotate proximal plunger 1626, thereby deploying wings 1618a, 1618b into cancellous bone 808. Lastly, compressive body shaft 2322 may be rotated using shaft handle 2324 to thread compressive body 1604 to the desired location along proximal end 1612. In some embodiments, rod 2310, shaft 2318, and compressive body shaft 2322 are each coupled to proximal plunger 1626, proximal end 1612, and compressive body 1604, and each rod 2310, shaft 2318, and compressive body shaft 2322 are successively actuated to perform their respective action while the other components remain coupled to their respective components on implant 1600. In some embodiments, shaft 2318 is first coupled to proximal end 1612 to self-drill implant 1600 into sacrum 804, then decoupled from proximal end 1612 before coupling rod 2310 to proximal plunger 1626 to deploy wings 1618a, 1618b. Likewise, rod 2310 may be decoupled from proximal plunger 1626 before coupling compressive body shaft 2322 to compressive body 1604 to adjust compressive body 1604.

Figure 24A:
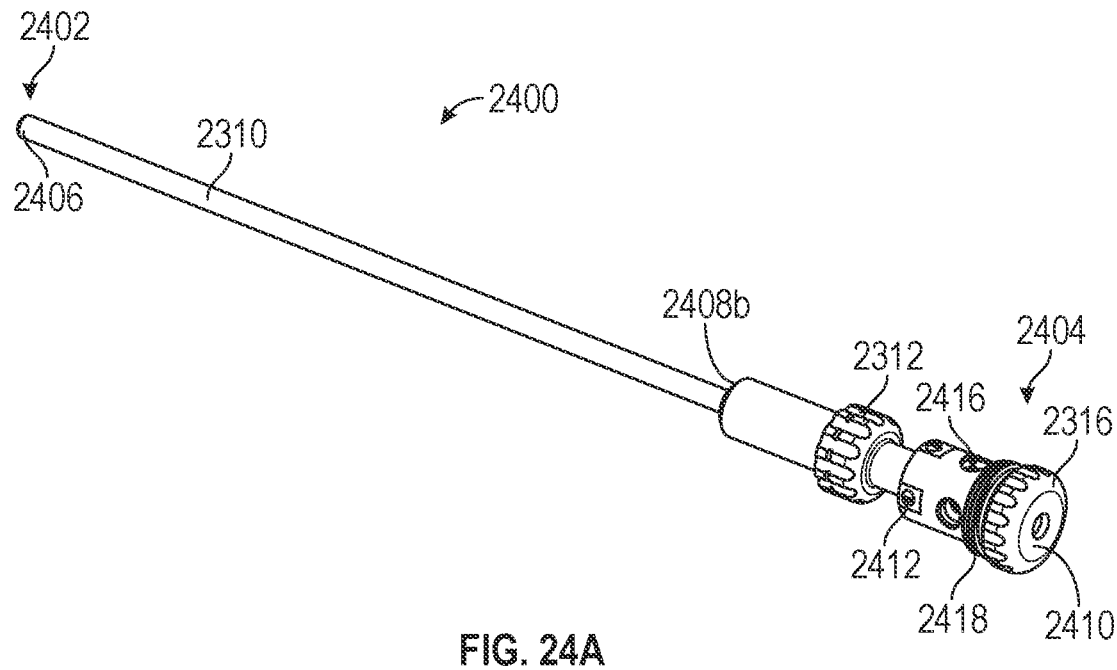
FIG. 24A illustrates a rod assembly of the insertion instrument for some embodiments.
Figure 24B:
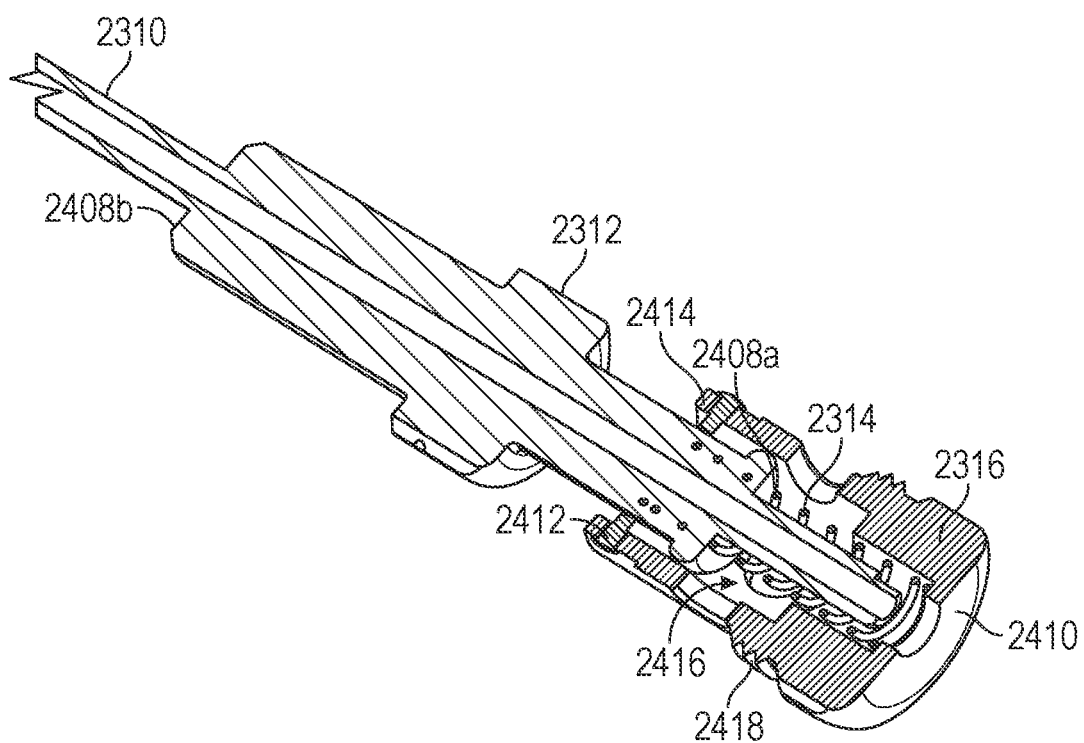
FIG. 24B illustrates a cross-sectional view of the rod assembly for some embodiments.

FIG. 24A illustrates a perspective view of rod assembly 2400, and FIG. 24B illustrates a close-up cross-sectional view of a proximal end of rod assembly 2400 for some embodiments of the present disclosure. Rod assembly 2400 may comprise rod 2310, rod handle 2312, rod spring 2314, and rod spring stop 2316. Rod assembly 2400 may further have a distal end 2402, and a proximal end 2404. A distal tip 2406 may be located at distal end 2402, and rod handle 2312, rod spring 2314, and rod spring stop 2316 may be located at proximal end 2404. Bore 2306 may extend through rod 2310, from distal end 2402 and through proximal end 2404 such that rod 2310 presents a hollow body. In some embodiments, distal tip 2406 is formed as a hex socket for coupling to the hex-shaped non-threaded portion 1906 on proximal plunger 1626. Generally, distal tip 2406 may take any shape for coupling to non-threaded portion 1906 to rotationally drive proximal plunger 1626.

Rod handle 2312 may be rotated by an operator to rotate rod 2310, thereby rotating non-threaded portion 1906. Rotation of non-threaded portion 1906 may cause threaded portion 1904 to thread along internal threads 2004 of main body 1602, thereby retracting or deploying wings 1618a, wings 1618b. An axial force, applied substantially along longitudinal axis 2308, may also be applied to move rod assembly 2400 longitudinally. Rod assembly 2400 may be spring-loaded with rod spring 2314. In some embodiments, rod handle 2312 is formed with ridges, bumps, or other features to enhance the grip of the operator.

As shown in FIG. 24B, rod spring 2314 may be housed within rod spring stop 2316, and a proximal end 2408a of rod handle 2312 may be at least partially received within rod spring stop 2316. Accordingly, a proximal end 2410 of rod spring stop 2316 and proximal end 2408a of rod handle 2312 limit the travel of rod spring 2314. In some embodiments, rod assembly 2400 comprises one or more pins 2412 extending through a distal end 2414 of rod spring stop 2316 that retain proximal end 2408a of rod handle 2312 within rod spring stop 2316. For example, proximal end 2408a may have a flanged portion abutting pins 2412 to prevent rod handle 2312 from sliding out of rod spring stop 2316. Rod spring stop 2316 may further comprise one or more radial holes 2416 therethrough. The holes 2416 may enhance cleanability of rod assembly 2400, along with reducing the weight of rod assembly 2400. In some embodiments, rod spring stop 2316 comprises threads 2418 that threadedly engage with internal threads on outer handle 2326.

Figure 25A:
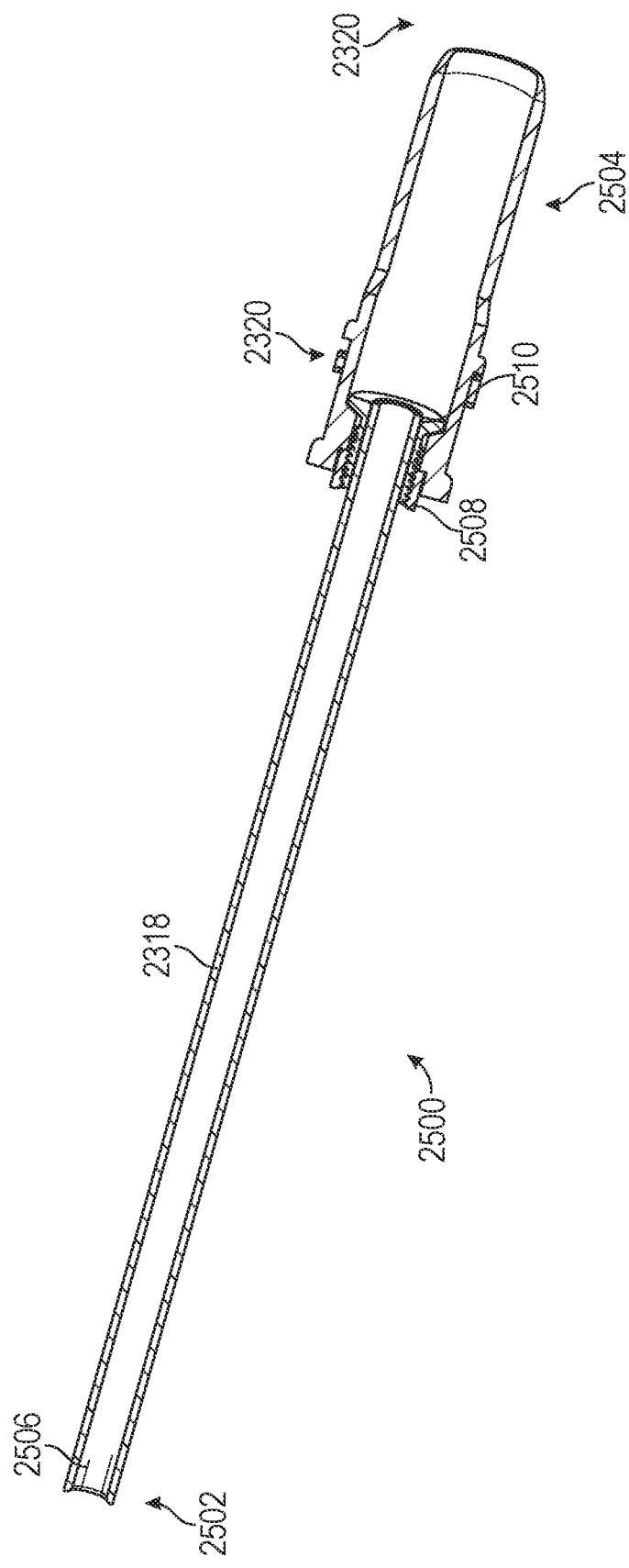
FIG. 25A illustrates a cross-sectional view of a first shaft assembly of the insertion instrument for some embodiments.
Figure 25B:
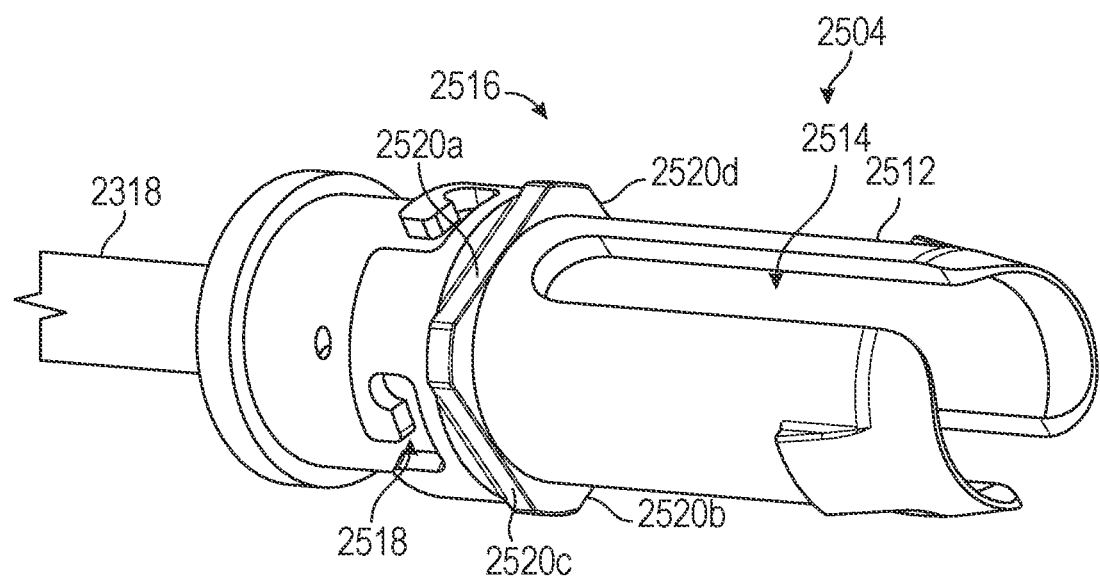
FIG. 25B illustrates a proximal end of the first shaft assembly for some embodiments.
Figure 25C:
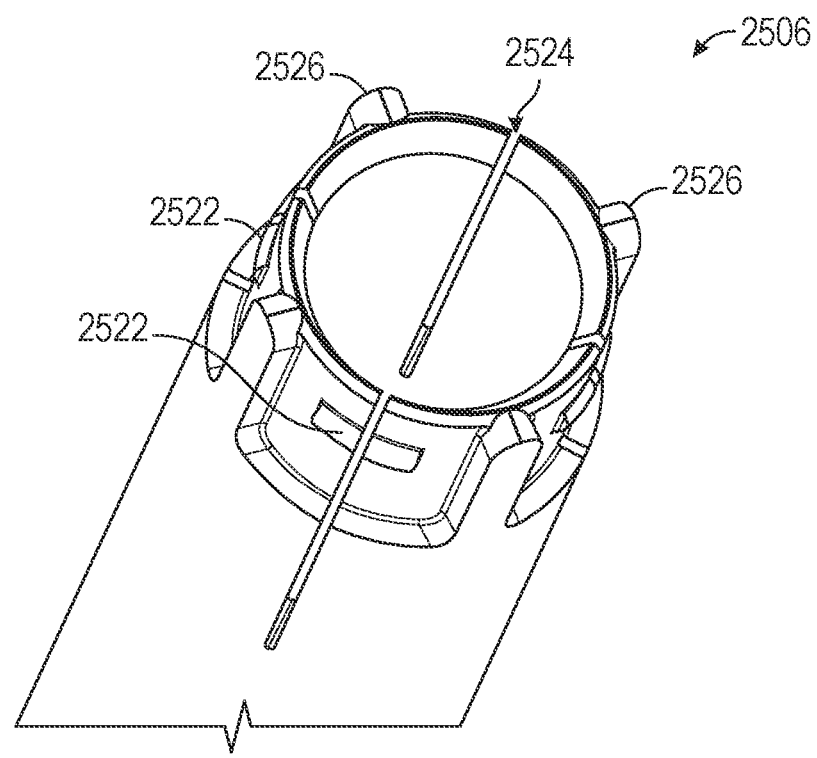
FIG. 25C illustrates a distal tip of a shaft of the first shaft assembly for some embodiments.

FIG. 25A illustrates a cross-sectional view of a first shaft assembly 2500 (also referred to as a spanner shaft assembly), FIG. 25B illustrates a close-up view of a proximal end of first shaft assembly 2500, and FIG. 25C illustrates a close-up view of a distal tip of shaft 2318 for some embodiments of the present disclosure. Spanner shaft assembly 2500 may comprise shaft 2318, shaft handle core 2320, a distal end 2502, and a proximal end 2504. A distal tip 2506 of shaft 2318 may be located at distal end 2502. Distal tip 2506 may couple to proximal end 1612 as discussed further below with respect to FIG. 25C. A nut 2508 may be coupled to (e.g., threadedly engaged) a sleeve 2510, and shaft 2318 may be at least partially received within sleeve 2510. Nut 2508 and sleeve 2510 may be at least partially received within shaft handle core 2320.

As shown in FIG. 25B, shaft handle core 2320 may comprise opposing tabs 2512 defining openings 2514 therebetween, an index 2516, and slots 2518. Tabs 2512 may be flexible such that tabs 2512 may be compressed to slide second shaft assembly 2600 on/off of first shaft assembly 2500. Slots 2518 may receive pins of second shaft assembly 2600 therein (see FIGS. 26A and 26B), and when tabs 2512 are compressed, second shaft assembly 2600 may be decoupled from first shaft assembly 2500 by moving the pins out of slots 2518. Slots 2518 may be J-slots or any other similar locking mechanism as will be appreciated by one of skill in the art. Tabs 2512 may also define a receiving area for receiving distal end 2408b of rod assembly 2400. When distal end 2408b is within the receiving area (as shown in FIG. 23B), tabs 2512 may be prevented from being compressed such that the assemblies 2400, 2500, 2600 are locked together.

Index 2516 may provide an indexing feature that prevents first shaft assembly 2500 from being locked with tabs 2512 in a position that is difficult to access via window 2328. Turning back to FIG. 23B, it can be seen that rotating tabs 2512 ninety degrees from the illustrated position makes tabs 2512 difficult to access via window 2328. Accordingly, index 2516 may be configured to prevent locking of first shaft assembly 2500 when the tabs 2512 are rotated such that openings 2514 are in line with window 2328. In some embodiments, index 2516 comprises a generally rectangular shape, with a first side 2520a, a second side 2520b opposing first side 2520a, a third side 2520c, and a fourth side 2520d. A first distance between opposing sides 2520a, 2520b may be different from a second distance between opposing sides 2520c, 2520d. Accordingly, the differing lengths provide an indexing feature that prevents shaft handle core 2320 from being locked because the tabs 2512 may not engage with the corresponding receiving portion within outer handle 2326.

FIG. 25C illustrates distal tip 2506 for some embodiments of the present disclosure. As shown, distal tip 2506 comprises a plurality of detents 2522 circumferentially around the tip. Distal tip 2506 may also comprise a plurality of tangs 2524 bisecting each of the detents 2522. The detents 2522 may interface with receiving portions 2110 on the inner surface of main body 1602. Tangs 2524 may be configured to provide additional flexure (e.g., radial flexure) in distal tip 2506, which may aid in coupling distal tip 2506 to proximal end 1612. Distal tip 2506 may further comprise a plurality of cutouts 2526, with each cutout 2526 disposed between adjacent detents 2522 on the exterior of distal tip 2506. The cutouts 2526 may be received within openings 2008 on proximal end 1612. Accordingly, distal tip 2506 may couple to proximal end 1612 of main body 1602 with detents 2522 engaging recesses 2012 (see FIG. 16B) and cutouts 2526 fitting in the openings 2008. Once coupled, shaft 2318 may be rotationally driven, using shaft handle core 2320, to rotate implant 1600 for inserting implant 1600 into the patient. The self-drilling features at distal end 1610 may then self-drill implant 1600 through ilium 802 and into the sacrum 804. As shown in FIG. 25A, shaft handle core 2320 may have a contoured body configured to provide a comfortable grip for the operator.

Figure 26A:
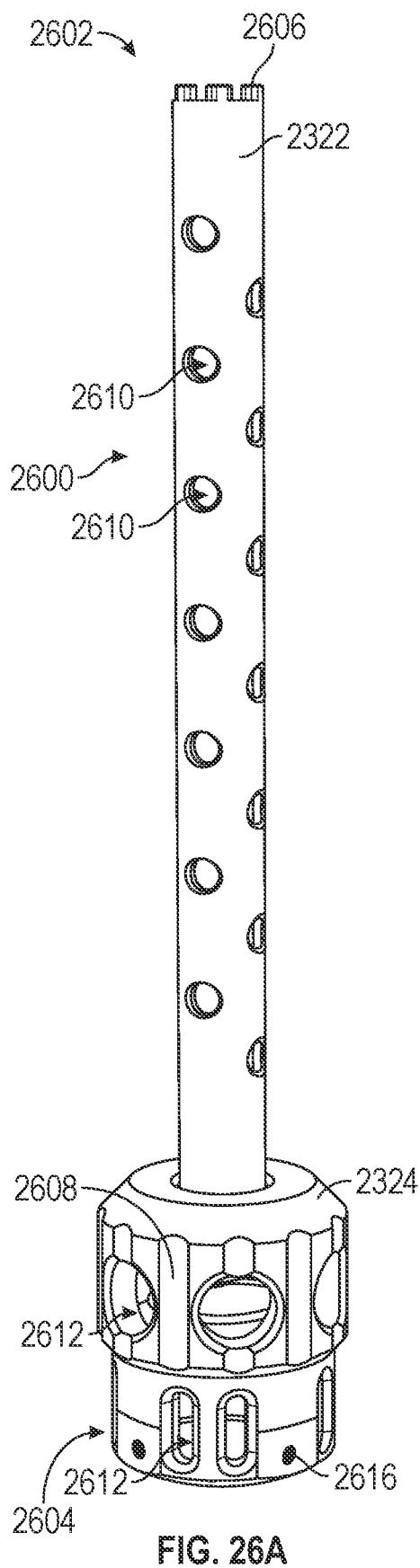
FIG. 26A illustrates a second shaft assembly of the insertion instrument for some embodiments.
Figure 26B:
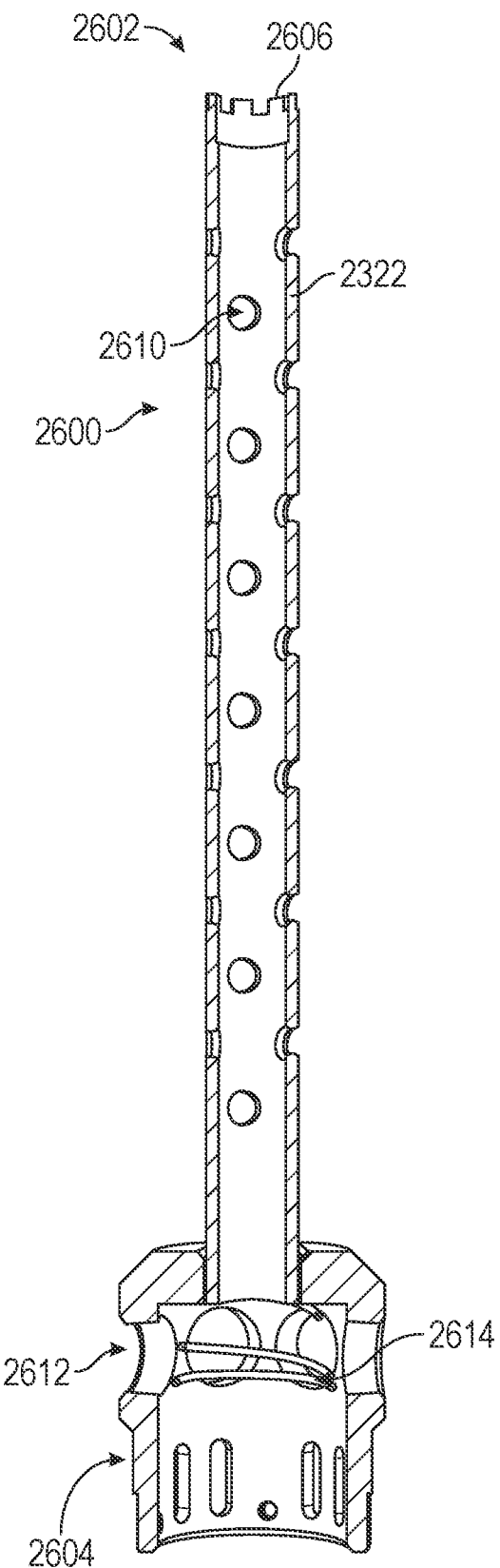
FIG. 26B illustrates a cross-sectional view of the second shaft assembly for some embodiments.

FIGS. 26A and 26B illustrate a planar view and a cross-sectional view, respectively, of a second shaft assembly 2600 for some embodiments of the present disclosure. Second shaft assembly 2600 may comprise compressive body shaft 2322, shaft handle 2324, a distal end 2602, and a proximal end 2604. As discussed above, second shaft assembly 2600 may couple to compressive body 1604 and may rotate compressive body 1604 to thread compressive body 1604 along main body 1602. In some embodiments, compressive body shaft 2322 comprises a distal tip 2606 configured to couple with receiving portions 2110 on compressive body 1604. The distal tip 2606 may be received within receiving portions 2110, and compressive body shaft 2322 may be rotated to rotate compressive body 1604. In some embodiments, the distal tip 2606 is a castle nut. Shaft handle 2324 may be coupled to compressive body shaft 2322 and rotated to rotate compressive body shaft 2322. Shaft handle 2324 may comprise grip features 2608 to enhance the operator's grip thereon. The grip features 2608 may be ridges, bumps, knurling, recesses, a checkered pattern, or the like. Compressive body shaft 2322 may also comprise a plurality of holes 2610 extending along a length thereof. The holes may provide weight reduction for compressive body shaft 2322, along with easing the cleanability for insertion instrument 2300. Likewise, shaft handle 2324 may comprise a plurality of holes 2612 for weight reduction and cleanability. Holes 2610, 2612 may be circular, rectangular, stadium-shaped, or any other geometrical shape.

As shown in FIG. 26B, a spring 2614 may be received within shaft handle 2324. Spring 2614 may bias the longitudinal movement of first shaft assembly 2500 within shaft handle 2324. Shaft handle 2324 may also comprise fastener holes 2616 for receiving a fastener therein (e.g., pin, screw, bolt, etc.) to affix second shaft assembly 2600 to first shaft assembly 2500.

It is contemplated that each of the above-described components of insertion instrument 2300 may be removable therefrom. Accordingly, each component may be replaceable in the event of damage and/or for cleaning purposes. For example, distal tip 2506 may be a removable, single use component such that a new distal tip 2506 is used with insertion instrument 2300 each time the surgical procedure is performed.

Second Insertion Instrument

FIGS. 27A and 27B illustrate a planar view and a cross-sectional view, respectively, of an insertion instrument 2700 for some embodiments of the present disclosure. As with insertion instrument 2300 discussed above, insertion instrument 2700 may be configured to: (1) insert the implant 1600 into the sacrum 804; (2) deploy the wings 1618a, 1618b; and (3) adjust the position of compressive body 1604 to apply the desired compression across SI joint 800. Insertion instrument 2700 may be used with any of implants 100, 900, 1600.

Insertion instrument 2700 may comprise a distal end 2702 and a proximal end 2704. Insertion instrument 2700 may couple to an implant 1600 at distal end 2702. A bore 2706 may extend along a longitudinal axis 2708 of 2700. Bore 2706 may be unobstructed along longitudinal axis 2708 to allow for insertion of 2700 over a guidewire 2202. When insertion instrument 2700 is coupled to implant 1600, longitudinal axis 1608 and longitudinal axis 2708 may be coaxial such that implant 1600 may be inserted across SI joint 800 using insertion instrument 2700 as discussed above with respect to insertion instrument 2300. Insertion instrument 2700 may also comprise a handle 2710.

Figure 29:
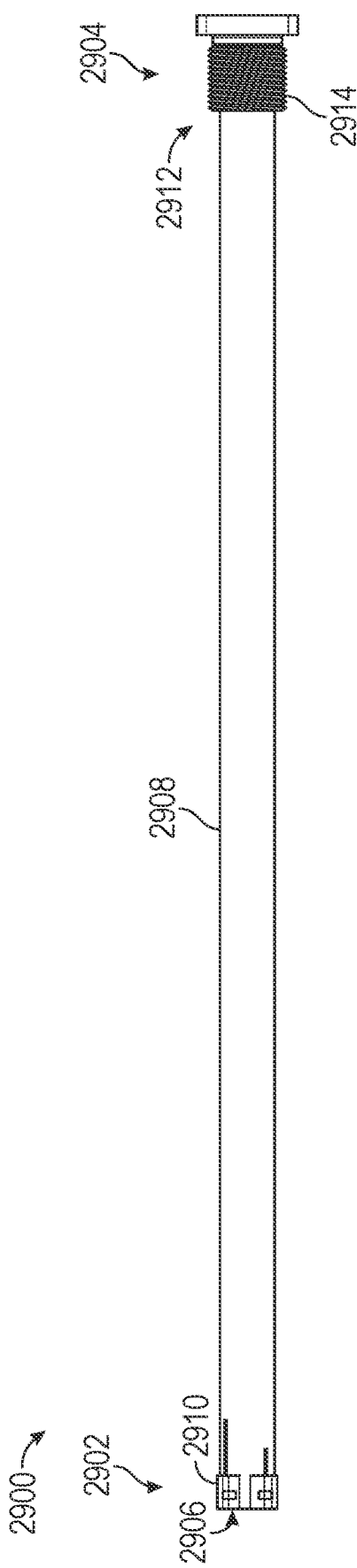
FIG. 29 illustrates a first shaft assembly of the second insertion instrument for some embodiments.
Figure 30A:
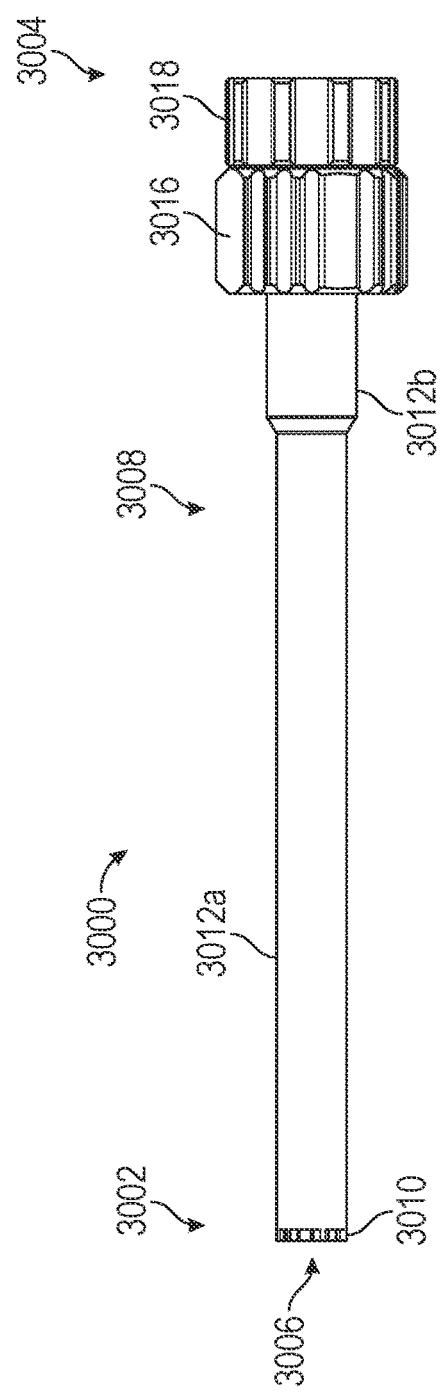
FIG. 30A illustrates a second shaft assembly of the second insertion instrument for some embodiments.
Figure 30B:
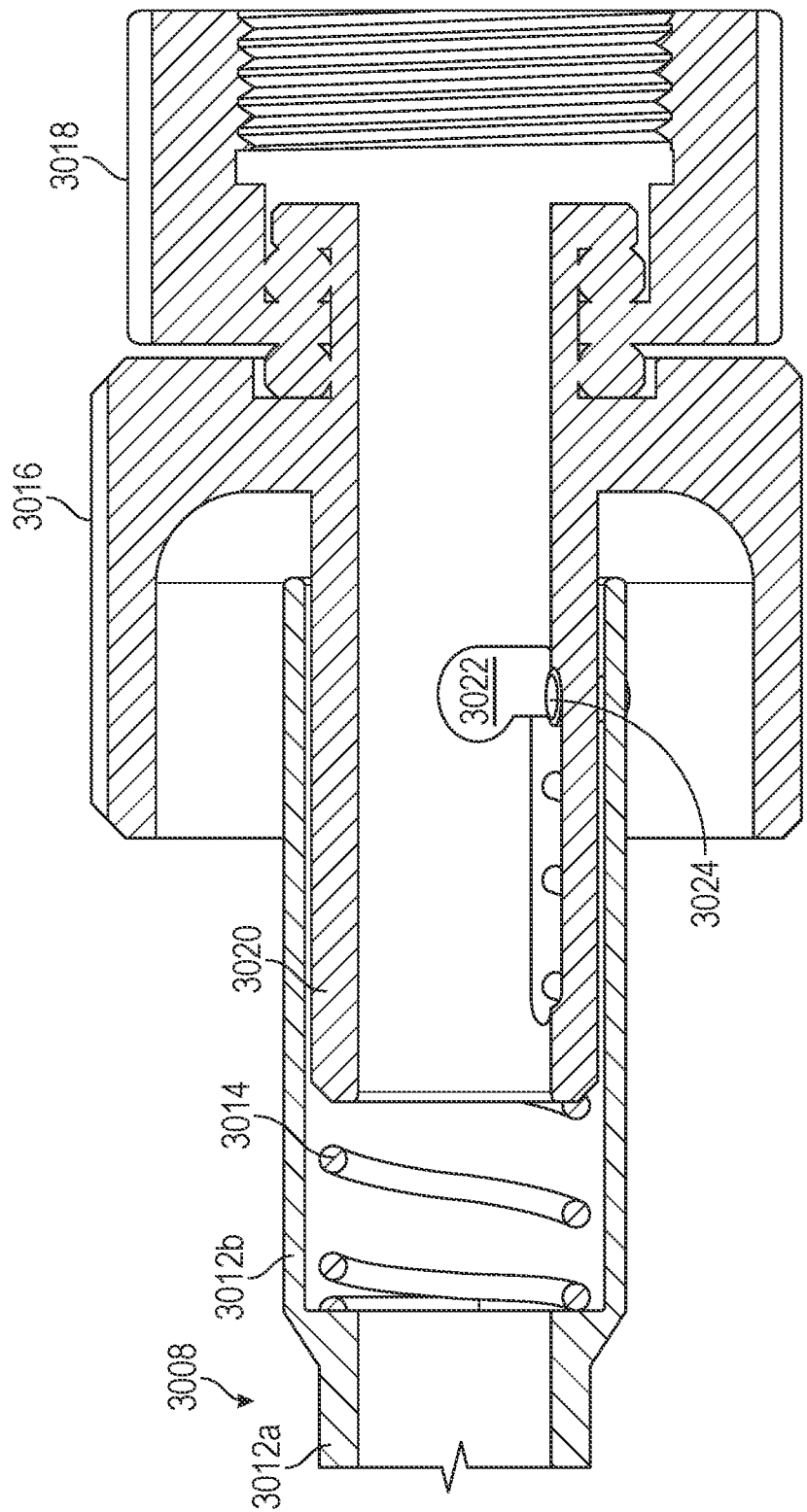
FIG. 30B illustrates a cross-sectional view of the second shaft assembly for some embodiments.

Insertion instrument 2700 may further comprise a rod assembly 2800 (see FIGS. 28A and 28B), a first shaft assembly 2900 (see FIG. 29), and a second shaft assembly 3000 (see FIGS. 30A and 30B). Rod assembly 2800 may be received within first shaft assembly 2900, and first shaft assembly 2900 may be received within second shaft assembly 3000. Rod assembly 2800 may have a bore therethrough such that guidewire 2202 may be received within rod assembly 2800.

In some embodiments, rod assembly 2800 is configured to deploy wings 1618a, 1618b and may be coupled to proximal plunger 1626. In some embodiments, first shaft assembly 2900 is configured to rotate implant 1600 for self-drilling implant 1600 into the patient and may be coupled to proximal end 1612. In some embodiments, second shaft assembly 3000 is configured to move compressive body 1604 longitudinally along main body 1602 and may be coupled to compressive body 1604. Operation of insertion instrument 2700 to insertion implant 1600 across SI joint 800 may proceed as follows. Once insertion instrument 2700 is coupled to implant 1600, first shaft assembly 2900 may be rotated and advanced distally to rotate and self-drill implant 1600 through ilium 802 and into sacrum 804. Insertion instrument 2700 may comprise a handle 2710 rotatable to drive first shaft assembly 2900. Next, rod assembly 2800 may be rotated and advanced distally to rotate proximal plunger 1626, thereby deploying wings 1618a, 1618b into cancellous bone 808. Lastly, second shaft assembly 3000 may be rotated to thread compressive body 1604 to the desired location along proximal end 1612. As discussed above with respect to insertion instrument 2300, rod assembly 2800, first shaft assembly 2900, and second shaft assembly 3000, may be coupled to implant 1600 and successively actuated for insertion of implant 1600 or each of rod assembly 2800, first shaft assembly 2900, second shaft assembly 3000 may be coupled to the respective component on implant 1600 for actuation thereof and then decoupled before coupling the next assembly for performing the respective function.

Figure 27C:
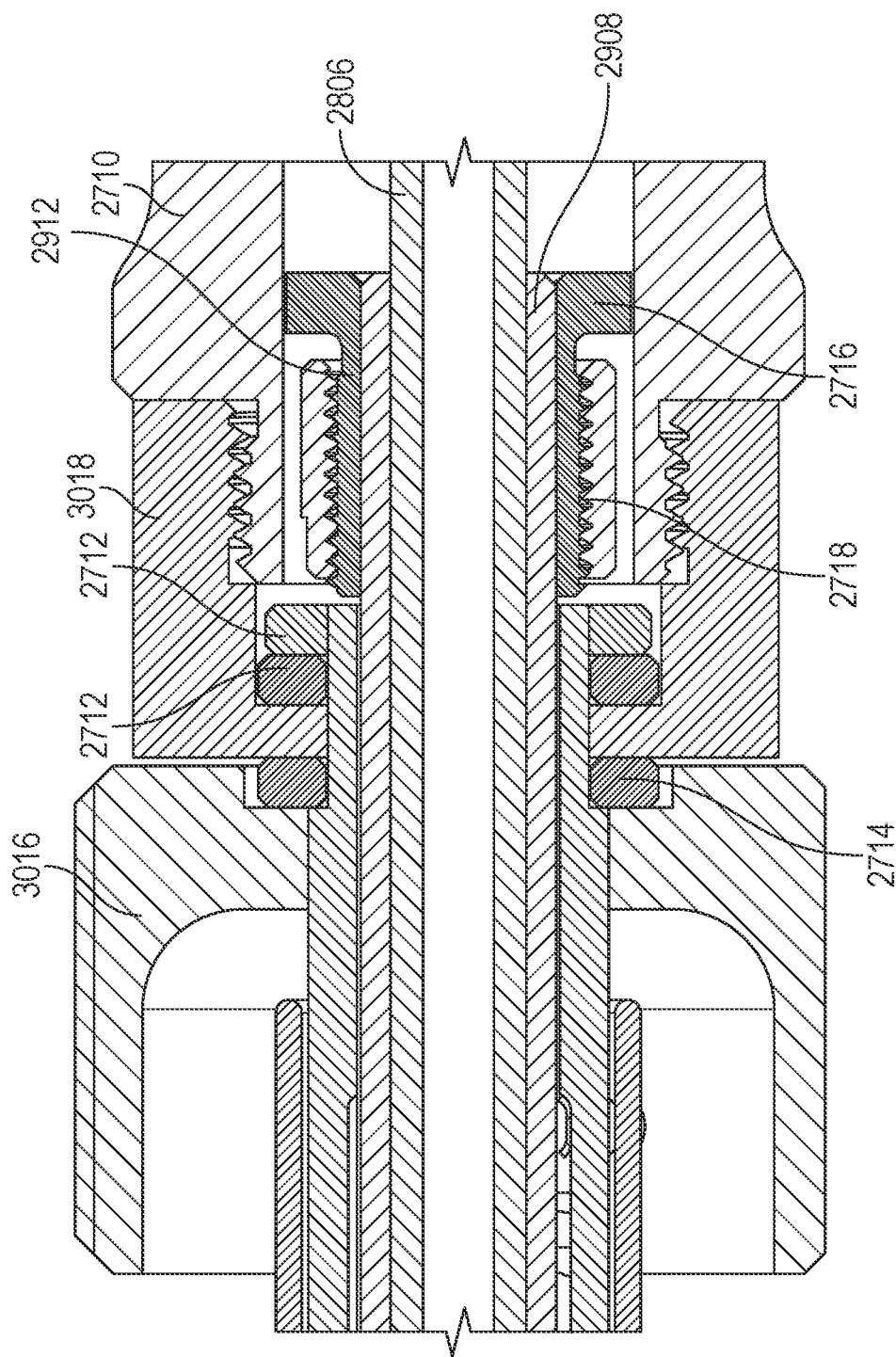
FIG. 27C illustrates a close-up cross-sectional view of the second insertion instrument for some embodiments.

FIG. 27C illustrates a close-up view of the interface between rod assembly 2800, first shaft assembly 2900, and second shaft assembly 3000 for some embodiments of the present disclosure. As shown, a distal end of handle 2710 may comprise external threads that interface with a second handle 3018 of second shaft assembly 3000 (see FIGS. 30A and 30B). One or more bearings 2712 may allow for second handle 3018 to rotate. Rotation of handle 2710 may control rotation of first shaft assembly 2900. Similarly, a bearing 2714 may be provided, allowing a first handle 3016 of second shaft assembly 3000 to be rotated to rotate second shaft assembly 3000.

Within handle 2710, a first threaded sleeve 2716 may be received and may be threadedly engaged with a second threaded sleeve 2718. A collar 2912 of a shaft 2908 of first shaft assembly 2900 (see FIG. 29) may be received within first threaded sleeve 2716, and a rod 2806 (see FIGS. 28A and 28B) may be received within shaft 2908, as shown. First threaded sleeve 2716 may be engaged with handle 2710 such that rotation of handle 2710 rotates first threaded sleeve 2716 to thereby rotate shaft 2908.

Figure 28A:
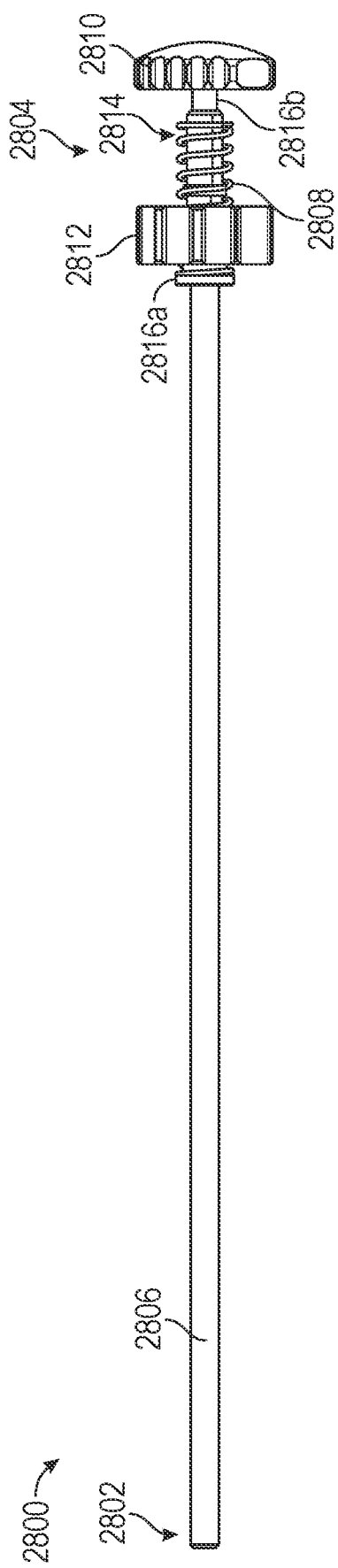
FIG. 28A illustrates a rod assembly of the second insertion instrument for some embodiments.
Figure 28B:
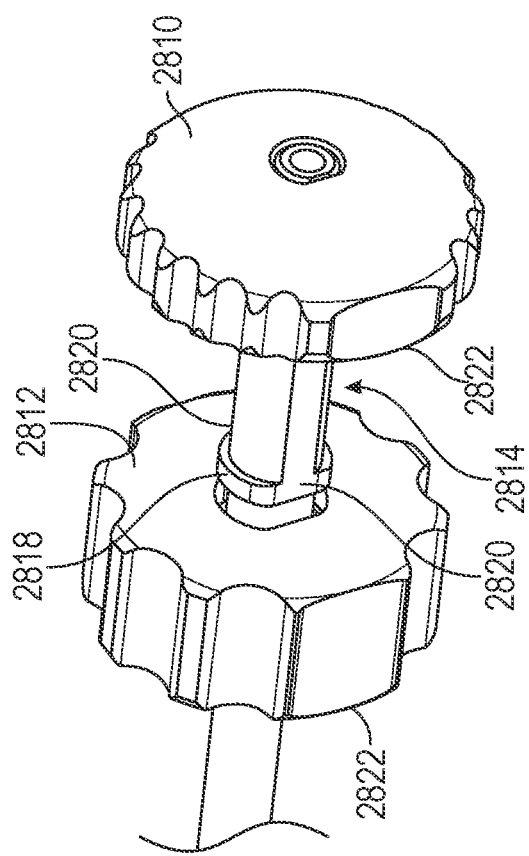
FIG. 28B illustrates a proximal end of the rod assembly for some embodiments.

Turning now to FIGS. 28A and 28B, rod assembly 2800 is illustrated for some embodiments of the present disclosure. Rod assembly 2800 may have a distal end 2802, a proximal end 2804, and define a bore extending from distal end 2802 to proximal end 2804 corresponding to bore 2706 for receiving guidewire 2202 as discussed above. A rod 2806 may extend from distal end 2802 to proximal end 2804. At distal end 2802, rod 2806 may be configured to couple to proximal plunger 1626 for deployment of wings 1618a, 1618b. Rod assembly 2800 may have a spring 2808 configured to bias the movement of handle 2810 to help maintain distal pressure and engagement of proximal end 2804 with proximal plunger 1626.

FIG. 28B illustrates a close-up view of proximal end 2804. As shown, rod assembly 2800 may comprise a handle 2810 that may be moved along longitudinal axis 2708 to move rod 2806 longitudinally, with distal movement of rod 2806 causing deployment of wings 1618a, 1618b, and proximal movement of rod 2806 causing retraction of wings 1618a, 1618b.

Rod assembly 2800 may further comprise a collar 2812 and a locking component 2814. Collar 2812 may be located distally from handle 2810. Locking component 2814 may have a distal end 2816a located distally from collar 2812 and a proximal end 2816b located between collar 2812 and handle 2810. Distal end 2816a may have a larger diameter than an inner diameter of collar 2812 such that locking component 2814 is prevented from being pulled entirely through collar 2812, thereby limiting the proximal travel of rod assembly 2800. Locking component 2814 may have an indexed portion 2818 comprising two flats 2820 on opposing sides of indexed portion 2818. Indexed portion 2818 may have a geometry that substantially matches a geometry of an inner bore of handle 2810. For example, as shown, both indexed portion 2818 and the bore of collar 2812 may be substantially rectangular. Indexed portion 2818 may be sized to be received within the bore of collar 2812.

To lock rod assembly 2800, handle 2810 may be pulled proximally and rotated to rotate the position of flats 2820 such that the indexed portion 2818 can no longer be advanced through the bore of collar 2812. In some embodiments, indexed portion 2818 may be rotated in the range of about 30 degrees to about 150 degrees to maintain the locked position. Both handle 2810 and collar 2812 may have corresponding flats 2822 that indicate a position of flats 2820 on locking component 2814.

FIG. 29 illustrates first shaft assembly 2900 for some embodiments of the present disclosure. First shaft assembly 2900 may comprise a distal end 2902, a proximal end 2904, and may define a bore extending from distal end 2902 to proximal end 2904. Handle 2810 may be received within bore 2906. First shaft assembly 2900 may further comprise a shaft 2908 having a distal tip 2910 for coupling to main body 1602. Distal tip 2910 may be the same as distal tip 2506 discussed above.

A collar 2912 may be disposed at proximal end 2904. Collar 2912 may have external threads 2914 for threadedly engaging with second threaded sleeve 2718 as previously discussed. Handle 2710 may be rotated to rotate shaft 2908 and implant 1600 for self-drilling implant 1600 into the patient.

FIG. 30A illustrates a planar view of second shaft assembly 3000 for some embodiments of the present disclosure. Second shaft assembly 3000 may comprise a distal end 3002, a proximal end 3004, and may define a bore 3006 extending from distal end 3002 to proximal end 3004. In some embodiments, bore 3006 is sized to receive shaft 2908 therein.

Second shaft assembly 3000 may further comprise a shaft 3008 having a distal tip 3010. Distal tip 3010 may be substantially similar to the distal tip of second shaft assembly 2600 discussed above. In some embodiments, distal tip 3010 is formed as a castle nut for interfacing with receiving portions 2110. In some embodiments, shaft 3008 comprises a first portion 3012a having a smaller diameter than a second portion 3012b. Second portion 3012b may be sized to receive a spring 3014 therein, as shown in FIG. 30B.

FIG. 30B illustrates a close-up cross-sectional view of proximal end 3004 for some embodiments of the present disclosure. At proximal end 3004, second shaft assembly 3000 may comprise a first handle 3016 and a second handle 3018. First handle 3016 may control the rotation of shaft 3008, and second handle 3018 may control the rotation of handle 2710. In inner sleeve 3020 may be received within first handle 3016 and second handle 3018. Inner sleeve 3020 may have a pair of opposing J-slots 3022 configured to receive a pin 3024 therein that allows for the position of shaft 3008 to be locked. As discussed above, a spring 3014 may be received within 3012b to bias the movement of shaft 3008. Shaft 3008 may be pulled proximally to apply tension to compressive body 1604. Applying tension to compressive body 1604 may reduce the risk of pulling compressive body 1604 off implant 1600 and allows for the tension to be released to and applied to main body 1602 to drive main body 1602 into the patient for implantation thereof.

Third Insertion Instrument

Figure 31C:
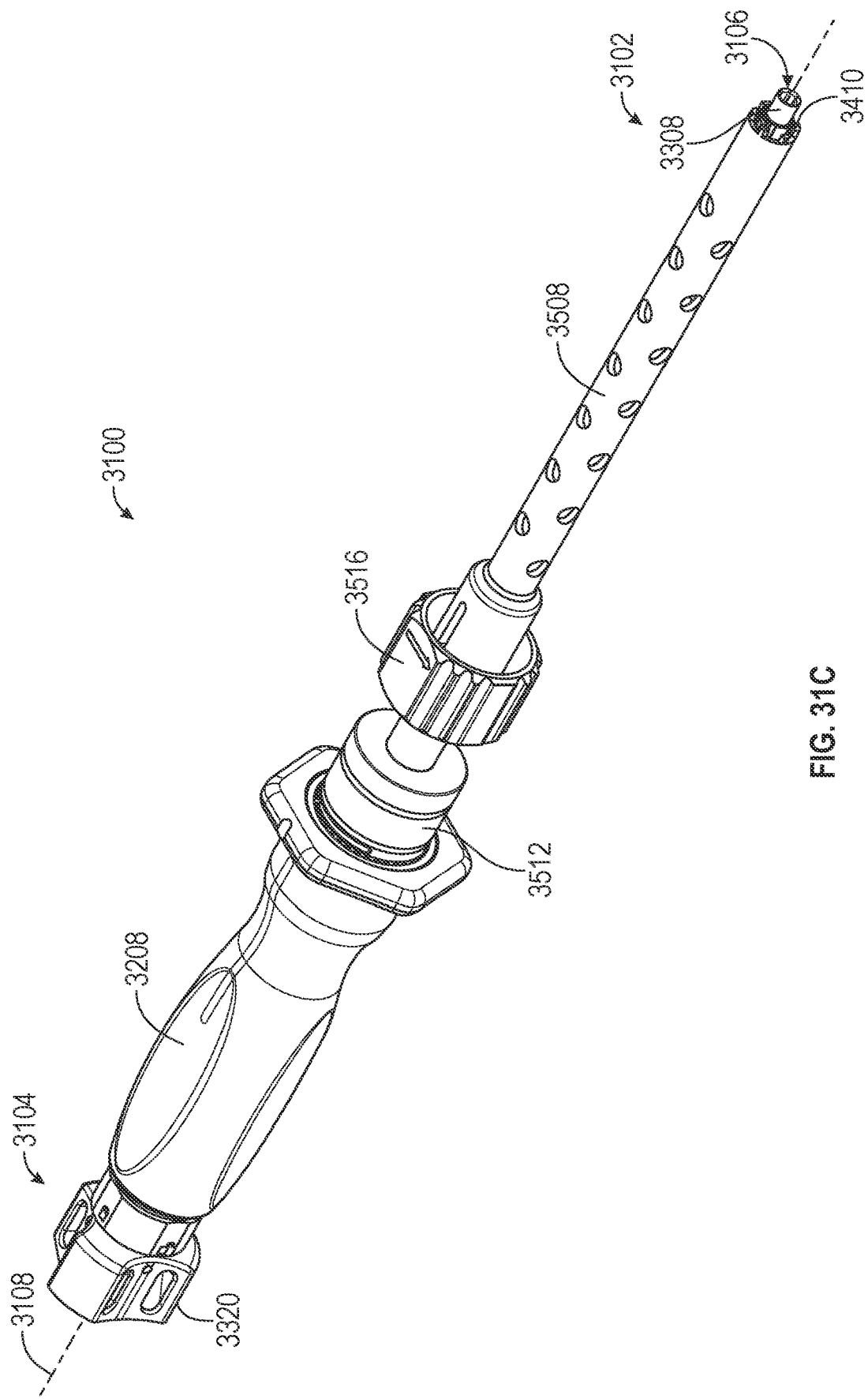
FIG. 31C illustrates a perspective view of the third insertion instrument for some embodiments.

FIGS. 31A, 31B, and 31C illustrate a planar view, a cross-sectional view, and a perspective view, respectively, of an insertion instrument 3100 for some embodiments of the present disclosure. As with insertion instruments 2300, 2700 discussed above, insertion instrument 3100 may be configured to: (1) insert the implant 1600 across the SI joint 800 and into the sacrum 804; (2) deploy the wings 1618a, 1618b; and (3) adjust the position of compressive body 1604 to apply the desired compression across SI joint 800. Insertion instrument 3100 may be used with any of implants 100, 900, 1600.

Insertion instrument 3100 may comprise a distal end 3102, a proximal end 3104, and a bore 3106 extending entirely along a longitudinal axis 3108 of insertion instrument 3100. When insertion instrument 3100 is coupled to implant 1600, longitudinal axis 3108 may be coaxial with longitudinal axis 1608 such that implant 1600 and insertion instrument 3100 may be inserted over a guidewire for inserting implant 1600 into the patient. Additionally, both bores 1606, 3106 may be unobstructed along axes 1608, 3108 to enable insertion over the guidewire. Furthermore, bores 1606, 3106 may enable bone graft (e.g., allograft, autograft, synthetic graft, etc.) to be added to implant 1600 through bores 1606, 3106.

Figure 31D:
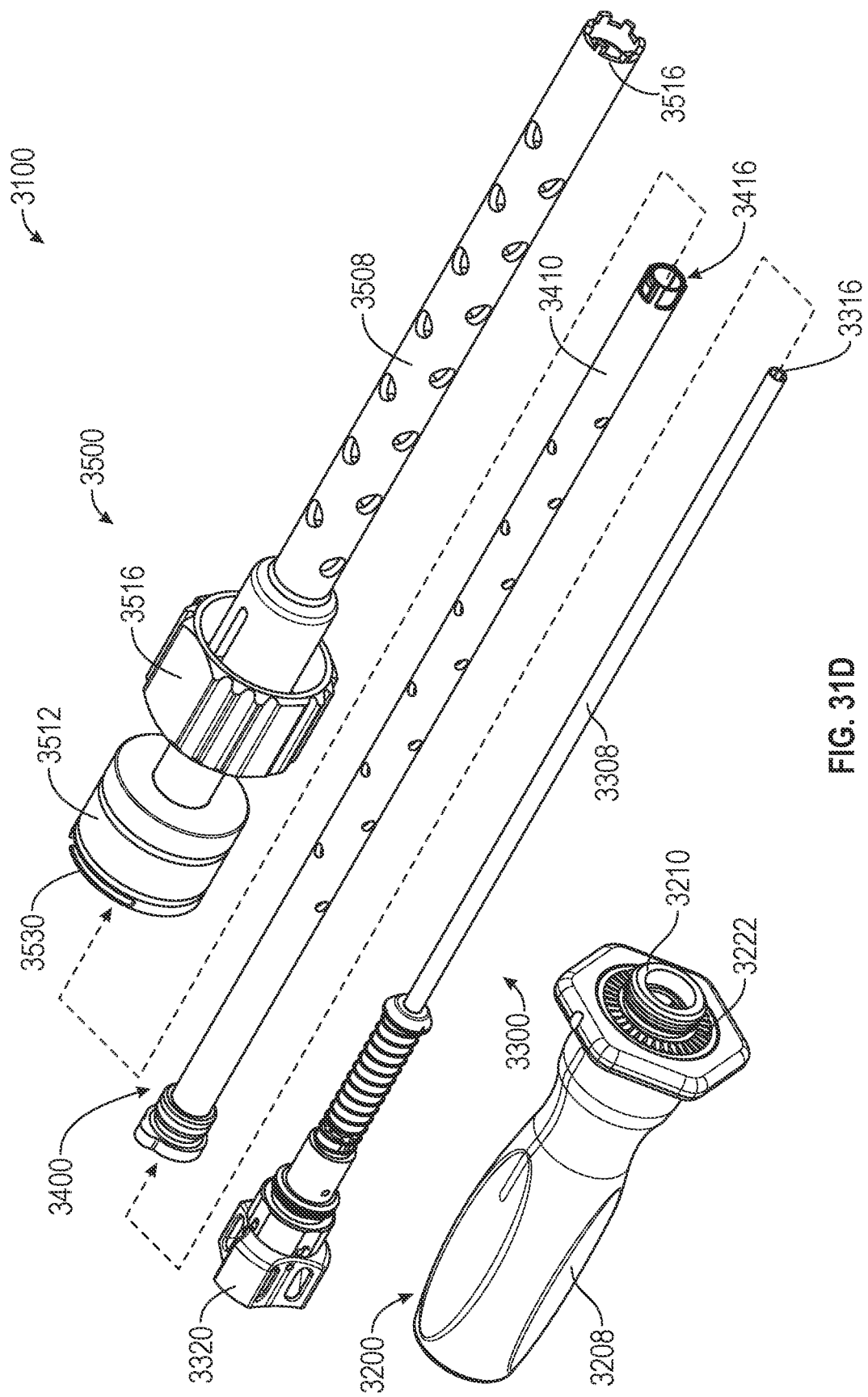
FIG. 31D illustrates an exploded view of the third insertion instrument for some embodiments.

As shown in FIG. 31D, insertion instrument 3100 comprises four subassemblies: (1) a handle subassembly 3200, (2) a wing driver subassembly 3300, (3) an implant driver subassembly 3400, and (4) a compressive body driver subassembly 3500. Wing driver subassembly 3300 may be at least partially received within implant driver subassembly 3400, and implant driver subassembly 3400 may be at least partially received within compressive body driver subassembly 3500. Wing driver subassembly 3300 may be configured to deploy wings 1618a, 1618b and may be coupled to proximal plunger 1626 on implant 1600. Implant driver subassembly 3400 may be configured to rotate implant 1600 for self-drilling implant 1600 through ilium 802, SI joint 800, and into sacrum 804. Implant driver subassembly 3400 may couple to proximal end 1612 of implant 1600. Compressive body driver subassembly 3500 may be configured to move compressive body 1604 longitudinally along main body 1602 and, accordingly, may be coupled to compressive body 1604.

Operation of insertion instrument 3100 to insert implant 1600 across SI joint 800 may proceed as follows. Once insertion instrument 3100 is coupled to implant 1600, implant driver subassembly 3400 may be rotated and advanced distally to rotate and self-drill implant 1600 through ilium 802, across SI joint 800, and into sacrum 804. Handle subassembly 3200 may be coupled to implant driver subassembly 3400 such that rotation of handle subassembly 3200 rotates implant driver subassembly 3400. Next, wing driver subassembly 3300 may be operated to rotate and advance distally proximal plunger 1626, thereby deploying wings 1618a, 1618b into cancellous bone 808 of sacrum 804. Lastly, compressive body driver subassembly 3500 may be operated and rotationally driven to thread compressive body 1604 to the desired location along proximal end 1612. As discussed above with respect to insertion instruments 2300, 2700, wing driver subassembly 3300, implant driver subassembly 3400, and compressive body driver subassembly 3500, may be simultaneously coupled to implant 1600 and successively actuated for insertion of implant 1600, or each subassembly 3300, 3400, 3500 may be coupled to the respective component on implant 1600 for actuation thereof and then decoupled before coupling the next subassembly for performing the respective function.

Figure 32A:
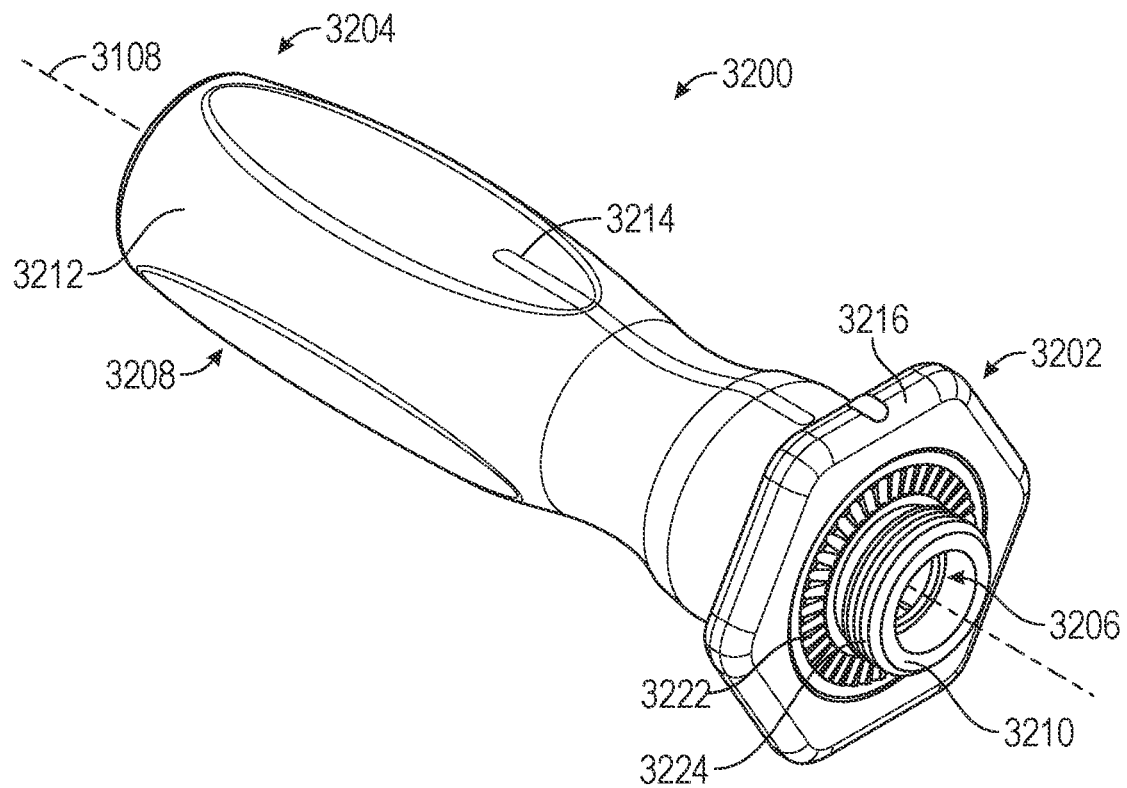
FIG. 32A illustrates a handle subassembly of the third insertion instrument for some embodiments.
Figure 32B:
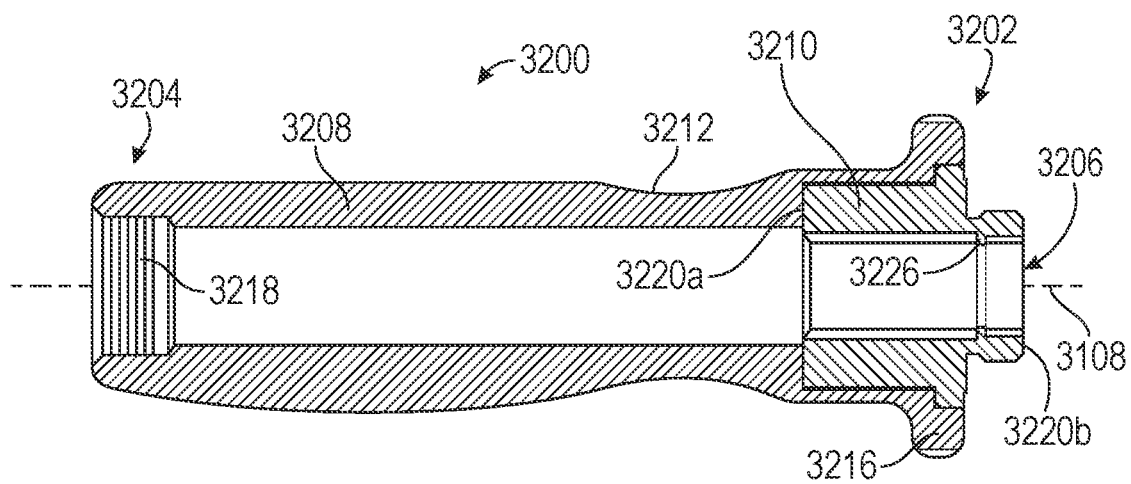
FIG. 32B illustrates a cross-sectional view of the handle subassembly for some embodiments.

Turning now to FIGS. 32A and 32B a perspective view and a cross-sectional view, respectively, of handle subassembly 3200 are illustrated for some embodiments. Handle subassembly 3200 may comprise a distal end 3202 and a proximal end 3204. A bore 3206 may extend through handle subassembly 3200 along longitudinal axis 3108.

Handle subassembly 3200 may further comprise a handle 3208 and a connecting member 3210. Handle 3208 may include a contoured outer surface 3212 for enhancing the grip of the user. Contoured outer surface 3212 may have a profile similar to a screwdriver or other rotational hand-operated tool, for example. Outer surface 3212 may also include a wing reference 3214 that provides a visual indicator to the surgeon of the position of a wing 1618a, 1618b. Handle 3208 may be symmetrical about longitudinal axis 3108, and a corresponding second wing reference (not shown) may be included on handle 3208, spaced 180 degrees apart from the first wing reference 3214 to indicate the position of the other wing 1618a, 1618b. Handle 3208 may be rotated to cause a corresponding rotation in implant 1600 such that wing references 3214 remain in-line with wings 1618a, 1618b. Thus, the surgeon is able to ascertain the position of wings 1618a, 1618b using wing reference 3214. In some embodiments, handle 3208 comprises a hex-shaped distal end 3216. Handle 3208 may also comprise internal threads 3218 that threadedly engage with threads 3334 on wing driver subassembly 3300 as shown in FIG. 31B.

Connecting member 3210 may couple handle subassembly 3200 to both implant driver subassembly 3400 and compressive body driver subassembly 3500. Connecting member 3210 may be coupled to handle 3208 at distal end 3202. As shown, connecting member 3210 has a proximal end 3220a received within handle 3208 and a distal end 3220b extending out of handle 3208. Connecting member 3210 may be coupled to handle 3208 via welding, a friction fit, a fastener, or via any other connection. Distal end 3220b may also comprise an array of ratchet teeth 3222 for locking handle subassembly 3200 with compressive body driver subassembly 3500 as discussed further below with respect to FIGS. 35A-35B. Distal end 3220b may include external threads 3224 for coupling to compressive body driver subassembly 3500 (see FIG. 31B). The connection between connecting member 3210 and compressive body driver subassembly 3500 may be configured such that compressive body driver subassembly 3500 can rotate freely from handle subassembly 3200, as discussed further below with respect to FIGS. 35A-35B. A collar 3408 and shaft 3410 of implant driver subassembly 3400 (see FIGS. 31B and 34A-34B) may also be received within connecting member 3210 to couple implant driver subassembly 3400 to handle subassembly 3200. The subassemblies 3200, 3400 may be coupled such that rotation of handle 3208 causes a corresponding rotation in implant driver subassembly 3400, which may cause rotation of implant 1600 for self-drilling implant 1600 into the patient.

Figure 33A:
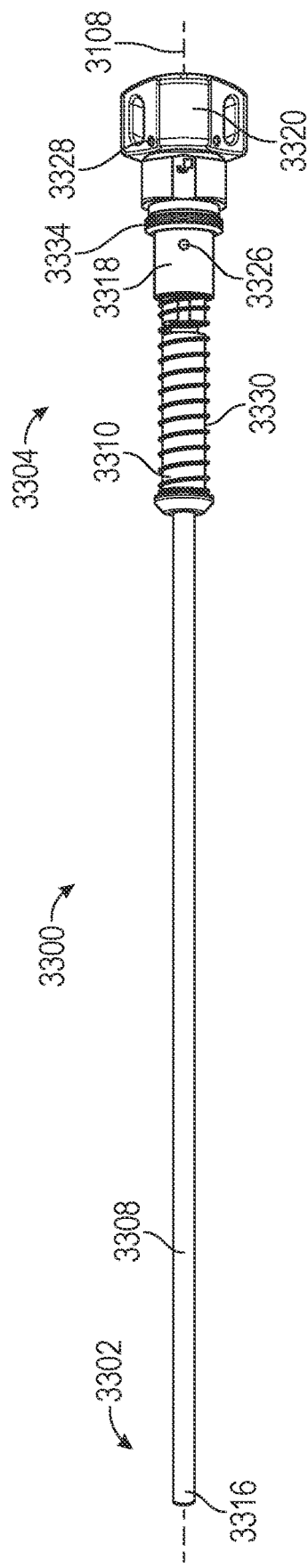
FIG. 33A illustrates a wing driver subassembly of the third insertion instrument for some embodiments.
Figure 33B:
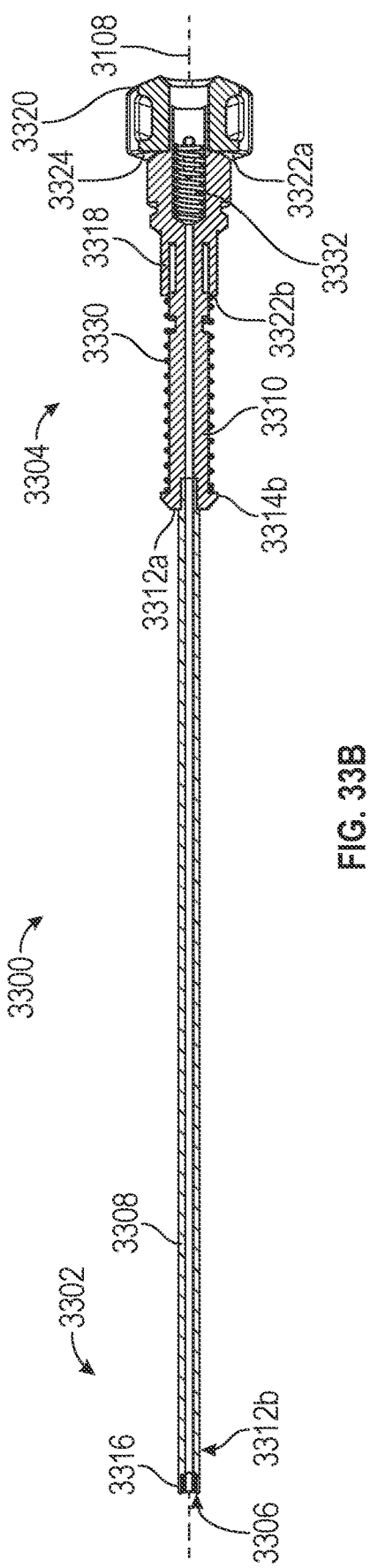
FIG. 33B illustrates a cross-sectional view of the wing driver subassembly for some embodiments.
Figure 33C:
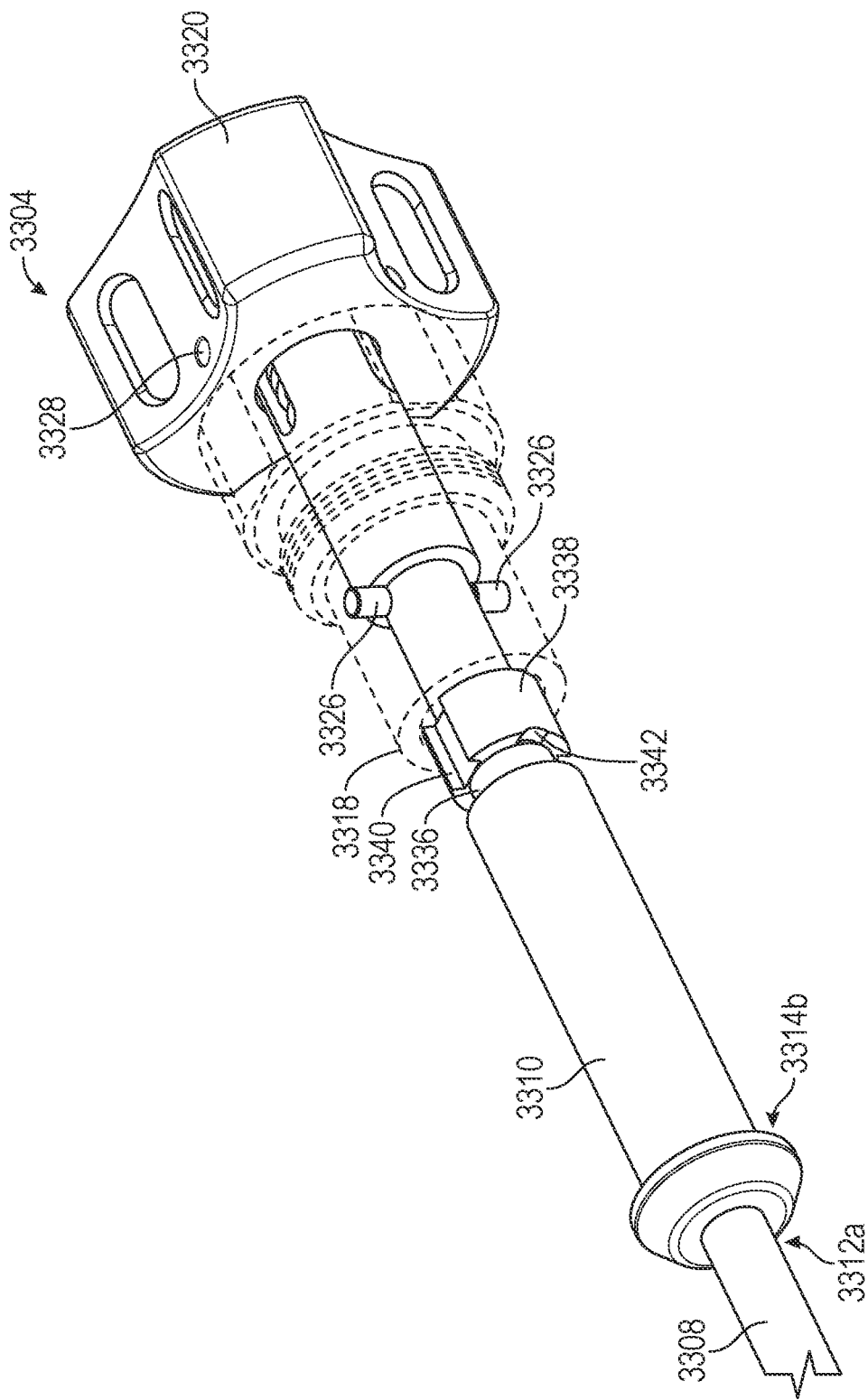
FIG. 33C illustrates a close-up perspective view of a proximal end of the wing driver subassembly for some embodiments.

Turning now to FIGS. 33A-33C, wing driver subassembly 3300 is illustrated for some embodiments. FIGS. 33A and 33B illustrate a planar view and a cross-sectional view, respectively, of wing driver subassembly 3300. As discussed previously, wing driver subassembly 3300 may be configured to deploy wings 1618a, 1618b by causing longitudinal, distal movement of proximal plunger 1626. Wing driver subassembly 3300 may also lock insertion instrument 3100 onto implant 1600.

Wing driver subassembly 3300 may include a distal end 3302, a proximal end 3304, and a bore 3306 along longitudinal axis 3108. Wing driver subassembly 3300 may further comprise a shaft 3308 coupled to an inner sleeve 3310. Shaft 3308 may be coupled at a proximal end 3312a to a distal end 3314b of inner sleeve 3310. In some embodiments, shaft 3308 is welded to inner sleeve 3310. In some embodiments, shaft 3308 is coupled to inner sleeve 3310 via fasteners, adhesives, or the like. Shaft 3308 may have a hex-shaped distal tip 3316 at a distal end 3312b for coupling to the hex-shaped non-threaded portion 1906 of proximal plunger 1626.

Inner sleeve 3310 may be received within and extend through a second sleeve 3318 and may be partially extended within a wing deployment knob 3320. When shaft 3308 is coupled to proximal plunger 1626, knob 3320 may be moved forward (i.e., distally) to deploy wings 1618a, 1618b via distal movement of proximal plunger 1626. When implant 1600 is in the final position with wings 1618a, 1618b engaged with the cortical bone 806 and compressive body 1604 engaged with the ilium 802, knob 3320 may be rotated to disengage knob 3320 from proximal plunger 1626. A proximal surface 3322a of outer sleeve 3314 may abut a distal surface 3324 of wing deployment knob 3320. Outer sleeve 3314 may be coupled to inner sleeve 3310 via pins 3326. Inner sleeve 3310 may be coupled to wing deployment knob 3320 via pins 3328. Knob 3320 may also include a plurality of openings that reduce overall weight of subassembly 3300, along with easing the cleanability of insertion instrument 3100.

A first spring 3330 may be received on an outer surface of inner sleeve 3310. First spring 3330 may be concentric with inner sleeve 3310. The first spring 3330 may bias (i.e., spring-load) shaft 3308 to maintain engagement of shaft 3308 with proximal plunger 1626, i.e., first spring 3330 biases shaft 3308 distally. First spring 3330 may be bounded by a distal surface 3322b of outer sleeve 3314 and a distal end 3314b of inner sleeve 3310. As discussed below, shaft 3308 may be locked in a retracted position by overcoming the spring force of first spring 3330.

A second spring 3332 may be received within outer sleeve 3314. The second spring 3332 may bias wing deployment knob 3320 proximally, i.e., away from implant 1600. The second spring 3332 may also transfer axial force applied distally to knob 3320 into outer sleeve 3314, into handle 3208, and then into main body 1602, which is connected to implant driver subassembly 3400 as discussed further below. Outer sleeve 3314 includes external threads 3334 for engaging with internal threads 3218. The threaded connection between wing driver subassembly 3300 and handle subassembly 3200 may enable the axial force from the knob 3320 to be transferred to handle subassembly 3200. Transferring this axial force reduces the force transferred to shaft 3308 and proximal plunger 1626 to reduce the risk of inserting implant 1600 too far medially, which risks damaging the neuroforamen as previously discussed. Furthermore, transferring the axial force as described reduces the risk of implant 1600 being forced off the end of insertion instrument 3100. The axial force is typically received from the surgeon pressing on wing deployment knob 3320 along longitudinal axis 3108 to move insertion instrument 3100 into the patient. Accordingly, second spring 3332 works to reduce the force transferred to implant 1600 while sufficient force to still cause distal movement of proximal plunger 1626 for deploying wings 1618a, 1618b can still be transferred to implant 1600.

Additionally, the pinned connection between knob 3320 and inner sleeve 3310 allows for rotation of knob 3320 to rotate inner sleeve 3310 and, thereby shaft 3308 for decoupling shaft 3308 from implant 1600 after the wings 1618a, 1618b are deployed. Further, knob 3320 may be rotated to rotate shaft 3308 and in turn proximal plunger 1626 to thread threaded portion 1904 along internal threads 2004, thereby advancing proximal plunger 1626 distally to deploy wings 1618a, 1618b. Thus, deploying wings 1618a, 1618b may comprise rotating wing deployment knob 3320 to rotate shaft 3308 and, in turn, threaded portion 1904 along internal threads 2004 to thread proximal plunger 1626 distally relative to main body 1602.

Referring now to FIG. 33C, a perspective view of proximal end 3304 of wing driver subassembly 3300 is illustrated for some embodiments. For clarity of illustration, first spring 3330 is not shown in FIG. 33C, and second sleeve 3318 is illustrated transparently (as indicated by the dashed lines). As shown, inner sleeve 3310 may include a circumferential groove 3336 that defines a raised portion 3338 proximal from circumferential groove 3336. Inner sleeve 3310, including raised portion 3338 may have a diameter or width smaller than an inner diameter or width of second sleeve 3318 such that inner sleeve 3310 can be moved longitudinally within second sleeve 3318. For example, the knob 3320 may be pulled proximally to move inner sleeve 3310 within second sleeve 3318. Distal end 3314b may be flanged and have a diameter or width larger than the inner dimension of second sleeve 3318, thereby limiting the proximal travel of inner sleeve 3310.

The raised portion 3338 may include two longitudinal grooves 3340 spaced 180 degrees apart from one another. Additionally, raised portion 3338 may include two circular grooves 3342 spaces radially from two longitudinal grooves 3340 on raised portion 3338. The grooves 3336, 3340, 3342 may enable shaft 3308 to be placed in a locked position. To lock the shaft 3308, wing deployment knob 3320 may be pulled proximally to move inner sleeve 3310 within second sleeve 3318. Longitudinal grooves 3340 may be aligned with pins 3326 such that two longitudinal grooves 3340 can slide by pins 3326 when inner sleeve 3310 is pulled proximal via a longitudinal force applied to knob 3320. Inner sleeve 3310 may be moved such that circumferential groove 3336 is in line with pins 3326, i.e., circumferential groove 3336 and pins 3326 are within substantially the same lateral plane. Once in this position, inner sleeve 3310 can be rotated to align pins 3326 with circular grooves 3342, and pins 3326 may sit in circular grooves 3342 to lock shaft 3308 in this retracted position. When pins 3326 are seated in circular grooves 3342, pins 3326 may prevent distal movement of inner sleeve 3310 and, therefore, shaft 3308 as well. Pulling inner sleeve 3310 proximally may require overcoming the spring force of first spring 3330. Wing driver subassembly 3300 may be placed in this locked position when the surgeon is coupling implant driver subassembly 3400 and/or compressive body driver subassembly 3500 to implant 1600. When wing driver subassembly 3300 is not locked, hex-shaped distal tip 3316 may protrude distally from implant driver subassembly 3400 and compressive body drive subassembly 3500 such that retracting and locking wing driver subassembly 3300 enables easier coupling of implant driver subassembly 3400 and compressive body drive subassembly 3500 to implant 1600. Additionally, retracting wing driver subassembly 3300 enables the distal tip 3416 of shaft 3410 to flex inward when coupling implant driver subassembly 3400 to the implant 1600. To unlock shaft 3308, inner sleeve 3310 may be pulled proximally to unseat pins 3326 from circular grooves 3342, and then inner sleeve 3310 may be rotated to realign pins 3326 with two circular grooves 3342 such that inner sleeve 3310 can be moved distally.

Figure 34A:
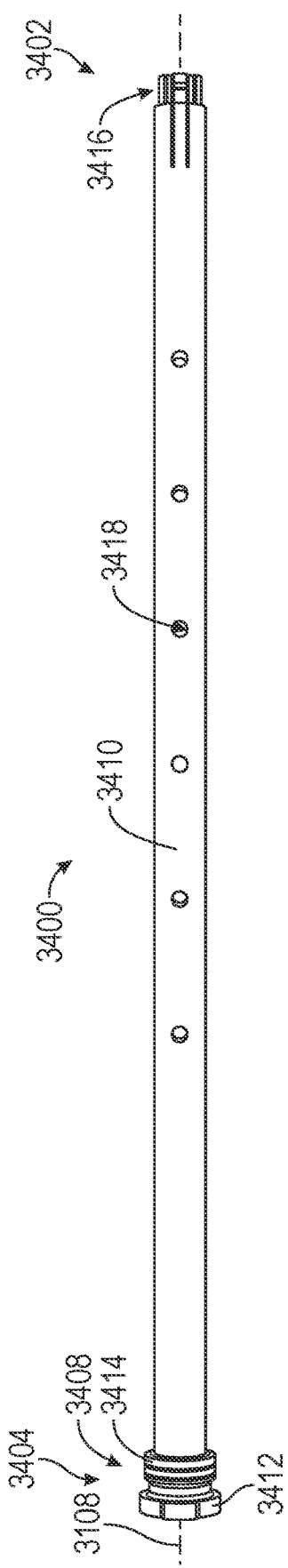
FIG. 34A illustrates an implant driver subassembly of the third insertion instrument for some embodiments.
Figure 34B:
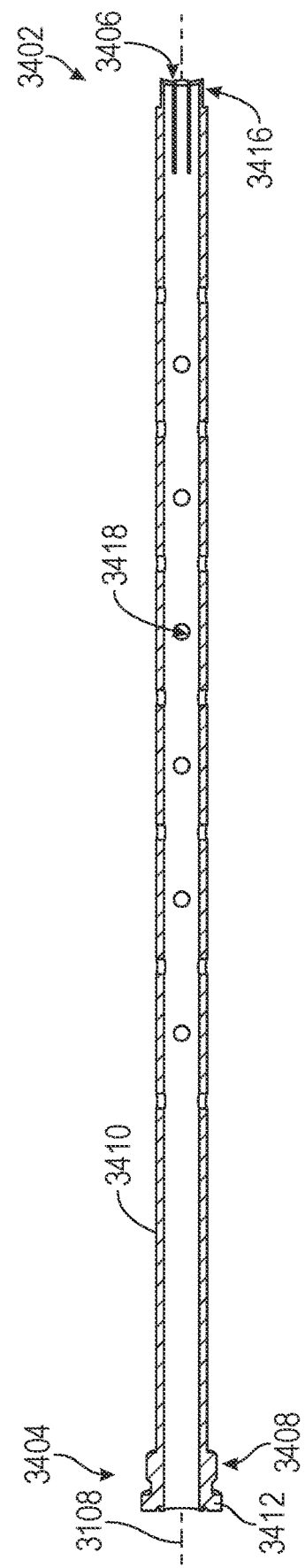
FIG. 34B illustrates a cross-sectional view of the implant driver subassembly for some embodiments.

FIGS. 34A-34B illustrate a planar view and a cross-sectional view, respectively, of the implant driver subassembly 3400 for some embodiments. Implant driver subassembly 3400 may comprise a distal end 3402, a proximal end 3404, and a bore 3406 extending along longitudinal axis 3108 from distal end 3402 to proximal end 3404. At proximal end 3404, implant driver subassembly 3400 may comprise a collar 3408. A shaft 3410 may be coupled to and extend from collar 3408. Collar 3408 may comprise a flanged portion 3412 that abuts a shoulder 3226 of connecting member 3210 such that implant driver subassembly 3400 is prevented from moving distally past shoulder 3226. Collar 3408 may also comprise external threads 3414 for threadedly engaging with an internal collar 3110 (see FIG. 31B) of insertion instrument 3100.

Distal end 3402 may include a distal tip 3416. Distal tip 3416 may be substantially similar to distal tip 2506 discussed previously and may couple to proximal end 1612 as described above with respect to distal tip 2506. When coupling insertion instrument 3100 to implant 1600, wing driver subassembly 3300 and compressive body drive subassembly 3500 may be retracted such that distal tip 3416 is the distal most component of insertion instrument 3100, which may enable the inward flexing of distal tip 3416 for coupling shaft 3410 to implant 1600. A plurality of openings 3418 may extend along shaft 3410 and may aid in cleaning insertion instrument 3100, along with overall weight reduction of insertion instrument 3100. As previously discussed, implant driver subassembly 3400 can be rotated by rotation of handle 3208. Distal tip 3416 may couple to main body 1602 such that rotating shaft 3410 rotates implant 1600 for inserting implant 1600 into the patient.

FIGS. 35A-35B illustrate a planar and cross-sectional view, respectively, of compressive body driver subassembly 3500 for some embodiments. Compressive body driver subassembly 3500 may comprise a distal end 3502, a proximal end 3504, and a bore 3506 extending from distal end 3502 to proximal end 3504 along longitudinal axis 3108. Compressive body driver subassembly 3500 may further include a shaft 3508 having a distal tip 3510, which may be configured as a castle nut for engaging with receiving portions 2110 on compressive body 1604.

At proximal end 3504, compressive body driver subassembly 3500 may include a threaded boss 3512, a connecting member 3514 connecting shaft 3508 to threaded boss 3512, and a knob 3516. Knob 3516 may be coupled to shaft 3508 such that rotating knob 3516 also rotates shaft 3508. Accordingly, the surgeon may rotate knob 3516 to rotate shaft 3508, which rotates compressive body 1604 along proximal end 1612 via threaded engagement of external threads 2006 and internal threads 2112, allowing the compression applied across SI joint 800 to be adjusted.

Pins 3518 may couple shaft 3508 to connecting member 3514 via a J-slot 3520 formed in connecting member 3514 as shown in FIG. 35B. Knob 3516 may be seated on shaft 3508. The position of shaft 3508 may be locked via J-slot 3520. A corresponding J-slot 3520 may be opposite the illustrated J-slot 3520. For example, the surgeon may have shaft 3508 locked via the J-slot 3520 while the surgeon connects wing driver subassembly 3300 and implant driver subassembly 3400 to proximal plunger 1626, and proximal end 1612, respectively, before unlocking shaft 3508 and coupling distal tip 3510 to compressive body 1604. The pins 3518 may be seated in J-slot 3520 such that shaft 3508 can be moved relative to connecting member 3514, and pins 3518 may ride within J-slot 3520. Accordingly, shaft 3508 may be pulled proximally, e.g., via pulling knob 3516 proximally, and then rotated to align pins 3518 into a groove 3522 of the J-slot, thereby preventing distal movement of shaft 3508 until pins 3518 are unseated from the grooves 3522.

A proximal end of the connecting member 3514 may be received within threaded boss 3512 and coupled thereto. A bottom surface 3524 of threaded boss 3512 may interpose a first washer 3526a and a second washer 3526b to couple connecting member 3514 to threaded boss 3512. A collar 3528 may be coupled to an outer surface of connecting member 3514 and concentric therewith. The collar 3528 may be distal from the second washer 3526b and may have an upper surface abutting a bottom surface of the second washer 3526b. Washers 3526a, 3526b may be plastic washers configured to prevent galling of metal on metal parts (i.e., between threaded boss 3512 and connecting member 3514).

The threaded boss 3512 may include a pair of flexible tabs 3530 with teeth 3532 protruding proximally from flexible tabs 3530 in the direction of longitudinal axis 3108. The tabs 3530 and teeth 3532 may provide an auto-locking feature for insertion instrument 3100. As handle subassembly 3200 is rotated, ratchet teeth 3222 engage with teeth 3532 to lock handle subassembly 3200 with threaded boss 3512 and, thereby compressive body drive subassembly 3500. Rotation of threaded boss 3512 in a first direction (e.g., clockwise) may lock handle subassembly 3200 to compressive body driver subassembly 3500, while rotation of a threaded boss 3512 in a second, opposite direction (e.g., counterclockwise) may unlock handle subassembly 3200 from compressive body driver subassembly 3500 to allow for disassembly of insertion instrument 3100. Meanwhile, shaft 3508 may be configured to rotate independently from rotation of threaded boss 3512.

Compressive body driver subassembly 3500 may additionally include a spring 3534. Spring 3534 may be received within a proximal end of shaft 3508 and may be bounded by a distal face 3536 of connecting member 3514 and a shoulder 3538 of shaft 3508. Similar to second spring 3332 discussed above, spring 3534 may bias shaft 3508 distally such that the connection between distal tip 3510 and compressive body 1604 can be maintained. Because the compressive body 1604 will be traveling distally along main body 1602 as compressive body 1604 is threaded by subassembly 3500, providing this spring-loading allows distal tip 3510 to maintain the connection between shaft 3508 and compressive body 1604.

In some embodiments, insertion instrument 2300, 2700, 3100 comprises titanium or a titanium alloy. In some embodiments, insertion instrument 2300, 2700, 3100 comprises stainless steel. In some embodiments, insertion instrument 2300, 2700, 3100 comprises a polymer, a plastic, a bioabsorbable material, or any combination thereof. For example, insertion instrument 2300, 2700, 3100 may be formed from polyacrylamide or IXEF®. In some embodiments, insertion instrument 2300, 2700, 3100 is additively manufactured and may be formed from RULON, PEEK, or the like. In some embodiments, at least a portion of insertion instrument 2300, 2700, 3100 is radiopaque or radiolucent. In some embodiments, insertion instrument 2300, 2700, 3100 is disposable.

In some embodiments, one or more components of insertion instrument 2300, 2700, 3100 are coated in a biocompatible, corrosion resistant material to help protect and/or strengthen the component. For example, some or all portions of insertion instrument 2300, 2700, 3100 may be advantageously reinforced with a coating material to increase the durability of the components while maintaining safety to the patient by the coating material being of a biocompatible substance. Such a coating material may be applied specifically to components of insertion instrument 2300, 2700, 3100 that come into contact with tissue of the patient. In some embodiments, the coating material may be an anodized metal. In some embodiments, the coating material may be formed by an electroplating process, such as a hard chromium electroplating process. For example, in some embodiments, the coating material may be MEDCOAT 2000™. In some embodiments, the thickness of the coating material may be between about 1 μm to about 15 μm. In some embodiments, the coating material may be between about 2 μm to about 10 μm.

Method and Surgical Kit

Figure 36:
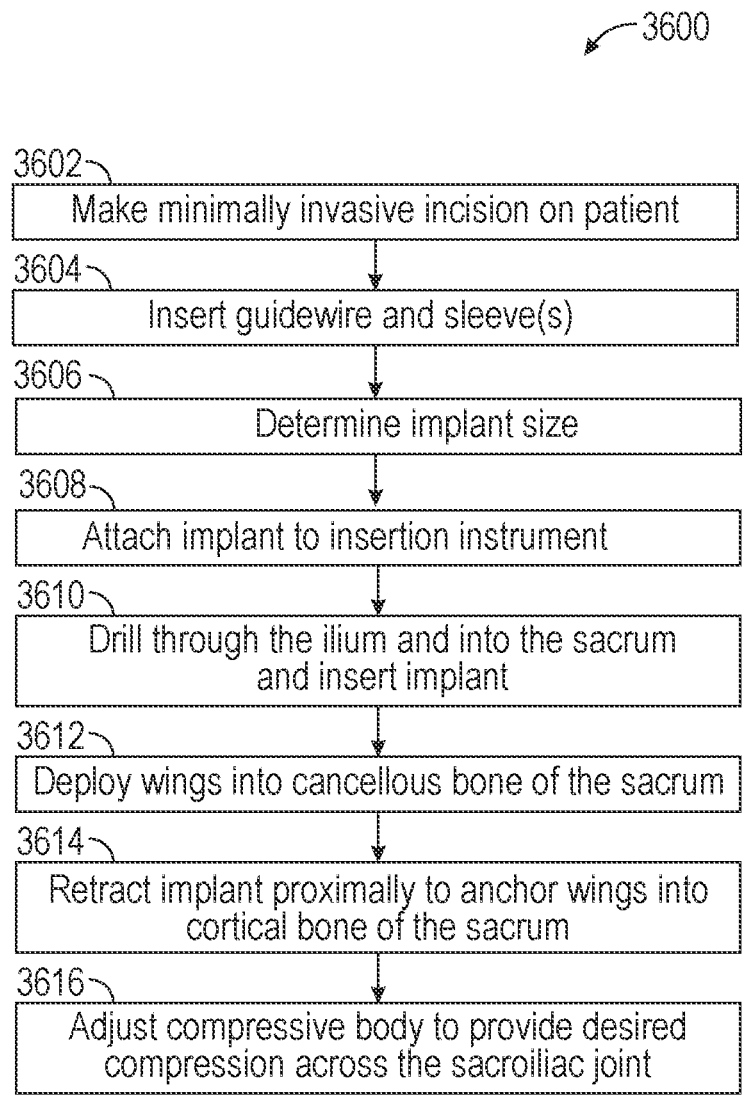
FIG. 36 illustrates an exemplary method in accordance with embodiments of the present disclosure.

Turning now to FIG. 36, a method 3600 for insertion and implantation of implants 100, 900, 1600 using insertion instrument 2300, 2700, 3100 is illustrated for some embodiments of the present disclosure. One or more implants 100, 900, 1600 may be inserted across the SI joint 800 to provide fusion and stabilization thereof. In some embodiments, the implants 100, 900, 1600 are inserted at the S1 level of the spine. Placement of the implants 100, 900, 1600 may be done to avoid damaging the neuroforamen that are medial from the sacrum 804.

At step 3602, a minimally invasive incision may be made on the patient. As discussed above, minimally invasive incisions reduce blood loss, recovery time, and hospital stay, among other benefits, as compared to open surgery. However, it is contemplated that embodiments herein may be practiced in an open surgery. In some embodiments, the incision is made to provide lateral access to the patient such that the implant 100, 900, 1600 may be inserted across the SI joint 800. In some embodiments, a separate incision is made for each implant 100, 900, 1600 that is inserted. In some embodiments, each implant 100, 900, 1600 is inserted through the same incision. In some embodiments, one, two, or three implants are inserted for the SI joint fusion procedure.

Next, at step 3604, a guidewire 2202 and sleeves 2204 may be inserted through the incision to provide access to the target space. The guidewire 2202 may be inserted (e.g., tapped or using any other method) through the incision and advanced into the sacrum 804 where the surgeon wishes to insert the implant 100, 900, 1600. When multiple implants are inserted, a parallel pin guidewire tool may be used to insert the guidewires 2202 parallelly through the incision. Soft tissues may then be dilated using one or more dilators or sleeves 2204. In some embodiments, the soft tissues are dilated by sequentially inserting larger width or diameter dilators or sleeves 2204 over the guidewire 2202. Each successive sleeve 2204 may be inserted over the previous sleeve 2204. After the last sleeve 2204 has been added, the smaller diameter sleeves 2204 may be removed, leaving the guidewire 2202 in place. In some embodiments, the largest sleeve 2204 is left over the guidewire 2202, and implant 100, 900, 1600 and insertion instrument 2300, 2700, 3100 are inserted through the largest sleeve 2204.

Next, at step 3606, the size of the implant 100, 900, 1600 for the patient may be determined. In some embodiments, the size of the implant 100, 900, 1600 is determined based on the depth that guidewire 2202 is inserted into the patient. In some embodiments, the size of the implant 100, 900, 1600 is determined based on a distance between the outer surface of ilium 802 (or a distalmost surface of sleeve 2204, which may be docked against the outer surface of ilium 802) and a point on guidewire 2202 within sacrum 804. As discussed previously, guidewire 2202 may comprise an alignment indicator 3704 (see FIG. 37) that may be visible under fluoroscopy such that the surgeon can determine the location of the guidewire 2202 within the patient. Generally, any method of determining the requisite size for the implant 100, 900, 1600 based on the anatomy of the patient is within the scope hereof. Different sized implants 100, 900, 1600 may have different lengths but the same or substantially similar diameters.

Next, at step 3608, the implant 100, 900, 1600 may be coupled to the insertion instrument 2300, 2700, 3100. As previously discussed, the insertion instrument 2300, 2700, 3100 may have a rod 2310, 2806 or shaft 3308 that couples to non-threaded portion 1906 on proximal plunger 1626, a shaft 2318, 2908, 3410 that couples to proximal end 1612 of main body 1602, and a compressive body shaft 2322, 3008, 3508 that couples to compressive body 1604. Each of rod 2310, 2806, or shaft 3308, shaft 2318, 2908, 3410 and compressive body shaft 2322, 3008, 3508 may be individually coupled to and decoupled from their respective component on implant 1600 once their respective action is performed, or simultaneously coupled for operating insertion instrument 2300, 2700, 3100.

Thereafter, at step 3610, the surgeon may drill into the patient, through the ilium 802 and into the sacrum 804 to provide an access space for inserting the implant 100, 900. In some embodiments, the drilling is self-drilling of implant 100, 900, 1600, with the surgeon rotationally driving the implant using insertion instrument 2300, 2700, 3100 to drill into the patient. In some embodiments, a drill is used. The drill may be configured to be inserted over the guidewire 2202 to ensure that the hole is made at the desired implantation location. Drilling also provides distraction of the target space. As discussed above, implant 100, 900, 1600 may have an externally threaded distal end 106, 908, 1610 that can distract the target space to aid in implantation. Furthermore, self-harvesting features, such as an open distal tip, slots, flutes, or any combination thereof may be provided such that implant 100, 900, 1600 self-harvests bone during insertion. Additionally, implant 100, 900, 1600 may be formed with a substantially blunt distal tip 112, 914 to reduce the likelihood that the implant pierces through the innermost cortical wall of the sacrum 804, thereby protecting the neuroforamen. Implant 100, 900, 1600 may also be packed with bone graft material to promote bony fusion. Step 3610 may also comprise inserting the implant 100, 900, 1600 into the sacrum 804, which may be done as part of the self-drilling process, or after drilling into the sacrum 804 and by advancing the implant 100, 900, 1600 over guidewire 2202.

Once implant 100, 900, 1600 is at the implantation site, at step 3612, the wings may be deployed into the cancellous bone 808 of the sacrum 804. The cancellous bone 808 is softer than the cortical bone 806; thus, it is advantageous to deploy the wings in the cancellous bone 808 because less force will be required. As discussed above, plunger 122, 924, 1624 may be formed with a cannulation for post packing or injection of bone graft through the cannulation after deployment of the wings. In some embodiments, the wings are deployed by driving rod 2310, 2806 with rod handle 2312, 2810. Shaft 3308 may be driven via knob 3320. In turn, proximal plunger 1626 is threaded along internal threads 2004, thereby moving proximal plunger 1626 longitudinally, and the longitudinal movement may move the wings between the open configuration to the closed configuration.

Next, at step 3614, implant 100, 900, 1600 may be retracted proximally to anchor the wings against the cortical bone 808 of the sacrum 804. The proximal retraction may be carried out by the operator pulling insertion instrument 2300, 2700, 3100 proximally. In some embodiments, the proximal retraction is performed by rod handle 2312, 2810 being pulled proximally. In some embodiments, the proximal retraction is performed by pulling knob 3320 proximally. Thus, a distal anchor is formed by the wings engaged with cortical bone 808. The distal anchor may be selectively positioned in the open configuration and the closed configuration. The wings may comprise a substantially flat bottom surface to dock against cortical bone 808. In some embodiments, the wings comprise fangs 1814 protruding from the bottom surface to anchor into the cortical bone 808 and to counter rotation of the implant 100, 900, 1600. Additionally, implant 100, 900, 1600 may comprise a substantially smooth body located proximally from the threaded distal end 106, 908, 1610 that aids in retracting implant 100, 900, 1600.

At step 3616, the compressive body 104, 904, 1604 may be adjusted to adjust the compression applied across the SI joint 800. As the compressive body is advanced distally, the compression across the SI joint 800 is increased. Increasing compression improves the fusion and stabilization of the SI joint 800 as micromotions therein are reduced. In some embodiments, the compressive body is advanced distally until compressive elements 128, 928 or recesses 2108 are docked against an outer surface of the ilium 802. In some embodiments, the compressive body is advanced distally such that compressive elements 128, 928 or recesses 2108 are partially embedded within the ilium 802. Thus, a proximal anchor is formed. In some embodiments, compressive body 1604 is advanced by rotating compressive body shaft 2322 using handle 2324, 2710.

In some embodiments, the above-described method 3600 may be provided as instructions with a surgical kit and/or with the implant 100, 900, 1600. For example, the surgical kit may comprise the instructions, one or more implants 100, 900, 1600 insertion instrument 2300, guidewire 2202, sleeves 2204, and any other instrumentation necessary to complete the SI joint fusion procedure. An exemplary surgical kit 3700 is discussed below with respect to FIG. 37.

It will be appreciated that features of implants 100, 900, 1600 may be interchangeable without departing from the scope hereof. For example, flutes 916 may replace or be added in addition to openings 124 on first body 102 of implant 100. Similarly, it is contemplated that the more flexible compressive element 928 on implant 900 may instead be used on implant 100. Generally, any feature on implant 100, 900, 1600 may be used with a different implant 100, 900, 1600.

In some embodiments, all or part of implant 100, 900, 1600 may be composed of titanium or a titanium alloy. In some embodiments, all or part of implant 100, 900, 1600 may be composed of stainless steel. In some embodiments, all or part of implant 100, 900, 1600 may be composed of magnesium. In some embodiments, all or part of implant 100, 900, 1600 may be composed of a polymer or a bioabsorbable material. In some embodiments, all or part of implant 100, 900, 1600 may be composed of allograft (i.e., cadaver bone), such as cortical allograft. In some embodiments, implant 100, 900, 1600 may be formed by an additive manufacturing process. In some embodiments, implant 100, 900, 1600 may be formed by machining and/or molding. In some embodiments, implant 100, 900, 1600 coated on at least one surface thereof. In some embodiments, at least one outer surface of the implant 100, 900, 1600 may be coated with hydroxyapatite (HA). In some embodiments, multiple surfaces may be coated with HA. In some embodiments, implant 100, 900, 1600 is packed with bone graft, such as demineralized bone matrix.

Figure 37:
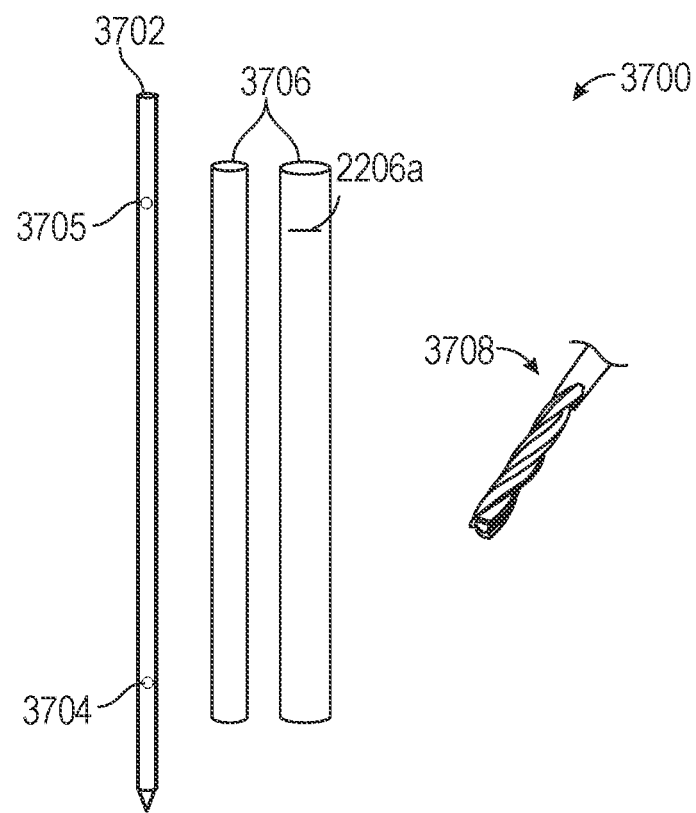
FIG. 37 illustrates an exemplary surgical kit in accordance with embodiments of the present disclosure.

Turning now to FIG. 37, an exemplary surgical kit 3700 is illustrated for preparing a target space (e.g., SI joint 800) for insertion of an implant 100, 900, 1600 for some embodiments of the present disclosure. The surgical kit 3700 may include the illustrated surgical tools, along with one or more implants 100, 900, 1600, and one or more insertion instruments 2300, 2700, 3100 for bony fixation of a target space, such as SI joint 800.

In some embodiments, exemplary surgical kit 3700 comprises a guidewire 3702. Guidewire 3702 may be inserted into a minimally invasive incision and, under fluoroscopy, guidewire 3702 may be advanced to locate the target space where it is desired to place implant 100, 900, 1600. Guidewire 3702 may correspond to guidewire 2202 previously discussed. In some embodiments, guidewire 3702 comprises an alignment indicator 3704 on a distal end of guidewire 3702 used to ensure guidewire 3702 is correctly aligned in the patient. The alignment indicator 3704 may be a feature on the distal end of the guidewire 3702 that is visible under fluoroscopy such that the surgeon can see the location of the alignment indicator 3704 relative to patient's anatomy to ensure the guidewire 3702 is at the correct depth into the sacrum 804 as viewed in the medial direction. For example, the alignment indicator 3704 may be a hole (as shown), a groove, a notch, a contrasting mark, or the like.

In some embodiments, the reference point for inserting guidewire 3702 is the cortical bone 808 of sacrum 804 that is medial to the articular surface of the SI joint 800. That is, the alignment indicator 3704 may be placed in cancellous bone 808 of sacrum 804 to ensure that wings 1618a, 1618b can deploy. As discussed previously, because the cancellous bone 808 is softer than cortical bone 806, the wings 1618a, 1618b are able to deploy into cancellous bone 808. When the guidewire 3702 is in this position, the guidewire 3702 provides a representation of the final placement of implant 1600. A sizing instrument can then be placed against the lateral surface of ilium 802, over guidewire 3702. A marking feature 3705 (such as a laser mark) may be on a proximal end of the guidewire 3702 relative to indicators on the sizing instrument (not shown) can provide an indication of the size of the implant 1600 that should be inserted into the patient. For example, the sizing instrument may be integrated into a dilator (e.g., sleeve 2204 shown in FIG. 22) such that the dilator includes indicators that dictate the size of implant 1600 to implant. For example, if, when guidewire 3702 is inserted into cancellous bone 808, marking feature 3705 is proximate to a first indicator 2206a (FIG. 22), the surgeon may know to use an implant size based on the first indicator. If the marking feature 3705 is instead proximate to a second indicator 2206b (FIG. 22) that is longitudinally spaced form the first indicator 2206a, the surgeon may know to use a different size implant 1600.

In some embodiments, exemplary surgical kit 3700 comprises one or more dilators 3706. Dilators 3706 may correspond to sleeves 2204 discussed previously. Dilators 3706 may be hollow tubes that are placed over guidewire 3702 to create a working channel for insertion of implant 100, 900, 1600. Dilators 3706 may be provided in increasing sizes such that a larger sized dilator 3706 may be placed over a smaller-sized dilator to dilate the target space.

In some embodiments, exemplary surgical kit 3700 comprises a drill bit 3708. Drill bit 3708 may be used for drilling a pilot hole to access the target space. In some embodiments, drill bit 3708 is cannulated, as shown, such that drill bit 3708 may be inserted over guidewire 3702. In some embodiments, exemplary surgical kit 3700 further comprises a decorticator (not shown) for roughening the target space. The decorticator may likewise be cannulated for insertion over guidewire 3702. It will be appreciated that various other tools may be provided with a surgical kit for bony fusion without departing from the scope hereof.

In some embodiments, implant 100, 900, 1600 may be used in various other regions of the body other than (or in addition to) the SI joint 800. For example, it is contemplated that implants 100, 900, 1600 could be used for fracture repair, such as for a broken hip. For example, to treat an intertrochanteric fracture, implants 100, 900, 1600 could be inserted to compress the fracture, with the wings being placed in either the greater trochanter region or the less trochanter region of the femur. Other hip fractures, such as subtrochanteric fractures and femoral head fractures may similarly be treated using implants 100, 900, 1600 to compress the fracture. Generally, implants 100, 900, 1600 may be used in any region of the body to apply compression across a target space, such as a joint space or a fracture region. It will be appreciated that based on where in the body an implant 100, 900, 1600 is implanted, the size of the implant may be adjusted accordingly. For example, an implant 100, 900, 1600 used to treat a fracture in the femur may be larger than those used in the SI joint.

Features described above as well as those claimed below may be combined in various ways without departing from the scope hereof. The following examples illustrate some possible, non-limiting combinations:

(A1) An implant for insertion across a sacroiliac (SI) joint, comprising: a first body defining a longitudinal axis extending along a length of the first body and a lateral axis extending along a width of the first body, the first body comprising: a window extending laterally along the lateral axis of the first body; a distal end along the length of the first body; a threaded proximal end along the length of the first body; and a distal anchor selectively positioned in an open configuration and a closed configuration, the distal anchor comprising a first wing and a second wing, wherein the first wing and the second wing are housed within the window in the closed configuration, and wherein the first wing and the second wing are deployed at least partially external from the window in the open configuration; a second body coupled to the threaded proximal end, the second body comprising a proximal anchor disposed on an outer surface of the second body, wherein the second body is configured to be threaded along the threaded proximal end to adjust an overall length of the implant, thereby adjusting an amount of compression across the SI joint.

(A2) For the implant denoted as (A1), further comprising: a plunger received within the first body, the plunger coupled to the first wing and the second wing, wherein longitudinal distal movement of the plunger deploys the first wing and the second wing at least partially external from the window.

(A3) For the implant denoted as (A1) or (A2), further comprising: a first linkage comprising a first outer end and a first inner end; a second linkage comprising a second outer end and a second inner end, wherein the first linkage is coupled to the first wing at the first outer end and the second linkage is coupled to the second wing at the second outer end; and a pin coupling the first wing to the second wing via the first inner end and the second inner end to form a first pivot point such that the longitudinal distal movement of the plunger causes the first linkage and the second linkage to pivot about the first pivot point to transition the distal anchor from the closed configuration to the open configuration.

(A4) For the implant denoted as any of (A1) through (A3), wherein the distal end of the first body comprises an externally threaded portion and a non-threaded portion, the non-threaded portion disposed proximally from the externally threaded portion, and wherein the non-threaded portion comprises one or more openings therethrough.

(A5) For the implant denoted as any of (A1) through (A4), wherein a proximal end of the second body comprises a bore extending along the longitudinal axis, and wherein an inner surface of the proximal end comprises a shape configured to couple with an instrument configured to rotate the second body along the threaded proximal end of the first body.

(A6) For the implant denoted as any of (A1) through (A5), The implant of clause 1, wherein the distal end of the first body comprises a blunt distal tip, the blunt distal tip defining an opening.

(A7) For the implant denoted as any of (A1) through (A6), wherein the distal end comprises one or more fenestrations proximal to the opening to self-harvest bone.

(A8) For the implant denoted as any of (A1) through (A7), wherein at least one of the first wing or the second wing comprises a generally flat surface configured to anchor against a cortical bone of a sacrum, wherein when the implant is in the open configuration, the implant is configured to be retracted proximally to anchor the first wing and the second wing against the cortical bone.

(B1) An implant for insertion across a sacroiliac (SI) joint, comprising: a first body defining a longitudinal axis extending along a length of the first body and a lateral axis extending along a width of the first body, the first body comprising: a window extending laterally along the lateral axis of the first body; a distal anchor having an open configuration and a closed configuration, the distal anchor comprising a first wing and a second wing, wherein the first wing and the second wing are housed within the window in the closed configuration, and wherein the first wing and the second wing are deployed at least partially external from the window in the open configuration; a second body comprising a proximal anchor disposed on an outer surface of the second body, wherein the proximal anchor comprises a compressive element; and a threaded body comprising a distal end and a proximal end, the threaded body coupled to the first body at the distal end and to the second body at the proximal end, wherein the second body is configured to be threaded along the threaded body to adjust an overall length of the implant, thereby adjusting an amount of compression across the SI joint.

(B2) For the implant denoted as (B1), further comprising: a plunger received within the first body, wherein the plunger is coupled to the first wing and to the second wing, and wherein longitudinal distal movement of the plunger transitions the first wing and the second wing from the closed configuration to the open configuration.

(B3) For the implant denoted as (B1) or (B2), wherein the threaded body is configured to be advanced distally within the first body to abut against a proximal end of the plunger to hold the first wing and the second wing in the open configuration.

(B4) For the implant denoted as any of (B1) through (B3), wherein the first wing comprises a first slot therethrough and the second wing comprise a corresponding second slot therethrough, and wherein the implant further comprises: a fixed pin extending through the first body and received in the first slot and the second slot, wherein when the plunger is advanced distally, the first slot and the second slot move along the fixed pin such that a first curvature of the first slot defines a first travel path of the first wing, and a second curvature of the second slot defines a second travel path of the second wing.

(B5) For the implant denoted as any of (B1) through (B4), wherein the first curvature of the first slot is configured to deploy the first wing along a first path that is tangent to a first curve formed by the first wing in the closed configuration, and wherein the second curvature of the second slot is configured to deploy the second wing along a second path that is tangent to a second curve formed by the second wing in the closed configuration.

(B6) For the implant denoted as any of (B1) through (B5), wherein the first body further comprises: an externally threaded distal end, a proximal end of the first body, and a central section therebetween, and wherein at least one flute extends along the externally threaded distal end and the central section.

(B7) For the implant denoted as any of (B1) through (B6), wherein the second body defines a longitudinal bore, the longitudinal bore having an exterior surface configured to be engaged by an instrument to rotate and thread the second body along the threaded body.

(B8) For the implant denoted as any of (B1) through (B7), wherein the compressive element is a polyaxial washer.

(C1) A method for fusion and stabilization of a sacroiliac (SI) joint, comprising: providing instructions for inserting an implant across the SI joint, the instructions comprising: make a minimally invasive incision on a patient to provide access to the SI joint of the patient; dilate soft tissue of the patient by sequentially advancing dilators over a guide wire, each sequential dilator having a larger width than a previous dilator; insert the implant through the minimally invasive incision, through an ilium, through the SI joint, and into a sacrum of the patient, wherein the implant comprises: a first body having a distal anchor comprising a pair of deployable wings; and a second body having a proximal anchor comprising a compressive element; deploy the pair of deployable wings; and advance the second body distally to anchor the compressive element and cause compression across the SI joint.

(C2) For the method denoted as (C1), wherein the instructions further comprise: prior to advancing the second body distally, retracting the implant proximally to anchor the pair of deployable wings against cortical bone of the sacrum.

(C3) For the method denoted as (C1) or (C2), wherein the implant defines a central bore extending therethrough and further comprises: a plunger received within the central bore and coupled to the pair of deployable wings, the plunger comprising internal threads, and wherein deploying the pair of deployable wings comprises: engaging the internal threads with an instrument; and rotating the instrument to advance the plunger distally, thereby deploying the pair of deployable wings.

(C4) For the method denoted as any of (C1) through (C3), wherein the implant further comprises one or more slots, and wherein the instructions further comprise: prior to inserting the implant, adding bone graft into the one or more slots.

(D1) An implant for insertion across a sacroiliac (SI) joint, comprising: a main body defining a longitudinal axis extending along a length of the main body and a lateral axis extending along a width of the main body, the main body comprising: a window extending laterally along the lateral axis of the main body; a distal end along the length of the main body and comprising a distal anchor having an open configuration and a closed configuration, the distal anchor comprising a first wing and a second wing, wherein the first wing and the second wing are housed within the window in the closed configuration, and wherein the first wing and the second wing are deployed at least partially external from the window in the open configuration; and a threaded proximal end along the length of the main body; a compressive body coupled to the threaded proximal end, the compressive body forming a proximal anchor for the implant, wherein the compressive body is configured to be threaded along the threaded proximal end to adjust an overall length of the implant, thereby adjusting an amount of compression across the SI joint; and a cannula extending along the longitudinal axis.

(D2) For the implant denoted (D1), further comprising: a plunger received within the main body, the plunger coupled to the first wing and the second wing, wherein longitudinal distal movement of the plunger deploys the first wing and the second wing at least partially external from the window.

(D3) For the implant denoted (D1) or (D2), wherein the compressive body comprises teeth configured to engage with an ilium.

(D4) For the implant denoted as any of (D1) through (D3), wherein the first wing comprises a first offset portion and the second wing comprises a second offset portion, and wherein the first offset portion and the second offset portion define an opening therebetween when the distal anchor is in the closed configuration such that the cannula is unobstructed entirely along the length of the implant.

(D5) For the implant denoted as any of (D1) through (D4), wherein the distal end of the main body comprises threads and flutes for self-drilling the implant.

(D6) For the implant denoted as any of (D1) through (D5), wherein the first wing comprises a first slot, wherein a first pin is fixed to the main body and received within the first slot, and wherein the first wing rides along the first pin when moving between the open configuration and the closed configuration.

(D7) For the implant denoted as any of (D1) through (D6), wherein the second wing comprises a second slot, wherein a second pin is fixed to the main body and received within the second slot, and wherein the second wing rides along the second pin when moving between the open configuration and the closed configuration.

(D8) For the implant denoted as any of (D1) through (D7), wherein at least one of the first wing or the second wing comprises one or more fangs configured to engage with cortical bone of a sacrum, wherein when the implant is in the open configuration, the implant is configured to be retracted proximally to anchor the first wing and the second wing against the cortical bone.

(E1) An implant for insertion across a sacroiliac (SI) joint, comprising: a main body defining a longitudinal axis extending along a length of the main body and a lateral axis extending along a width of the main body, the main body comprising: a window extending laterally along the lateral axis of the main body; a distal anchor having an open configuration and a closed configuration, the distal anchor comprising a first wing and a second wing, wherein the first wing and the second wing are housed within the window in the closed configuration, and wherein the first wing and the second wing are deployed at least partially external from the window in the open configuration; and a compressive body coupled to the main body and forming a proximal anchor for the implant, wherein the compressive body is adjustable along the main body to adjust an overall length of the implant, thereby adjusting an amount of compression across the SI joint.

(E2) For the implant denoted as (E1), further comprising: a plunger received within the main body, wherein the plunger is coupled to the first wing and to the second wing, and wherein longitudinal distal movement of the plunger transitions the first wing and the second wing from the closed configuration to the open configuration.

(E3) For the implant denoted as (E1) or (E2), wherein the first wing comprises a first slot therethrough and the second wing comprise a corresponding second slot therethrough, and wherein the implant further comprises: a first pin coupled to the main body and received in the first slot and a second pin coupled to the main body and received in the second slot, wherein when the plunger is advanced distally, the first slot moves along the first pin and the second slot move along the second pin such that a first curvature of the first slot defines a first travel path of the first wing, and a second curvature of the second slot defines a second travel path of the second wing.

(E4) For the implant denoted as any of (E1) through (E3), wherein the first curvature of the first slot is configured to deploy the first wing along a first path that is tangent to a first curve formed by the first wing in the closed configuration, and wherein the second curvature of the second slot is configured to deploy the second wing along a second path that is tangent to a second curve formed by the second wing in the closed configuration.

(E5) For the implant denoted as any of (E1) through (E4), wherein the compressive body is threadedly engaged with a proximal end of the main body.

(E6) For the implant denoted as any of (E1) through (E5), wherein the compressive body comprises one or more engaging features configured to be engaged by an insertion instrument to rotate and thread the compressive body along the proximal end of the main body.

(E7) For the implant denoted as any of (E1) through (E6), wherein the implant is cannulated along the longitudinal axis.

(E8) For the implant denoted as any of (E1) through (E7), wherein the main body comprises a central, non-threaded section having a roughened outer surface to promote bony fusion.

(F1) A method for fusion and stabilization of a sacroiliac (SI) joint, comprising: providing instructions for inserting an implant across the SI joint, the instructions comprising: make a minimally invasive incision on a patient to provide access to the SI joint of the patient; dilate soft tissue of the patient by sequentially advancing dilators over a guide wire, each sequential dilator having a larger width than a previous dilator; insert the implant through the minimally invasive incision, through an ilium, through the SI joint, and into a sacrum of the patient, wherein the implant comprises: a first body having a distal anchor comprising a pair of deployable wings; and a second body having a proximal anchor comprising a compressive element; deploy the pair of deployable wings; and advance the second body distally to engage the compressive element with the ilium and cause compression across the SI joint.

(F2) For the method denoted as (F1), wherein the instructions further comprise: prior to advancing the second body distally, retracting the implant proximally to anchor the pair of deployable wings against cortical bone of the sacrum.

(F3) For the method denoted as (F1) or (F2), wherein the implant defines a central bore extending therethrough and further comprises: a plunger received within the central bore and coupled to the pair of deployable wings, the plunger comprising internal threads, and wherein deploying the pair of deployable wings comprises: engaging the internal threads with an instrument; and rotating the instrument to advance the plunger distally, thereby deploying the pair of deployable wings.

(F4) For the method denoted as any of (F1) through (F3), wherein the instructions further comprise: fill the implant with bone graft through a central bore extending along a length of the implant.

Many different arrangements of the various components depicted, as well as components not shown, are possible without departing from the scope of the claims below. Embodiments of the present disclosure have been described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims. Although the present disclosure has been described with reference to the embodiments illustrated in the attached drawing figures, it is noted that equivalents may be employed, and substitutions made herein, without departing from the scope of the present disclosure as recited in the claims.

The invention claimed is:

1. An implant for insertion across a sacroiliac (SI) joint, comprising:
   a main body defining a longitudinal axis extending along a length of the main body and a lateral axis extending along a width of the main body, the main body comprising:
      a window extending laterally along the lateral axis of the main body;
      a distal end along the length of the main body and comprising a distal anchor having an open configuration and a closed configuration, the distal anchor comprising a first wing and a second wing,
      wherein the first wing and the second wing are housed within the window in the closed configuration, and
      wherein the first wing and the second wing are deployed at least partially external from the window in the open configuration; and
      a threaded proximal end along the length of the main body;
   a compressive body coupled to the threaded proximal end, the compressive body forming a proximal anchor for the implant,
   wherein the compressive body is configured to be threaded along the threaded proximal end to adjust an overall length of the implant, thereby adjusting an amount of compression across the SI joint; and
   a cannula extending along the longitudinal axis.

2. The implant of claim 1, further comprising:
   a plunger received within the main body, the plunger coupled to the first wing and the second wing,
   wherein longitudinal distal movement of the plunger deploys the first wing and the second wing at least partially external from the window.

3. The implant of claim 1, wherein the compressive body comprises teeth configured to engage with an ilium.

4. The implant of claim 1,
   wherein the first wing comprises a first offset portion and the second wing comprises a second offset portion, and
   wherein the first offset portion and the second offset portion define an opening therebetween when the distal anchor is in the closed configuration such that the cannula is unobstructed entirely along the length of the implant.

5. The implant of claim 1,
   wherein the distal end of the main body comprises threads and flutes for self-drilling the implant.

6. The implant of claim 1,
   wherein the implant comprises a first pin,
   wherein the first wing comprises a first slot,
   wherein the first pin is fixed to the main body and received within the first slot, and
   wherein the first wing rides along the first pin when moving between the open configuration and the closed configuration.

7. The implant of claim 6,
   wherein the implant comprises a second pin;
   wherein the second wing comprises a second slot,
   wherein the second pin is fixed to the main body and received within the second slot, and
   wherein the second wing rides along the second pin when moving between the open configuration and the closed configuration.

8. The implant of claim 1,
   wherein at least one of the first wing or the second wing comprises one or more fangs configured to engage with cortical bone of a sacrum,
   wherein when the implant is in the open configuration, the implant is configured to be retracted proximally to anchor the first wing and the second wing against the cortical bone.

9. An implant for insertion across a sacroiliac (SI) joint, comprising:
   a main body defining a longitudinal axis extending along a length of the main body and a lateral axis extending along a width of the main body, the main body comprising:
      a window extending laterally along the lateral axis of the main body;
      a distal anchor having an open configuration and a closed configuration, the distal anchor comprising a first wing and a second wing,
      wherein the first wing and the second wing are housed within the window in the closed configuration, and
      wherein the first wing and the second wing are deployed at least partially external from the window in the open configuration; and
   a compressive body coupled to the main body and forming a proximal anchor for the implant,
   wherein the compressive body is adjustable along the main body to adjust an overall length of the implant, thereby adjusting an amount of compression across the SI joint.

10. The implant of claim 9, further comprising:
    a plunger received within the main body,
    wherein the plunger is coupled to the first wing and to the second wing, and
    wherein longitudinal distal movement of the plunger transitions the first wing and the second wing from the closed configuration to the open configuration.

11. The implant of claim 10,
    wherein the first wing comprises a first slot therethrough and the second wing comprise a corresponding second slot therethrough, and
    wherein the implant further comprises:
       a first pin coupled to the main body and received in the first slot and a second pin coupled to the main body and received in the second slot, wherein when the plunger is advanced distally, the first slot moves along the first pin and the second slot move along the second pin such that a first curvature of the first slot defines a first travel path of the first wing, and a second curvature of the second slot defines a second travel path of the second wing.

12. The implant of claim 11,
wherein the first curvature of the first slot is configured to deploy the first wing along a first path that is tangent to a first curve formed by the first wing in the closed configuration, and
wherein the second curvature of the second slot is configured to deploy the second wing along a second path that is tangent to a second curve formed by the second wing in the closed configuration.

13. The implant of claim 9, wherein the compressive body is threadedly engaged with a proximal end of the main body.

14. The implant of claim 13, wherein the compressive body comprises one or more engaging features configured to be engaged by an insertion instrument to rotate and thread the compressive body along the proximal end of the main body.

15. The implant of claim 9, wherein the implant is cannulated along the longitudinal axis.

16. The implant of claim 9, wherein the main body comprises a central, non-threaded section having a roughened outer surface to promote bony fusion.

17. A method for fusion and stabilization of a sacroiliac (SI) joint, comprising:
providing instructions for inserting an implant across the SI joint, the instructions comprising:
make a minimally invasive incision on a patient to provide access to the SI joint of the patient;
dilate soft tissue of the patient by sequentially advancing dilators over a guide wire, each sequential dilator having a larger width than a previous dilator;
insert the implant through the minimally invasive incision, through an ilium, through the SI joint, and into a sacrum of the patient,
wherein the implant comprises:
a first body having a distal anchor comprising a pair of deployable wings; and
a second body having a proximal anchor comprising a compressive element;
deploy the pair of deployable wings; and
advance the second body distally to engage the compressive element with the ilium and cause compression across the SI joint.

18. The method of claim 17, wherein the instructions further comprise:
prior to advancing the second body distally, retracting the implant proximally to anchor the pair of deployable wings against cortical bone of the sacrum.

19. The method of claim 17,
wherein the implant defines a central bore extending therethrough and further comprises:
a plunger received within the central bore and coupled to the pair of deployable wings, the plunger comprising internal threads or a female hex, and
wherein deploying the pair of deployable wings comprises:
engaging the internal threads or the female hex with an instrument; and
rotating the instrument to advance the plunger distally, thereby deploying the pair of deployable wings.

20. The method of claim 17, wherein the instructions further comprise:
fill the implant with bone graft through a central bore extending along a length of the implant.

* * * * *